United States Patent
Proud et al.

(10) Patent No.: US 9,723,898 B2
(45) Date of Patent: *Aug. 8, 2017

(54) WEARABLE DEVICE WITH INTERIOR FRAME

(71) Applicant: Hello Inc., San Francisco, CA (US)

(72) Inventors: James Proud, San Francisco, CA (US); Bryan Fan, San Francisco, CA (US); Robert Shook, San Francisco, CA (US); Joaquin Fernandez, San Francisco, CA (US)

(73) Assignee: Hello Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/180,026

(22) Filed: Jun. 12, 2016

(65) Prior Publication Data

US 2017/0020241 A1     Jan. 26, 2017

Related U.S. Application Data

(63) Continuation of application No. 14/037,747, filed on Sep. 26, 2013, now Pat. No. 9,420,857, which is a continuation-in-part of application No. 14/037,717, filed on Sep. 26, 2013, now Pat. No. 9,055,791, and a continuation-in-part of application No. 14/037,643, filed on Sep. 26, 2013, now Pat. No. 9,462,856, and a continuation-in-part of application No. 14/037,594, filed on Sep. 26, 2013, now Pat. No. 9,427,053, and a continuation-in-part of application No. 14/037,536, filed on Sep. 26, 2013, now Pat. No. 9,414,651, and a continuation-in-part of application No. 14/036,382, filed on Sep. 25, 2013, now Pat. No. 9,367,793, and a continuation-in-part of application No. 14/036,287, filed on Sep. 25, 2013, now Pat. No. 9,420,856, and a continuation-in-part of application No. 14/036,111, filed on Sep. 25, 2013, now Pat. No. 9,427,160, and a continuation-in-part of application No. 13/923,909, filed on Jun. 21, 2013, now Pat. No. 9,407,097, and (Continued)

(51) Int. Cl.
| | |
|---|---|
| A44C 5/00 | (2006.01) |
| A61B 5/00 | (2006.01) |
| A61B 5/11 | (2006.01) |
| G06Q 20/08 | (2012.01) |
| G06Q 40/04 | (2012.01) |

(52) U.S. Cl.
CPC .......... *A44C 5/0015* (2013.01); *A61B 5/0002* (2013.01); *A61B 5/1118* (2013.01); *A61B 5/681* (2013.01); *G06Q 20/0855* (2013.01); *G06Q 40/04* (2013.01); *A44D 2203/00* (2013.01)

(58) Field of Classification Search
None
See application file for complete search history.

(56) References Cited

U.S. PATENT DOCUMENTS 9,420,857 B2 * 8/2016 Proud ................. A44C 5/0015
9,424,508 B2 * 8/2016 Proud ............. G06K 19/07762

* cited by examiner

*Primary Examiner* — Kristy A Haupt
(74) *Attorney, Agent, or Firm* — Paul Davis

(57) ABSTRACT

A wearable device includes a wearable device structure having first and second ends. A support member is positioned at least partially positioned in the wearable device structure. Electronic circuitry is at a surface or an interior of the wearable device. The electronic circuitry provides at least identification of the wearable device. One or more batteries are coupled to the electronic circuitry.

20 Claims, 37 Drawing Sheets

Related U.S. Application Data a continuation-in-part of application No. 13/923,637, filed on Jun. 21, 2013, now Pat. No. 8,810,430, and a continuation-in-part of application No. 13/923,614, filed on Jun. 21, 2013, now Pat. No. 8,850,421, and a continuation-in-part of application No. 13/923,809, filed on Jun. 21, 2013, now Pat. No. 9,425,627, and a continuation-in-part of application No. 13/923,750, filed on Jun. 21, 2013, now Pat. No. 9,438,044, and a continuation-in-part of application No. 13/923,583, filed on Jun. 21, 2013, now abandoned, and a continuation-in-part of application No. 13/923,560, filed on Jun. 21, 2013, now Pat. No. 8,803,366, and a continuation-in-part of application No. 13/923,543, filed on Jun. 21, 2013, and a continuation-in-part of application No. 13/923,937, filed on Jun. 21, 2013.

(60) Provisional application No. 61/823,502, filed on May 15, 2013, provisional application No. 61/812,083, filed on Apr. 15, 2013, provisional application No. 61/772,265, filed on Mar. 4, 2013.

204

202

ACTIVITY NAME: RUNNING

ACTIVITY DESCRIPTION: RUNNING IN MILLENIUM PARK

DATE: 5-01-07 ~306

TIME START: 2:15 pm ~308   TIME END: 3:30 PM ~310

ITEMS TO BE TRACKED: RUNNING SHOES / HEADPHONES ~312

SENSOR PARAMETERS
STRIDE LENGTH = 3 FT.
HEART RATE BASELINE = 1/2 SEC. ~316

SENSORS: RUNNING SHOES / HEART RATE MONITOR ~314

SERVICES: WEATHER ~320

FIG. 16

| ACTIVITY | ACTIVITY ID | SENSOR/ DEVICE NAME | SENSOR/ DEVICE IP ADDRESS | DATA CONFIG |
|---|---|---|---|---|
| RUNNING | 111 | SHOES 1<br>HEART | 1.23.342<br>1.23.341 | HEART RATE BASELINE 1/2s<br>OPTIMAL SAMPLING 1s<br>BASELINE ALGORITHM<br>OPTIMAL ALGORITHM<br>SHOES:<br>SAMPLING RATE;<br>BASELINE:<br>OPTIMAL SAMPLING: |
| SKATING | 112 | SKATES 1<br>JACKET | 1.23.341<br>1.23.339 | |
| WORK OUT | 113 | STAIR CLIMBER<br>TREAD MILL | 1.23.338<br>1.23.337 | HEART RATE UTILIZATION<br>CALORIES |
| COOKING/ DINNER | 116 | REFRIGERATOR<br>CABINET 2<br>CABINET 3 | 1.23.340<br>1.23.341<br>1.23.342 | CALORIES<br>FAT GRAMS<br>% UTILIZED |
| WATCH TV | 115 | TV<br>CABLE BOX | 1.23.344<br>1.23.346 | ON/OFF<br>CHANNEL |

FIG. 17B

WEARABLE DEVICE WITH INTERIOR FRAME

CROSS-REFERENCE TO RELATED APPLICATIONS

This application is a continuation of U.S. Ser. No. 14/037,747, which is a continuation in part of U.S. Ser. No. 14/037,717, filed Sep. 26, 2013, U.S. Ser. No. 14/037,643, filed Sep. 26, 2013, U.S. Ser. No. 14/037,594, filed Sep. 26, 2013, U.S. Ser. No. 14/037,536, filed Sep. 26, 2013, U.S. Ser. No. 14/036,382, filed Sep. 25, 2013, U.S. Ser. No. 14/036,287, filed Sep. 25, 2013, U.S. Ser. No. 14/036,111, filed Sep. 25, 2013, U.S. Ser. Nos. 13/923,909, 13/923,637, 13/923,614, 13/923,809, 13/923,750, 13/923,583, 13/923,560, 3/923,543, and 13/923,937, all filed Jun. 21, 2013 and all of which claim the benefit of U.S. 61/772,265, filed Mar. 4, 2013, U.S. 61/812,083, filed Apr. 15, 2013 and 61/823,502, filed May 15, 2013. All of the above-identified applications are fully incorporated herein by reference.

BACKGROUND

Field of the Invention

The present invention is directed to wearable devices with magnets for fastening, and more particularly to a wearable device with an interior frame to provide support for the magnets.

Description of the Related Art

As portable electronic devices become more compact, and the number of functions performed by a given device increase, it has become a significant challenge to design a user interface that allows users to easily interact with a multifunction device. This challenge is particular significant for handheld portable devices, which have much smaller screens than desktop or laptop computers. This situation is unfortunate because the user interface is the gateway through which users receive not only content but also responses to user actions or behaviors, including user attempts to access a device's features, tools, and functions. Some portable communication devices (e.g., mobile telephones, sometimes called mobile phones, cell phones, cellular telephones, and the like) have resorted to adding more pushbuttons, increasing the density of push buttons, overloading the functions of pushbuttons, or using complex menu systems to allow a user to access, store and manipulate data. These conventional user interfaces often result in complicated key sequences and menu hierarchies that must be memorized by the user.

A large number of the top health problems are either caused in whole or in part by an unhealthy lifestyle. More and more people lead fast-paced, achievement-oriented lifestyles that often result in poor eating habits, high stress levels, and lack of exercise, poor sleep habits and the inability to find the time to center the mind and relax. Recognizing this fact, people are becoming increasingly interested in establishing a healthier lifestyle.

Traditional medicine, embodied in the form of an HMO or similar organizations, does not have the time, the training, or the reimbursement mechanism to address the needs of those individuals interested in a healthier lifestyle. There have been several attempts to meet the needs of these individuals, including a perfusion of fitness programs and exercise equipment, dietary plans, self-help books, alternative therapies, and most recently, a plethora of health information web sites on the Internet. Each of these attempts is targeted to empower the individual to take charge and get healthy. Each of these attempts, however, addresses only part of the needs of individuals seeking a healthier lifestyle and ignores many of the real barriers that most individuals face when trying to adopt a healthier lifestyle. These barriers include the fact that the individual is often left to himself or herself to find motivation, to implement a plan for achieving a healthier lifestyle, to monitor progress, and to brainstorm solutions when problems arise; the fact that existing programs are directed to only certain aspects of a healthier lifestyle, and rarely come as a complete package; and the fact that recommendations are often not targeted to the unique characteristics of the individual or his life circumstances.

Individual monitoring has been accomplished by electronic monitoring and analysis. Vital signs derived from physiological waveforms a monitored and alarms generated if predetermined limits were exceeded by the vital signs. Monitoring equipment has become more complex as more physiological data is collected and more in-depth analysis of the data is required, such as calculation of vital signs and trends which required memory and processing capability.

With the introduction of monitoring units, attempts have been made to provide a measure of remote monitoring by transmitting analog waveforms of physiological data from the bedside unit to equipment at a central station such as a nurse's station. Subsequently remote monitoring efforts include analog waveforms plus digital representations for display. Both the bedside and remote monitoring activity act to give alarms upon sensing an abnormal condition and to store data and analyze data to obtain vital signs and trends. But these systems are basically one-way systems reporting physiological data from the user. There is no communication with the user as a part of an interactive integrated system.

Telemetry systems can be implemented to acquire and transmit data from a remote source. Some telemetry systems provide information about a user's activities.

It is becoming commonplace to use wireless packet data service networks for effectuating data sessions with. In some implementations, unique identifications (ID) need to be assigned to the devices in order to facilitate certain aspects of service provisioning, e.g., security, validation and authentication, et cetera. In such scenarios, it becomes imperative that no two devices have the same indicium (i.e., collision). Further, provisioning of such indicia should be flexible so as to maintain the entire pool of indicia to a manageable level while allowing for their widespread use in multiple service environments.

Medical telemetry systems may comprise an alarm adapted to identify high risk users and/or users requiring special assistance. Some medical procedures and diagnostic examinations require the removal of any telemetry system components attached directly to a user. One problem with conventional medical telemetry systems is that the process of removing telemetry system components for purposes of performing a medical procedure or diagnostic examination can generate a false alarm. False alarms unnecessarily tax hospital resources and interfere with the working environment.

There is a need for improved wearable devices. There is a further need for a wearable device with electrical components with internal circuitry and a frame adjacent to the circuitry.

SUMMARY OF THE INVENTION

An object of the present invention is to provide an improved wearable device.

Another object of the present invention is to provide an improved wearable device that includes a plurality of magnets that are used to coupled one end of the wearable device with a second end of the wearable device.

Yet another object of the present invention is to provide a wearable device that utilizes a plurality of magnets for coupling one end to another end, and the wearable device includes electronic circuitry at a surface or an interior of the wearable device, the electronic circuitry providing at least identification of the wearable device.

A further object of the present invention is to provide a wearable device that utilizes a plurality of magnets to couple first and second ends of the wearable device, with the wearable device including a support structure.

Still another object of the present invention is to provide a wearable device that utilizes a plurality of magnets to couple first and second ends of the wearable device, with the wearable device including a support structure for the magnets.

Another object of the present invention is to provide a wearable device that utilizes a plurality of magnets to couple first and second ends of the wearable device, with the wearable device configured to be in communication with a social network and/or payment system.

Another object of the present invention is to provide a wearable device that utilizes a plurality of magnets to couple first and second ends of the wearable device, where the wearable device is a mobile device.

These and other objects of the present invention are achieved a wearable device with a wearable device structure having first and second ends. A support member is positioned at least partially positioned in the wearable device structure. Electronic circuitry is at a surface or an interior of the wearable device. The electronic circuitry provides at least identification of the wearable device. One or more batteries are coupled to the electronic circuitry.

BRIEF DESCRIPTION OF THE DRAWINGS

FIG. 16 illustrates one embodiment of an activity manager in one embodiment of the present invention.

DETAILED DESCRIPTION

Figure 1A:
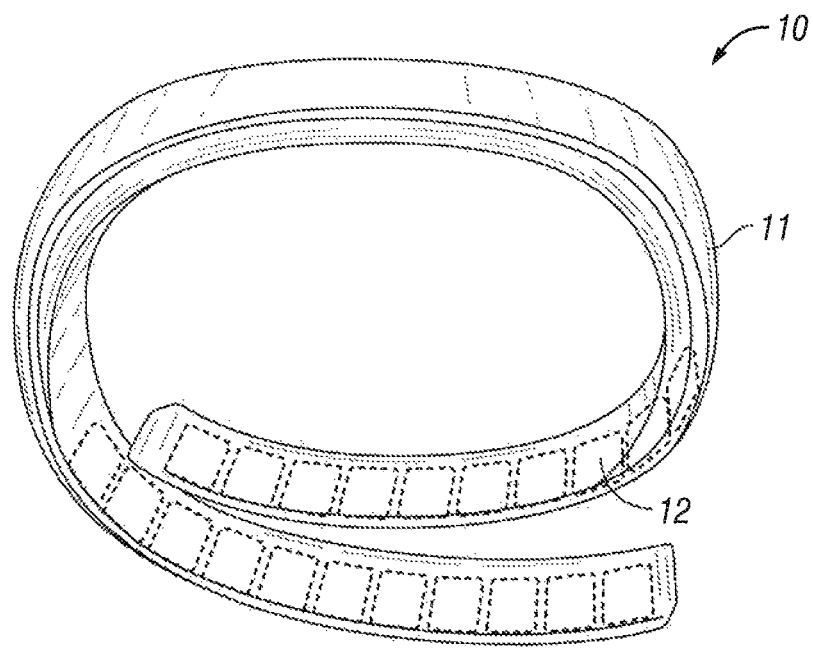
FIGS. 1(a) and 1(b) illustrate one embodiment of a wearable device of the present invention, where one size fits all.

As used herein, the term engine refers to software, firmware, hardware, or other component that can be used to effectuate a purpose. The engine will typically include software instructions that are stored in non-volatile memory (also referred to as secondary memory). When the software instructions are executed, at least a subset of the software instructions can be loaded into memory (also referred to as primary memory) by a processor. The processor then executes the software instructions in memory. The processor may be a shared processor, a dedicated processor, or a combination of shared or dedicated processors. A typical program will include calls to hardware components (such as I/O devices), which typically requires the execution of drivers. The drivers may or may not be considered part of the engine, but the distinction is not critical.

As used herein, the term database is used broadly to include any known or convenient means for storing data, whether centralized or distributed, relational or otherwise.

As used herein a mobile device includes, but is not limited to, a cell phone, such as Apple's iPhone®, other portable electronic devices, such as Apple's iPod Touches®, Apple's iPads®, and mobile devices based on Google's Android® operating system, and any other portable electronic device that includes software, firmware, hardware, or a combination thereof that is capable of at least receiving the signal, decoding if needed, exchanging information with a transaction server to verify the buyer and/or seller's account information, conducting the transaction, and generating a receipt. Typical components of mobile device may include but are not limited to persistent memories like flash ROM, random access memory like SRAM, a camera, a battery, LCD driver, a display, a cellular antenna, a speaker, a BLUETOOTH® circuit, and WIFI circuitry, where the persistent memory may contain programs, applications, and/or an operating system for the mobile device.

As used herein, the terms "social network" and "SNET" comprise a grouping or social structure of devices and/or individuals, as well as connections, links and interdependencies between such devices and/or individuals. Members or actors (including devices) within or affiliated with a SNET may be referred to herein as "nodes", "social devices", "SNET members", "SNET devices", "user devices" and/or "modules". In addition, the terms "SNET circle", "SNET group" and "SNET sub-circle" generally denote a social network that comprises social devices and, as contextually appropriate, human SNET members and personal area networks ("PANs").

A used herein, the term "wearable device" is anything that can be worn by an individual and that has a back side that in some embodiments contacts a user's skin and a face side. Examples of wearable device include but are not limited to a cap, arm band, wristband, garment, and the like. The term "wearable device" can also be a monitoring device if it includes monitoring elements.

As used herein, the term "computer" is a general purpose device that can be programmed to carry out a finite set of arithmetic or logical operations. Since a sequence of operations can be readily changed, the computer can solve more than one kind of problem. A computer can include of at least one processing element, typically a central processing unit (CPU) and some form of memory. The processing element carries out arithmetic and logic operations, and a sequencing and control unit that can change the order of operations based on stored information. Peripheral devices allow information to be retrieved from an external source, and the result of operations saved and retrieved.

As used herein, the term "Internet" is a global system of interconnected computer networks that use the standard Internet protocol suite (TCP/IP) to serve billions of users worldwide. It is a network of networks that consists of millions of private, public, academic, business, and government networks, of local to global scope, that are linked by a broad array of electronic, wireless and optical networking technologies. The Internet carries an extensive range of information resources and services, such as the inter-linked hypertext documents of the World Wide Web (WWW) and the infrastructure to support email. The communications infrastructure of the Internet consists of its hardware components and a system of software layers that control various aspects of the architecture.

As used herein, the term "extranet" is a computer network that allows controlled access from the outside. An extranet can be an extension of an organization's intranet that is extended to users outside the organization that can be partners, vendors, and suppliers, in isolation from all other Internet users. An extranet can be an intranet mapped onto the public Internet or some other transmission system not accessible to the general public, but managed by more than one company's administrator(s). Examples of extranet-style networks include but are not limited to:
- LANs or WANs belonging to multiple organizations and interconnected and accessed using remote dial-up
- LANs or WANs belonging to multiple organizations and interconnected and accessed using dedicated lines
- Virtual private network (VPN) that is comprised of LANs or WANs belonging to multiple organizations, and that extends usage to remote users using special "tunneling" software that creates a secure, usually encrypted network connection over public lines, sometimes via an ISP.

As used herein, the term "Intranet" is a network that is owned by a single organization that controls its security policies and network management. Examples of intranets include but are not limited to:
- A LAN
- A Wide-area network (WAN) that is comprised of a LAN that extends usage to remote employees with dial-up access
- A WAN that is comprised of interconnected LANs using dedicated communication lines
- A Virtual private network (VPN) that is comprised of a LAN or WAN that extends usage to remote employees or networks using special "tunneling" software that creates a secure, usually encrypted connection over public lines, sometimes via an Internet Service Provider (ISP).

For purposes of the present invention, the Internet, extranets and intranets collectively are referred to as ("Network Systems").

As used herein, the term "user" includes but is not limited to a person, under a physician's care, interested in maintaining health, interested in maintaining a healthy lifestyle and/or physiologic balance, interested in monitoring lifestyle conditions, including but not limited to, the way a person goes about daily living including but not limited to, habits, exercise, diet, medical conditions and treatments, career, financial means, emotional status, and the like.

As used herein, the term "user monitoring" includes: (i) Cardiac monitoring, which generally refers to continuous electrocardiography with assessment of the user's condition relative to their cardiac rhythm. A small monitor worn by an ambulatory user for this purpose is known as a Holter monitor. Cardiac monitoring can also involve cardiac output monitoring via an invasive Swan-Ganz catheter (ii) Hemodynamic monitoring, which monitors the blood pressure and blood flow within the circulatory system. Blood pressure can be measured either invasively through an inserted blood pressure transducer assembly, or noninvasively with an inflatable blood pressure cuff. (iii) Respiratory monitoring, such as: pulse oximetry which involves measurement of the saturated percentage of oxygen in the blood, referred to as SpO2, and measured by an infrared finger cuff, capnography, which involves CO2 measurements, referred to as EtCO2 or end-tidal carbon dioxide concentration. The respiratory rate monitored as such is called AWRR or airway respiratory rate). (iv) Respiratory rate monitoring through a thoracic transducer belt, an ECG channel or via capnography, (v) Neurological monitoring, such as of intracranial pressure. Special user monitors can incorporate the monitoring of brain waves electroencephalography, gas anesthetic concentrations, bispectral index (BIS), and the like, (vi) Blood glucose monitoring using glucose sensors. (vii) Childbirth monitoring with sensors that monitor various aspects of childbirth. (viii) Body temperature monitoring which in one embodiment is through an adhesive pad containing a thermoelectric transducer. (ix) Stress monitoring that can utilize sensors to provide warnings when stress levels signs are rising before a human can notice it and provide alerts and suggestions. (x) Epilepsy monitoring. (xi) Toxicity monitoring, (xii) general lifestyle parameters and the like.

Additionally the present invention can be used to detect differences for a variety of blood tests, including but not limited to tests for the following: sodium, potassium, chloride, urea, creatinine, calcium, albumin, fasting glucose, amylase, carcinoembryonic antigen, glycosylated hemoglobin, hemoglobin, erthrocytes hemoglobin and the like.

In various embodiments, the present invention provides systems and methods for monitoring and reporting human physiological information, life activities data of the individual, generate data indicative of one or more contextual parameters of the individual, monitor the degree to which an individual has followed a routine and the like, along with providing feedback to the individual.

In certain embodiments, the suggested routine may include a plurality of categories, including but not limited to, nutrition, activity level, mind centering, sleep, daily activities, exercise and the like.

In general, according to the present invention, data relating to the physiological state, the lifestyle and certain contextual parameters of an individual is collected and transmitted, either subsequently or in real-time, to a site, can remote from the individual, where it is stored for later manipulation and presentation to a recipient, can over an electronic network such as the Internet. Contextual parameters as used herein means parameters relating to the environment, surroundings and location of the individual, including, but not limited to, air quality, sound quality, ambient temperature, global positioning and the like.

Figure 1B:
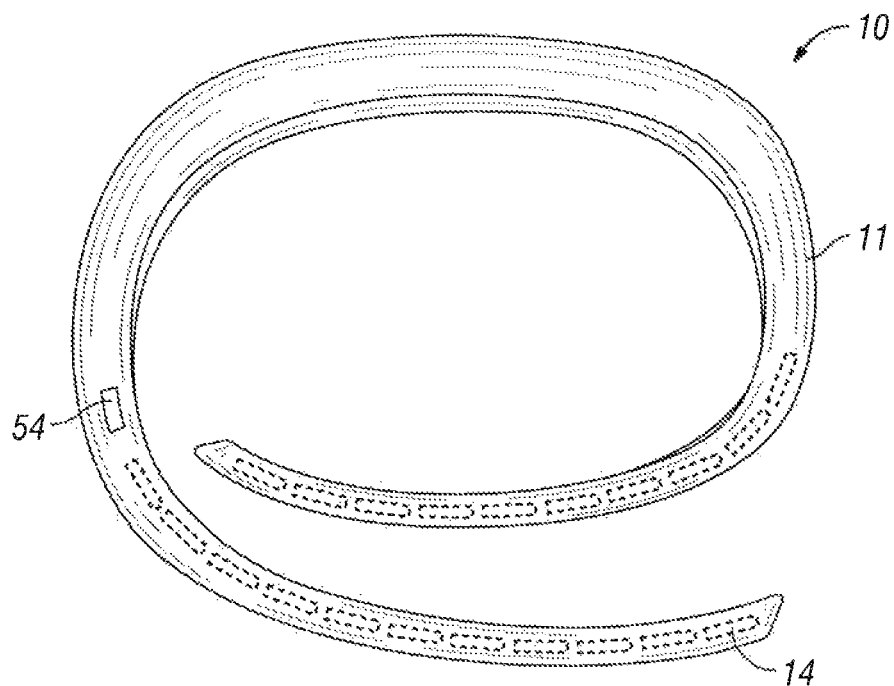

In various embodiments, the present invention provides a user monitoring device 10, including but not limited to, a wearable device, where one size fits all. Monitoring device 10 can be a sensor enabled item 10, including but not limited to a wearable device, gym bag, wallet, file, shoes, skis, and the like that has its own unique ID. As illustrated in FIGS. 1(a) and 1(b), in one embodiment of the present invention, the user monitoring device 10 includes a plurality of magnets 12. All of the magnets 12 are positioned at or in an interior of monitoring or wearable device structure 11, with in one embodiment at least a portion of adjacent magnets having opposite polarity, with a length suitable to be worn by all people. In one embodiment, the length of the user monitoring device 10 can be 10-12 inches. The magnets 12 are positioned along an interior of the user monitoring device 10 to be provided for good conformation to a user's wrist. The monitoring device 10 includes a structure 11 that can be made of a variety of materials, and it is this structure of the monitoring device that includes the magnets 12.

In various embodiments, the wearable device 10 and wearable device structure 11 can be made as a whole piece or segment, or in separate segments that can be coupled together, (i) mechanically, (ii) by adhesion, (iii) by heat staking, (iv) with magnets, (v) other coupling mechanisms, and the like.

As previously mentioned, at least a portion of the magnets are in an interior of wearable device structure 11. In one embodiment, illustrated in FIG. 1(c), adjacent magnets 12 at or in wearable device structure 11 have opposite polarities e.g, one magnet has one polarity and the adjacent magnetic 12 has a different polarity. In another embodiment, adjacent magnets 12 are magnetized in different directions, which can be along their lengths, widths or thicknesses, e.g. in x, y and z directions. In one embodiment, at least a portion of the magnets 12 are magnetized through their widths or thickness, e.g., depth of the magnet 12. In one embodiment, at least a portion of the magnets 12 are provided with a first portion with one polarity and a second portion with a different polarity, FIG. 1(d). In one embodiment, the different sections of at least a portion of a magnet 12 can have different sections with different polarities, and the sections need be of the same size or strength. As non-limiting example, a magnet can have 10%, 20% 30%, 40%, 50% of a first section with a first polarity and a second portion of the magnet with a different polarity. The first and second portions need not be of the same physical size. In these various embodiments, the magnets are used to couples a first end of wearable device structure 11 with a second end. In one embodiment, the coupling between the first and second ends wearable structure 11 use the magnets 12 to create a closure and an engagement of the wearable device 10 with a body part, including but not limited to a wrist. In one embodiment, this coupling can create a closure and/or a locking of the first and second ends of the wearable device structure 11, as illustrated in FIG. 1(e). This occurs when one end of the wearable device 10 with magnets 12 is positioned adjacent to a second end of the wearable device 10.

As a non-limiting example, shown in FIG. 1(e), one end of the wearable device structure 11 overlaps the second end, e.g, on end on top of the other, or one distal end of one end in physical contact with a distal end of a second end. As a non-limiting example, the distance between the overlapped magnets 12 when one end overlaps is adjacent to the other end ("X"), measured from facing faces of the magnets 12, is, (i) 0.1 to 10 mm, (ii) 0.1 to 5 mm, (iii) 0.25 to 3 mm (iv) 0.5 to 1 mm, (v) 0.5 to 2 mm, (vi) 0.25 to 5 mm, and the like. Other ranges are also possible.

It will be appreciated that the overlapped magnets 12 do not have to be absolutely overlapped and there can be some offset, e.g. a magnet 12 at a first end does not have to be in complete alignment with a corresponding magnet at a second end. As non-limiting examples, the overlap between corresponding magnets 12 of a first end to a second end can be an overlap of magnet 12 areas of, (i) 10%, (ii) 25%, (iii) 50%, (iv) 75%, and the like. Other percentages of overlap are possible with the present invention.

Figure 1C:
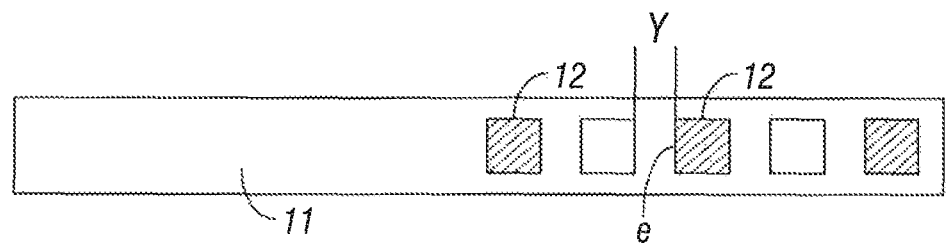
FIG. 1(c) illustrates an embodiment of the present invention with at least a portion of adjacent magnets at or in a wearable device structure have opposite polarities.
Figure 1D:
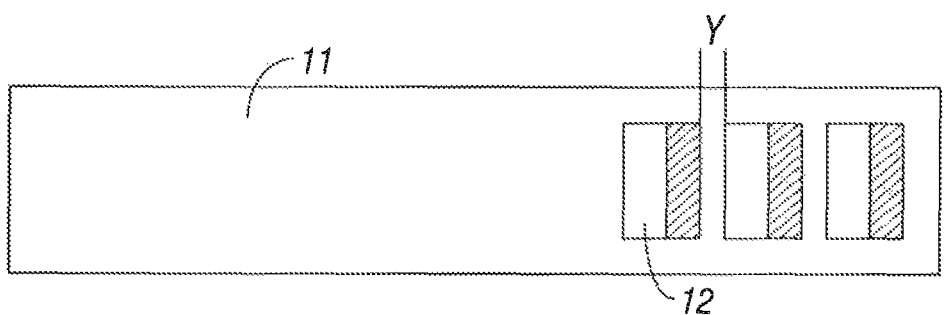
FIG. 1(d) illustrates an embodiment of the present invention where at least a portion of the magnets are provided with a first portion with one polarity and a second portion with a different polarity.
Figure 1E:
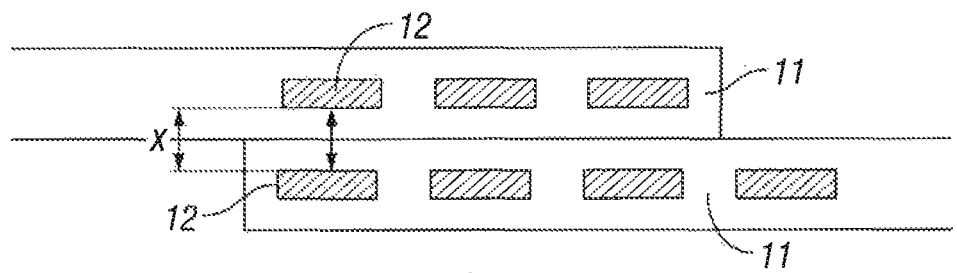
FIG. 1(e) illustrates an embodiment of the present invention where at least a portion of magnets of first and second ends of the wearable device structure couple the two ends together.

Referring now to FIG. 1(c), in one embodiment, the distance ("Y") between adjacent magnets 12 at a first or second end wearable device structure 11 can be in the range of, (i) 0.1 to 10 mm, (ii) 0.25 to 7.5 mm, (iii) 12 is 0.5 mm to 5 mm, and the like.

Figure 1F:
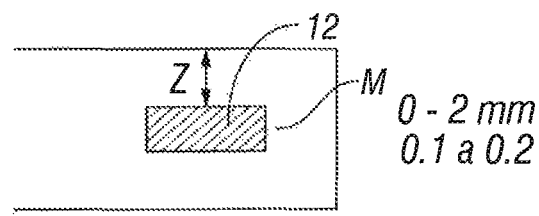
FIG. 1(f) illustrates an embodiment of the present invention with a distance ("Z") of at least a portion of the magnets positioned in an interior of wearable device structure from the exterior side walls of the wearable device structure.

As a non-limiting example, and as illustrated in FIG. 1(f), the distance ("Z") of at least a portion of the magnets 12 positioned in an interior of wearable device structure 11 from the exterior side walls of the wearable device structure 11 is, (i) 0.1 mm to 2.0 mm, (ii) 0.25 to 5 mm, (iii) 0.1 to 3 mm, and the like.

As non-limiting examples, the size of magnets 12 is: (i) length, (0.5 to 30 mm), (1 to 20 mm), (2 to 10 mm); (ii), width, (0.5 mm to 30 mm), (1 to 20 mm), (2 to 10 mm); and (iii) thickness/depth, (0.5 mm to 10 mm), (1 to 7.5 mm), (2 to 5 mm), and the like.

As non-limiting examples, the strength of the magnets 12 is from, N25 to N52, N30 to N52, N40 to N52, and the like.

In various embodiments, the temperatures that the magnets 12 can be exposed to during, processing, cleaning and/or manufacturing, and the like, of the wearable device 10 is from, 100 to 500 degrees ° F., 150 to 450° F., 200 to 400° F., and the like. As a non-limiting example, the magnets 12 can be as follows: M (212° F.)-H (248° F.) SH (302° F.)-UH (356° F.) and EH (392° F.).

In one embodiment, the magnets 12 are all sealed in wearable device 10. Sealing can be done by a variety of mechanisms, including but not limited to, molding, over-molding, partially over-molding the magnets 12 with the materials of the wearable device structure 11, the use of other suitable sealing mechanism, including but not limited to liquids including but not limited to ferrofluids, adhesives and the like. The sealing is done in a manner to not interfere with the operation of the magnets. In one embodiment, the magnets 12 are sealed in or at the wearable device 10 that is substantially made of silicone rubber, as more fully described hereafter.

Figure 1G:
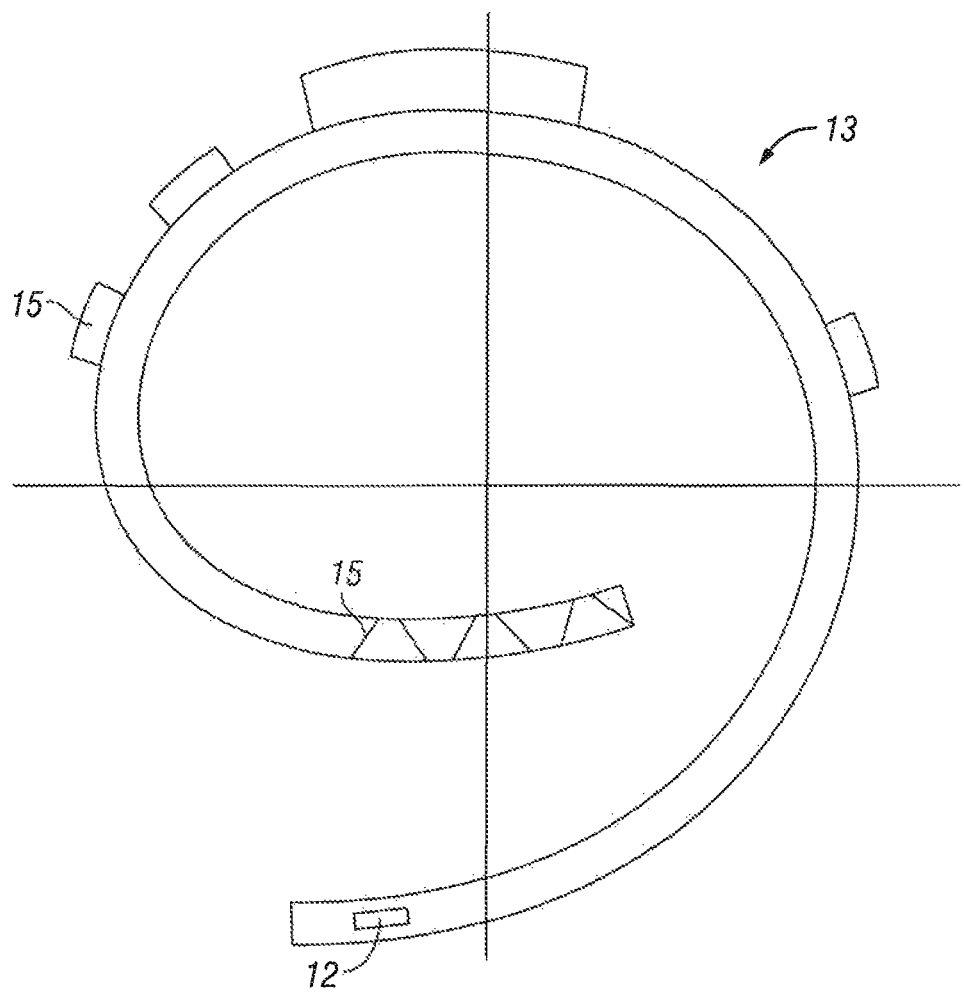
FIG. 1(g) illustrates one embodiment of the present invention where electronic components and circuitry are coupled to a support structure or frame.

In one embodiment, illustrated in FIG. 1(g), the magnets 12 are coupled to a support structure or frame 13. All or a portion of the wearable device 10 electrical components and circuitry 15, as more fully described hereafter, can be attached to and/or positioned within the frame 13. The frame 13 can be made of a variety of materials, including but not limited to a thermoplastic that can be ground up and used again. Other suitable materials include metals, composites and the like.

The positioning of the electrical components and circuitry 15 is such that the positioning does not interfere in the operation and the magnets 12 and vice versa.

Figure 1H:
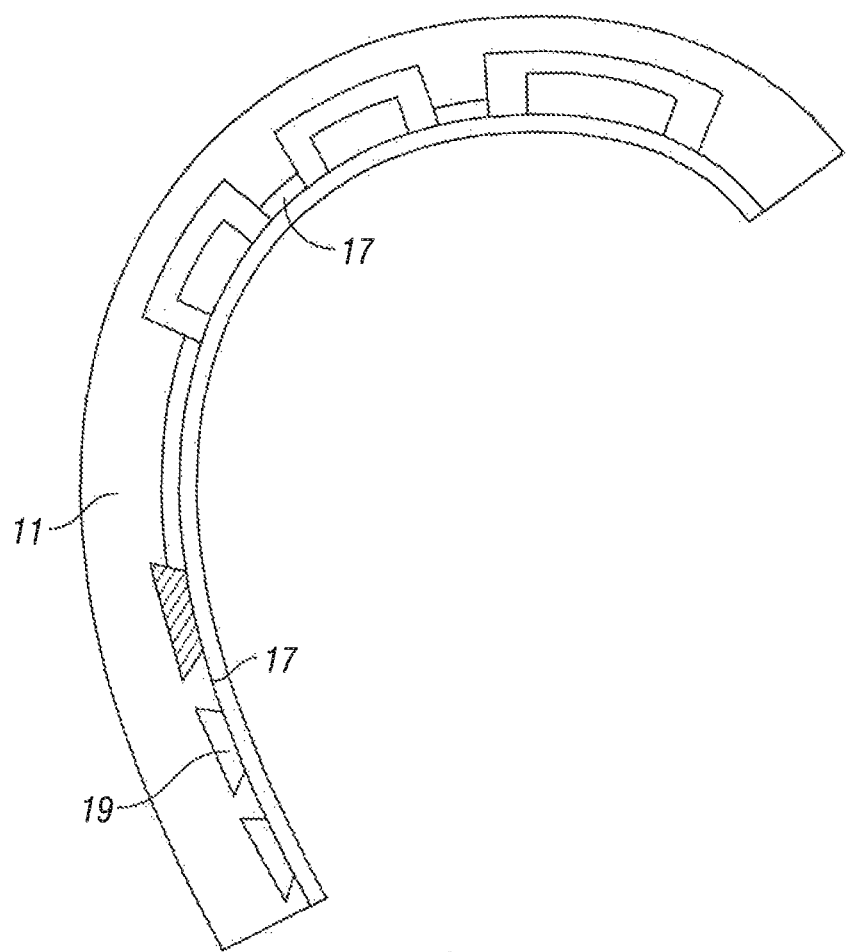
FIG. 1(h) illustrates one embodiment of the present invention and is a cross-sectional view of the wearable device structure, illustrating the frame and a living hinge.

FIG. 1(h) is a cross-sectional view of wearable device structure 11 and illustrates an embodiment where the frame 13 includes a living hinge 17. The living hinge can flex and hinge by in self, without additional elements.

The frame 13 protects the magnets 12 and electronic components and circuitry 15, and can also protect sensors 14, from torsional and mechanical forces imparted to wearable device 10. As non-limiting examples, the frame 13 protects against mechanical forces imparted to the magnets 12 and the electronic components and circuitry 15 in amounts that do not exceed: pull force: 0.5 to 100 kgf, (stretching of the wearable device 10); bend force: 0.5 to 100 kgf (bending of the wearable device 10); shear force: 0.5 to 100 kgf (shearing of the wearable device 10; and a torsional strength in the range of 0.25 to 50 Ncm (twisting of the wearable device 10)

Figure 1I:
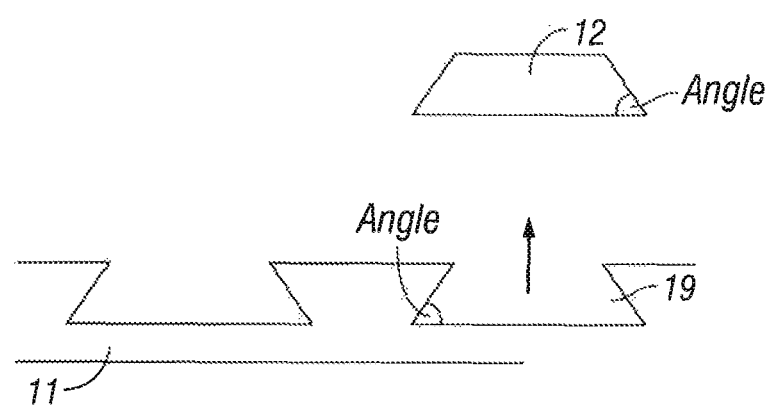
FIG. 1(i) illustrates an embodiment of the present invention where the wearable device structure includes an undercut

As illustrated in FIG. 1(i), the wearable device structure 11 can include an undercut 19 that enables the magnets to be slid into the wearable device structure 11 and be retained by the wearable device structure 11 itself without the need for adhesives or other retaining elements or compositions. One or all six sides of a magnet 12 can be retained with an undercut 19.

As a non-limited example, the undercut 19 of the wearable device structure 11, can be at an undercut angle of from 0 to 45°. The undercut 19 can be in any variety of different geometries depending on the undercut angle. Not all of a magnet's periphery need to included in the undercut 19. The amount of the magnet 12 in an undercut of the wearable device structure 10 can vary, but should be sufficient to retain the magnet 12.

Figure 1J:
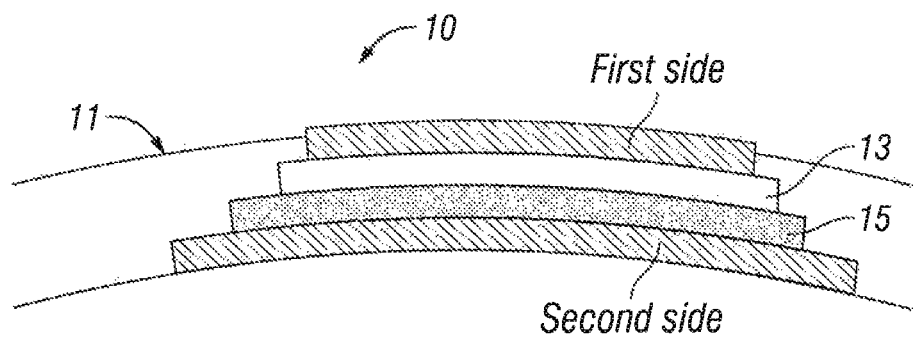
FIG. 1(j) illustrates an embodiment of the present invention illustrating a positioning of the electronic circuitry and the frame in relation to first and second sides of the wearable device.

FIG. 1(j) illustrates an embodiment of the positioning of an electronic circuitry 15, frame 13 and first and second sides of wearable device 11.

One or more sensors 14 are coupled to the user monitoring device 10. The sensors are measuring devices. As a non-limiting example, the measuring device or sensors 14 can include RTSS devices to detect a user's activities, motions, physical parameters, and the like, including but not limited to, a heart rate monitor, a body temperature probe, a conventional pedometer, an accelerometer and the like.

Alternatively, multifunctional sensors 14 which can perform all the aforementioned functions of RTSS may be attached or embedded in user monitoring device 10. In one embodiment, each sensor can be in communication and or connect electronically and/or RF to a telemetry module 16. A variety of different sensors 14 can be utilized, including but not limited to, an accelerometer based sensor, and pressure based sensors, voltage resistance sensor, a radio frequency sensor, and the like, as recited above.

As a non-limiting example, an accelerometer, well known to those skilled in the art, detects acceleration and thus user activity. The accelerometer provides a voltage output that is proportional to the detected acceleration. Accordingly, the accelerometer senses vibration. This voltage output provides an acceleration spectrum over time; and information about loft time can be ascertained by performing calculations on that spectrum. A microprocessor subsystem, such as disclosed in U.S. Pat. No. 8,352,211, incorporated herein by reference, stores the spectrum into memory and processes the spectrum information to determine activity. Other examples of suitable accelerometer sensors are disclosed in EP 2428774 A1, incorporated herein by reference. Suitable pressure sensors are disclosed in EP 1883798 B1, incorporated herein by reference. A suitable voltage resistance sensor is disclosed in EP 1883798 B1, incorporated herein by reference. A suitable radio frequency sensor is disclosed in EP 2052352 B1, incorporated herein by reference.

Figure 2:
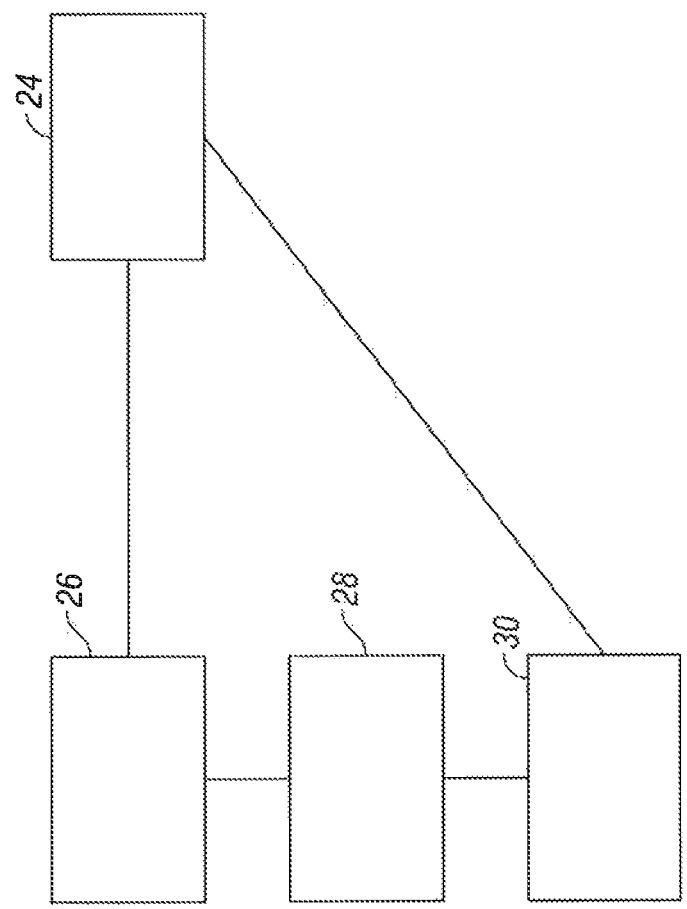
FIG. 2 illustrates one embodiment of electronics that can be included in the wearable device.

Referring to FIG. 2, in various embodiments, the user monitoring device 10, also known as the user monitoring device, can include a power source 24, such a battery that can be rechargeable. The battery can have a variety of different geometries that make it suitable to be positioned in a wearable device such as a wristband. It one embodiment, the battery 24 includes one or more curved exterior surfaces. The battery 24 can be put into a sleep state when not actively used in order to preserve power. A wake up feature allows the battery 24 and other electronics of the user monitoring device 10 to "sleep" during non-use or and is initiated into the "wake up" mode by certain predestinated events.

Figure 3:
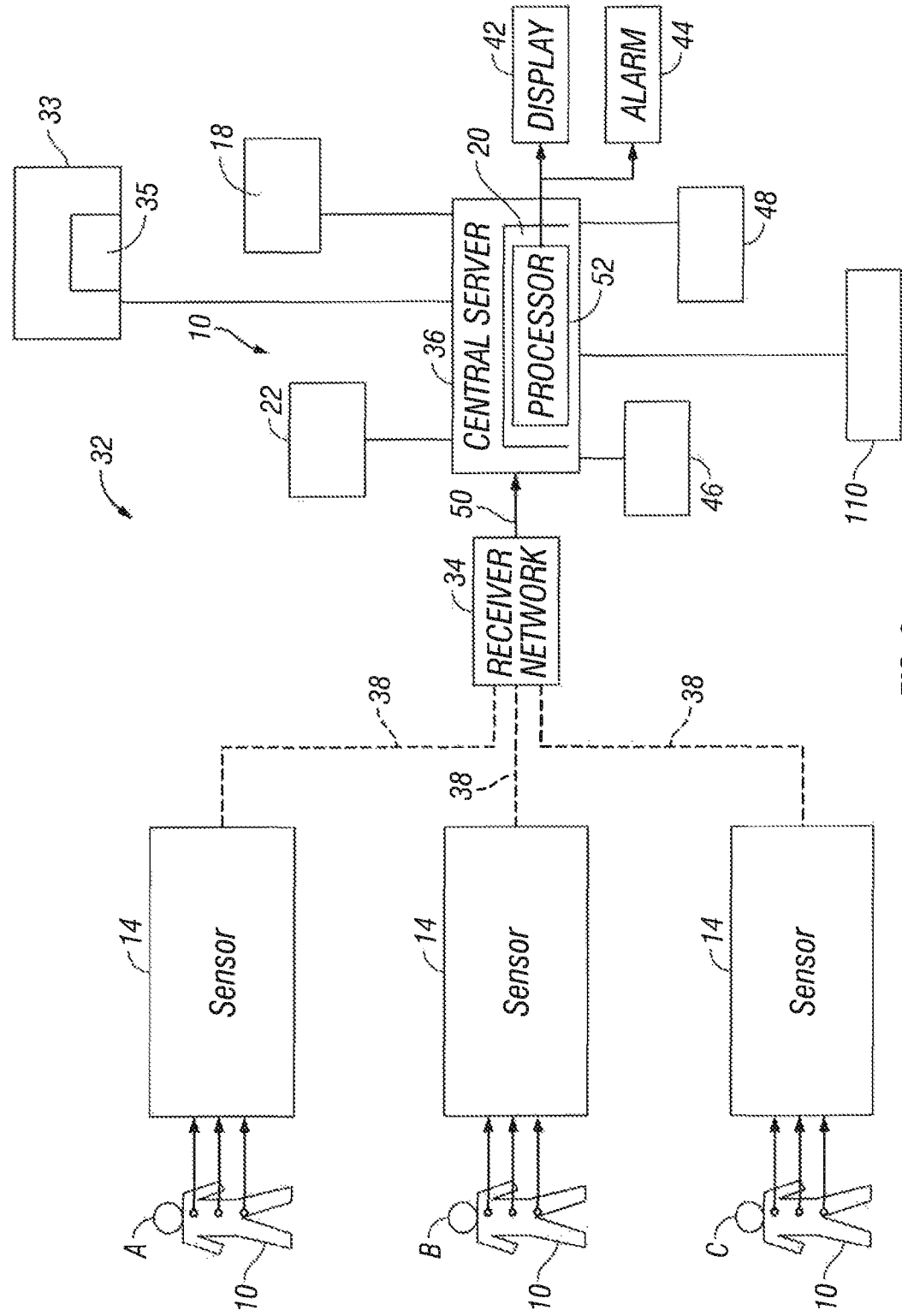
FIG. 3 illustrates one embodiment of a telemetry system of the present invention.

In one embodiment, as illustrated in FIG. 3, a telemetry system server 16 is coupled to a database 18. Each user monitoring device 10 is assigned its own unique identification, ID.

The data transmitted by the user monitoring device 10 sensors 14 and its ID may be coded by appending a seed to digital data bits. As illustrated in FIG. 3 central processor unit 20 (CPU) validates or rejects received upon detection of the seed string appended to the digital data bits. In the alternative, the digital data bits may be coded and decoded by applying a scrambling algorithm utilizing the seed. A programming device 22 may be configured to transmit data to a sensor 14, also known as a user monitoring device, utilizing a variety of alternative transmission means, including, for example, RF, IR, optical, and the like, or a magnetic loop/induction system.

In one embodiment, sensors 14 are configured to be shipped to users in a non-programmable mode with all programming already performed at the factory. A random seed may be communicated to the programming device 22 can a variety of different mechanisms, including but not limited to, via scanning a bar code, manual input, magnetic strip, random number generation, and the like.

Referring again to FIG. 2, in one embodiment, the user monitoring device 10 includes a control unit 26 that puts the user monitoring device 10 in a low power state. A monitoring system 28 can be included that remains active. The monitoring system 28 wakes up the electronics 30 in the user monitoring device 10 from a low power state. The control unit 26 can be notified of awaking of the other components by the monitoring system 28. The control unit 26 can set a status bit on the monitoring system 28 only when the battery 24 needs to be in a full power state. The control unit 26 then forces a power cycle.

Referring to FIG. 3, one embodiment of a telemetry system 32 is illustrated. The telemetry system 32 is in the communication with the sensors 14 and or user monitoring device 14 and ID of the user monitoring device 10 and can include one or more receivers 34, a central server 36 with the CPU 20. The telemetry system 32 can optionally include a display 42 and an alarm 44. The telemetry system 32 receives information from sensors 14 and or the monitoring device of a user's habits, activities, and the like, and then processes this information. Monitoring device 10 with its unique ID and sensors 14 is assigned to a specific user in order to track and/or monitor that user. For illustrative purposes assume that three users A, B AND C are being tracked and monitored by the telemetry system 32. It should, however, be appreciated that the telemetry system 32 may be implemented to track and/or monitor a much larger number of users.

In one embodiment of the present invention, radio frequency (RF) devices that are sensors 14 and/or chips may serve as the identifying devices. Each source, sensor 14, ID and the like can carry a fixed radio frequency chip encoded with identifying data which may be correlated to the individual participants, parts or objects.

Telemetry system 32 of the present invention may include a Real-Time Location System (RTLS) 46 and Real-Time Sensing System (RTSS) 48 with RF technology. The RF technology may include active and/or passive RFID sensors 14 and an RF wireless array system as a receiver 34. The RF technology in the RTLS 46 and RTSS 48 may include UWB technology (e.g., IEEE 802.15), WLAN technology (e.g., IEEE 802.11), SAW RFID positioning system technology, GPS technology, and the like.

The sensors 14 may communicate directly with each other and/or relay telemetry data directly to base receiving RF device(s) or base receivers 34. The base receivers 34 may forward the telemetry data to a base computer either through a direct link or through a Network System. Alternatively the telemetry data may be forwarded to end user devices, including but not limited to, laptops, mobile devices and the like, either directly or through a Network System. The comprehensive telemetry system 32 using RF technologies such as UWB, ZigBee, Wi-Fi, GPS data system can be utilized as described above.

The readers/antennae may be interconnected using a LAN, such as Ethernet to provide a Network System communication infrastructure for the computers and servers. Active and passive RFID sensors 14 may be employed. The active sensors 14 (RFID) may have a two-way communication function, which allows the base computer system to dynamically manage the sensors 14; vary update rates; send self-identification and telemetry data.

The active sensors 14 may employ dual-radio architecture. In one embodiment, active sensors 14 transmit radio pulses, which are used to determine precise two-dimensional or three-dimensional location and a conventional bi-directional radio, which is used as a control and telemetry channel with a sensor update rate.

The user monitoring device 10 gathers telemetry data, communicates that data to a base station, BLUETOOTH® enabled device, or smart phone and the like. From the base station, the user monitoring device 10 can receive firmware updates or via a BLUETOOTH® enabled device. The user monitoring device 10 can receive updates wirelessly. The base station can receive firmware updates from Network Systems, take telemetry data from the user monitoring device 10 and transfer it to Network Systems. Telemetry data received from the base station is analyzed by servers and presented to an end user. Any third party device can receive data from the user monitoring device 10 wirelessly and deliver information to the servers for processing.

In one embodiment, the user monitoring device 10 uses an accelerometer, gyroscope, GPS sensor, a BLUETOOTH® chip, and a heart rate monitor.

As a non-limiting example, for heart monitoring, the accelerometer, sensor 14, determines when to sample the sensors 14 and to improve the accuracy of the heart rate monitor. The gyroscope detects movement and orientation and the GPS sensor is used to determine location of the user. A BLUETOOTH® chip allows the device to connect wirelessly to other third party devices.

As a non-limiting example, a heart rate monitor 14 detects the user's heart rate in order to accurately determine the user's activity level, behavioral patterns and the like.

An Artificial Intelligence (AI) or Machine Learning-grade algorithms is used to identify the user's activities, behaviors, behaviors and perform analysis. Examples of AI algorithms include Classifiers, Expert systems, case based reasoning, Bayesian Network Systems, and Behavior based AI, Neural networks, Fuzzy systems, Evolutionary computation, and hybrid intelligent systems. A brief description of these algorithms is provided in Wikipedia and stated below.

Classifiers are functions that can be tuned according to examples. A wide range of classifiers are available, each with its strengths and weaknesses. The most widely used classifiers are neural networks, support vector machines, k-nearest neighbor algorithms, Gaussian mixture models, naive Bayes classifiers, and decision trees. Expert systems apply reasoning capabilities to reach a conclusion. An expert system can process large amounts of known information and provide conclusions based on them.

A case-based reasoning system stores a set of problems and answers in an organized data structure called cases. A case based reasoning system upon being presented with a problem finds a case in its knowledge base that is most closely related to the new problem and presents its solutions as an output with suitable modifications. A behavior based AI is a modular method of building AI systems by hand. Neural networks are trainable systems with very strong pattern recognition capabilities.

Fuzzy systems provide techniques for reasoning under uncertainty and have been widely used in modern industrial and consumer product control systems. An Evolutionary Computation applies biologically inspired concepts such as populations, mutation and survival of the fittest to generate increasingly better solutions to the problem. These methods most notably divide into evolutionary algorithms (e.g., genetic algorithms) and swarm intelligence (e.g., ant algorithms). Hybrid intelligent systems are any combinations of the above. It is understood that any other algorithm, AI or otherwise, may also be used. Examples of suitable algorithms that can be used with the embodiments of the present invention are disclosed in, EP 1371004 A4, EP 1367534 A2, US 20120226639 and US 20120225719, all incorporated fully herein by reference.

In various embodiments, the user monitoring device 10 has additional features. In one embodiment, the user monitoring device 10 changes color, via infrared LEDs, to accurately match the wearer's skin tone. This creates a seamless and more personal integration of technology into the user's daily life. In this embodiment, there is skin contact with the user monitoring device 10.

In another embodiment, the user monitoring device 10 remotely reminds and can be used to administer medications. As a non-limiting example, the user monitoring device 10 can inject adrenalin. In one embodiment, the user monitoring device 10 has sleep pattern recognition based on movement and heart rate.

In various embodiments, the user monitoring device 10 uses algorithms to determine activity type, behavioral patterns and user habits based on collected data.

In one embodiment, the user monitoring device 10 uses the accelerometer information to improve the heart rate monitor. As a non-limiting example, the user monitoring device 10 detects movement and speed. Addition of this data improves the accuracy of the heart rate monitor and corrects for any miscalculations in vibration, noise and skin color.

In one embodiment, velocity readouts and accelerometer data are used to measure when To Whom It May Concern: sample heart rate. For example, if the user monitoring device 10 registers zero velocity readout, the user is probably at rest or engaged in a passive activity. Thus, the user monitoring device 10 knows not to sample heart rate. This results in conversation of time, energy and data storage.

User activity, performance and action can be based on the acceleration and angular velocity of the user monitoring device 10. In one embodiment, the user monitoring device 10 has a feature where the user monitoring device 10 authorizes third party interaction based on hand gesture, on previous interactions or patterns of behavior. As a non-limiting example, if one purchases a coke every day for the last two weeks, the user monitoring device 10 can "orders" the person another one based on the prior history.

In one embodiment, the user monitoring device 10 features near-by user monitoring device 10 recognition that provides for other user monitoring device 10 devices to be recognized within a particular vicinity and are able to share and transfer data between them. The user monitoring device 10's data analysis and feedback can be based on current or previous sensor output. The user monitoring device 10 can alert the user when to charge the user monitoring device 10 and when it is the most convenient for the user.

In various embodiments, the feedback can be provided in graphical form, be contained in one or more web pages, transmitted to the monitoring device 10, displayed or communicated by audio mechanisms and the like.

In one embodiment, the user monitoring device 10 provides feedback via color change. An outer shell of the user monitoring device 10 can use visual feedback, including but not limited to pigment or color changes to indicate changes in user behavior or to prompt changes in user behavior. In one embodiment, the user monitoring device 10 is flexible in shape. As a non-limiting example, if the user puts the user monitoring device 10 over their hand it can expand or contract, morphing to change size and shape.

In one embodiment, the user monitoring device 10 can have a sync feature for multiple bands at the same time.

In one embodiment, the user monitoring device 10 has data transfer to an external device that can be included or not included in system 32. Patient monitoring device 10 could be a data leaching device. For example, the user can relay information to someone else's device (intermediary device) to access Network Systems connected device.

In one embodiment, the user monitoring device 10 can disable the recording of one or more sensors 14 based on location, acceleration (or lack thereof) and the like.

In one embodiment, the user monitoring device 10 detects different types of transportation and activity based on sensor data. In one embodiment, user monitoring device 10 can unlock doors or cars. The user can turn it on and off. As a non-limiting example, it can be turned off by having a capacitor switch on top and bottom and is placed in a way that one couldn't accidentally turn it off. As a non-limiting example, turning it off can be done by rotating the user monitoring device 10 once.

In one embodiment, the user monitoring device 10 recognizes the wearer based on biometric information, previous data, movement pattern, and the like. In one embodiment, the user monitoring device 10 detects a new user based on an inability to match to user/usage patterns.

For purposes of this application, a user's biometric information is one or more distinctive, measurable characteristics used to label and describe a user. In one embodiment, the biometric information includes but is not limited to, user physiological conditions or traits and user behavioral characteristics. In one embodiment, the biometric information is selected from at least one of, fingerprint, face recognition, DNA, palm print, hand geometry, iris recognition, retina, odor or scent, user gait, user blood pressure, user activity, user habit information and user health information.

In one embodiment of the present invention, the wearable device 10 includes wearable device structure 11 with one or more sensors 14 that detect or measure wearable device user information selected from of at least one of, a wearable device user's activities, behaviors and habit information, and a wearable device user's health. Communication and pathway systems are included. One or more processors 52 or a server compare received biometric information from the one or more sensors 14, perform a comparison, and determine a user profile stored in a database, including but not limited to database 18, that is internal or external to the wearable device 10.

In this embodiment, the wearable device 10 can be in communication with telemetry system 32. The biometric information is one or more distinctive, measurable characteristics used to label and describe a user. In one embodiment, the biometric information includes user physiological conditions or traits and user behavioral characteristics. In one embodiment, the biometric information is selected from at least one of, fingerprint, face recognition. DNA, palm print, hand geometry, iris recognition, retina, odor or scent, user gait, user blood pressure, user activity, user habit information, user health information. In one embodiment, the one or more processors 52 selects parameters associated with biometric data to use in authenticating the biometric data. In one embodiment, the database, which can be database 18, stores user biometric information for a variety of applications and purposes. In one embodiment, the applications and purposes are selected from at least one of, feature extraction, recording, and use of biometric parameters unrelated to secure storage of biometric parameters.

In one embodiment, a user's profile includes at least a portion of a user's biometric information. In one embodiment, the one or more processors 52 provide for authentication of the user and matches received biometric data with stored biometric data. In one embodiment, the one or more processors 52 perform at least one of, (i) extraction of unique features of the biometric data, (ii) enhances distinguishing aspects of the biometric data, and (iii) compresses the biometric data. The one or more processors 52 can compare received biometric data with records of a user's biometric data to identify a user. In one embodiment, in response to the received biometric information, biometric information in the database is added, dropped and/or changed.

Logic resources can be provided to determine a statistical closeness of the received biometric information with information in the database, which can be database 18.

In one embodiment, the telemetry system 32 provides an affirmative response when the received biometric information is within a selected range in comparison to the stored biometric data. Records of biometric data can be selected from the database 18 or another database, all being secured databases. Transmission of the biometric information from the wearable device 10 can be performed using a secure transport protocol.

In one embodiment, the wearable device 10 performs authentication of a user from the received biometric information using a comparison to determine whether the received biometric data sufficiently matches selected records of one of a plurality of users in the database. The performed authentication of the user can include a confidence range of a difference between a specified characteristic of the received biometric data with stored biometric data.

In one embodiment, the wearable device 10 encodes encoding enrollment biometric parameters of a user to produce an enrollment factor. The enrollment factor can be included in a database, including database 18. In one embodiment, the wearable device 10 acquires enrollment biometric data from a user. In one embodiment, the wearable device extracts the enrollment biometric parameters from the enrollment biometric data. In one embodiment, the wearable device authenticates biometric parameters to produce decoded biometric parameters.

As non-limiting examples, a variety of different sensors 14 can be used such as, an altimeter, blood oxygen recognition, heart rate from wrist via sonar, Doppler, based on sound wave and movement, based on pressure, and the like. A pressure sensor 14 can be placed on a circulatory vessel such as a vein to detect pulse.

With the user monitoring device 10 of the present invention, mechanical actions of the user can be triggered, recognized and evaluated.

As a non-limiting example, with multiple users and wearable devices 10, a separate user monitoring device 10 ID is assigned to each of the users A, B AND C, and thereafter the assigned transmitter/monitor 14 generates user activity data and/or user tracking data. For purposes of this disclosure, monitoring data is defined to include data acquired during the process of monitoring or evaluating a predefined characteristic. The user activity data tracks data from the sensors 14 is transferred to the receivers 34 via the wireless connections 38 represented by a dashed line.

A network of receivers 34 transfers the user activity and/or tracking data to system server 16 via connection 50. System server 16 includes a processor 52 configured to process the user data in a known manner. For example, the processor 52 may convert raw user data acquired by the sensors 14 into more conveniently readable data.

As a non-limiting example, the display 42 can be implemented to graphically convey user information from system server 16 in a conveniently readable manner. As a non-limiting example, the user may be a cardiac user with user monitoring data graphically conveyed as a conventional ECG plot comprising a sequence of P-waves, a QRS complexes and a T-waves. As another example, user tracking data may be graphically conveyed as an icon superimposed onto a map to indicate the user's relative location. Alarm 44 may be included in this embodiment.

In some embodiments, system 32 ID circuitry delivers a unique ID to the wearable device from database 18. BLUETOOTH® chips can be coupled with other wearable devices 10 in the area. This data is then stored, as more fully explained in the following paragraph. The unique ID can be utilized for a variety of different applications including but not limited to payments, social networking and the like.

The ID circuitry of system 32 can include a number of system/components: unique ID storage, communication system, which reads and transmits the unique ID from the unique ID storage, battery 24 or power system that provides power to enable communication with the user monitoring device 10, a pathway system to route signals to through the circuitry, a cluster that crunches information, and a control system, to orchestrate the communication between different systems. All of these systems can be implemented in hardware, software or a combination thereof. Continuing with the telemetry system 32, sensors 14 and sensing devices are disposed on wearable devices 10 worn by users. Data, such as movement, location, speed, acceleration, and the like, can be acquired, captured and provided to system 32.

System 32 and an associated Network System can include an identification reference, including user activity, performance and reference information for each individual sensor 14 and location.

The user activity, performance metrics, data and the like captured by system 32 can be recorded into standard relational databases SQL server, and/or other formats and can be exported in real-time.

In various embodiments, the user monitoring device 10 and/or system 32 are fully sealed and have inductively charges. All communication is done wirelessly.

In one embodiment, there are no electrical contacts, physical contacts or connections with the user monitoring device 10. The user monitoring device 10 is seamless. The telemetry system 32 can include a microprocessor with CPU 20, memory, interface electronics and conditioning electronics 33 configured to receive a signal from the sensors 14. In one embodiment, all or a portion of the conditioning electronics 33 are at the user monitoring device 10.

In one embodiment, the CPU 20 includes a processor 52, which can be a microprocessor, read only memory used to store instructions that the processor may fetch in executing its program, a random access memory (RAM) used by the processor 52 to store information and a master clock. The microprocessor is controlled by the master clock that provides a master timing signal used to sequence the microprocessor 52 through its internal states in its execution of each processed instruction. In one embodiment, the microprocessor 52, and especially the CPU 20, is a low power device, such as CMOS, as is the necessary logic used to implement the processor design. The telemetry system 32 can store information about the user's activity in memory.

This memory may be external to the CPU 20 but can reside in the RAM. The memory may be nonvolatile such as battery backed RAM or electrically erasable programmable read only memory (EEPROM). Signals from the sensors 14 can be in communication with conditioning electronics 33 that with a filter 35, with scale and can determine the presence of certain conditions. This conditioning essentially cleans the signal up for processing by CPU 20 and in some cases preprocesses the information. These signals are then passed to interface electronics, which converts the analog voltage or currents to binary ones and zeroes understood by the CPU 20. The telemetry system 32 can also provide for intelligence in the signal processing, such as achieved by the CPU 20 in evaluating historical data.

In one embodiment, the actions of the user wearing the user monitoring device 10 with the unique ID can be used for different activities and can have different classifications at system 32.

The classification can be in response to the user's location, where the user spends it time, with which the user spends its time, determination of working relationships, family relationships, social relationships, and the like. These last few determinations can be based on the time of day, the types of interactions, comparisons of the amount of time with others, the time of day, a frequency of contact with others, the type of contact with others, the location and type of place where the user is at, and the like. These results are stored in database 18.

In one embodiment, the user wearing the user monitoring device 10 can access this information from any place where data is presented to the user, including but not limited to mobile devices, the WEB, applications program identifiers, and the like.

As a non-limiting example, the user monitoring device 10 communicates with a base station at system 32. The user monitoring device 10 can intelligently switch between data transfer and charging based on sensor readout. The user monitoring device 10 can represent data based on connected devices.

In one embodiment, the user monitoring device 10 has the capability of providing recommendations, popularity of locations or activities based on acquired data from the user.

In one embodiment, the user monitoring device 10 has the capability of introducing the user to other people or users based on their data and the user's data.

In one embodiment, the user monitoring device 10 can determine emotion of the user.

In one embodiment, the user monitoring device 10 uses incremental data transfer via BLUETOOTH® and the like. The user monitoring device 10 can transmit data through the inductive coupling for wireless charging. The user is also able to change the frequency of data transmission.

The user monitoring device 10 can engage in intelligent switching between incremental and full syncing of data based on available communication routes. As a non-limiting example, this can be via cellular Network Systems, WiFi, BLUETOOTH® and the like. In one embodiment, the user monitoring device 10 has data storage. As a non-limiting example, storage of telemetry data on user monitoring device 10 can be amounts up to about 16 mg.

In one embodiment, data transferred if it's in a selected proximity of a base station of system 32 or in proximity of an associated connected Network System. In one embodiment, the user monitoring device 10 has a dynamic change of data capture frequency. The user monitoring device 10 can be programmed to instantly change how often it samples any sensor 14 based upon the sensor data. Intelligent data sampling is based on sensor readout.

The user monitoring device 10 can receive firmware updates via a base station 110 of system 32. In one embodiment, the user monitoring device 10 presents analyzed data and feedback on a website. In one embodiment, the user monitoring device 10's software is based on unique human movement. The user monitoring device 10 is able to identify its wearer based on the unique patterns of movement, location check-ins and daily habits of the user.

In one embodiment, the application can be used on a mobile device, including but not limited to a smart phone and the like.

In one embodiment, a breakdown of recounting data that has been collecting is presented for analysis of that data. Observation or recommendations can be presented based on historical information and live information. The importance of the data can be based on past user behavior.

In one embodiment, the user monitoring device 10 has artificial intelligence. A wearable device processor 54 implements logic resources that exist on user monitoring device 10.

In one embodiment, user monitoring device 10 engages in the routing of user information to third parties based on predefined rules, based on system 32 analysis.

In one embodiment, user monitoring device 10 includes one or more processors 54 that implement intelligent algorithmic processing and transfer of information to third parties. Feedback can be provided to the end user that is based on visual, tactile, gesture information and the like.

Figure 4:
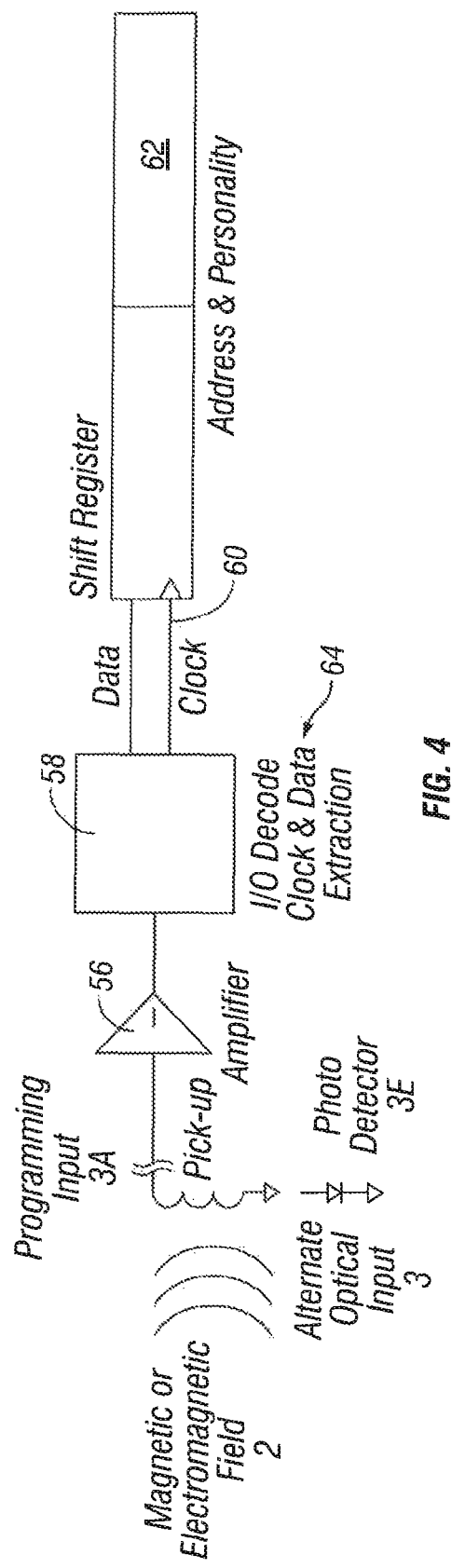
FIG. 4 is a diagram of the programming input schematic of the secure sensor/transmitter array of FIG. 7.

The ID can be sent from the user monitoring device 10 in a variety of different transmit modes, which may be provided as part of the firmware or software of an ID or sensor transmitter 14, and which may be utilized selectively during the operation of said sensor transmitter 14, may include 'burst' transmit modes, wherein a burst of data information is transmitted, or "parcel" transmit modes, wherein timed data packets of data, which may, as desired, comprise partial data strings, are transmitted, and, if desired, repeated during time intervals. Further, the sensors 14 may have programmed therein diagnostic routines or other test modes which assist during manufacture and use, providing the operator with operational status and verification information on said sensor/transmitter 14, as needed. Referring to FIG. 4, system 32 includes data base 18 which contains the desired transmitter, sensor, 14 personality data, as well as, the address/device ID bits for each user monitoring device 10.

In one embodiment, the initial programming of the user monitoring device 10 for the ID, as well as optionally other personal information of the user, is done securely, as unauthorized future alteration of same thereafter can be utilized as a means of violating system integrity.

In one embodiment, an inductive field coil is used for programming the sensors 14 and ID of user monitoring device 10.

As illustrated in FIG. 4, the user monitoring device 10 can include a sensor 14 with an output that be received by an amplifier 56 and decoded by an I/O decoder 58 to determine I/O logic levels, as well as, both clock and data information 60. Many such methods are commonly available including ratio encoding, Manchester encoding, Non-Return to Zero (NRZ) encoding, or the like; alternatively, a UART type approach can be used. Once so converted, clock and data signals containing the information bits are passed to a memory 62. Any of these connections provides a logical link from the system's database 18 to the sensor 14, ID of the user monitoring device 10, as shown in FIG. 5.

Figure 5:
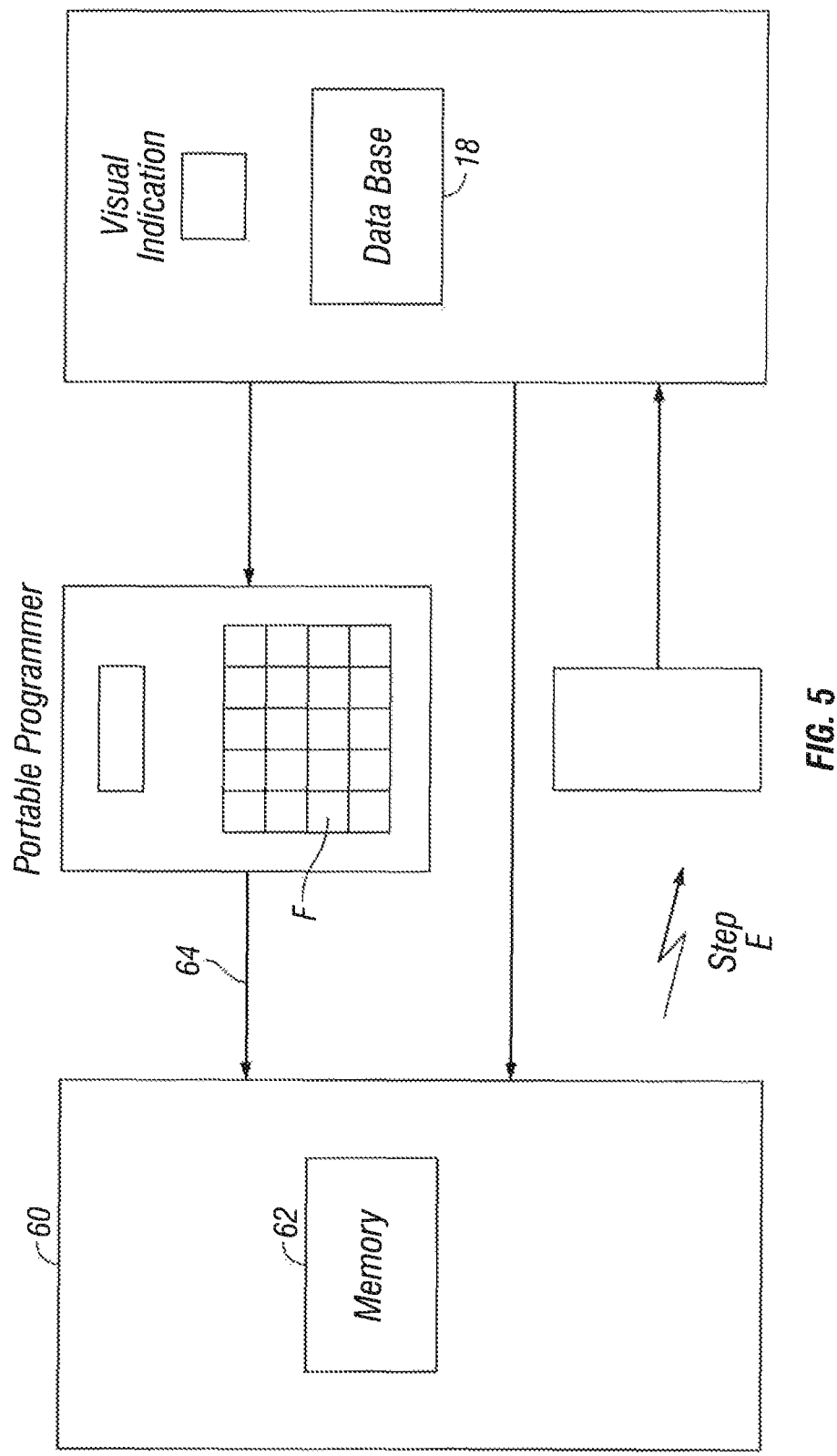
FIG. 5 is a block diagram of the system of programming the sensor/transmitter(s) comprising the secure sensor/transmitter array of FIG. 7.

In one embodiment, illustrated in FIG. 5, the system 32 chooses the necessary programmable sensor functions and stores them into database 18. In one embodiment, in order to insure that an unauthorized user cannot connect into and program user monitoring device 10 the following procedure may be used.

In one embodiment, the database 18 includes base individual information selected from at least one of, individual physiological information, information that is indicative of the individual's activities, data indicative of one or more contextual parameters of the individual and information regarding a degree to which an individual has followed a routine.

In one embodiment, the database 18 includes individual goals selected from at least one of, individual physiological information, information that is indicative of the individual's activities, data indicative of one or more contextual parameters of the individual and information regarding a degree to which an individual has followed a routine.

Both the sensor 14 and receiver 34 contain an identical, repeatable pseudo randomization algorithm in ROM or in ASIC logic.

Figure 6:
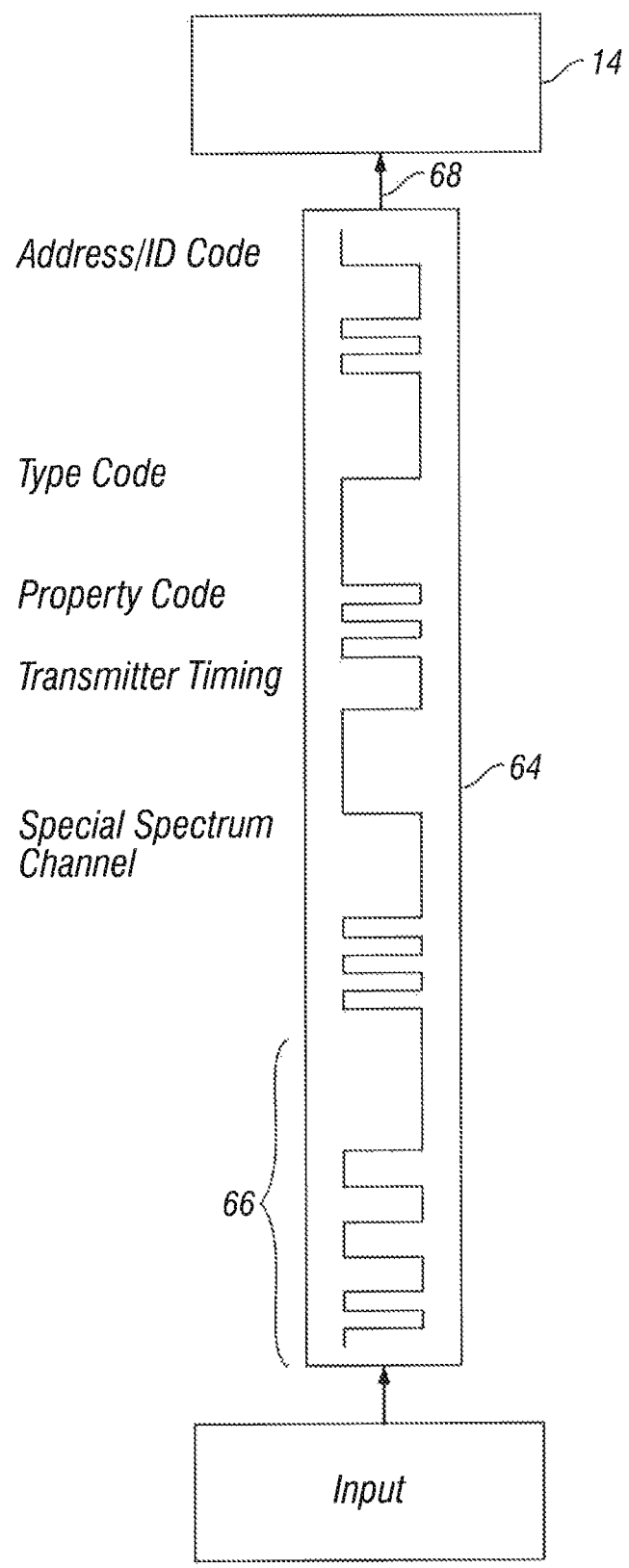
FIG. 6 is a block diagram of the jam command and security/randomization bits of the secure sensor/transmitter array of FIG. 7.

Referring to FIG. 6, the algorithm is applied to outgoing programming data 64 from system 32 and produces a number of security/randomization bits 66 that can be appended to the outgoing programming message or message 68 and sent to a sensor 14.

Figure 7:
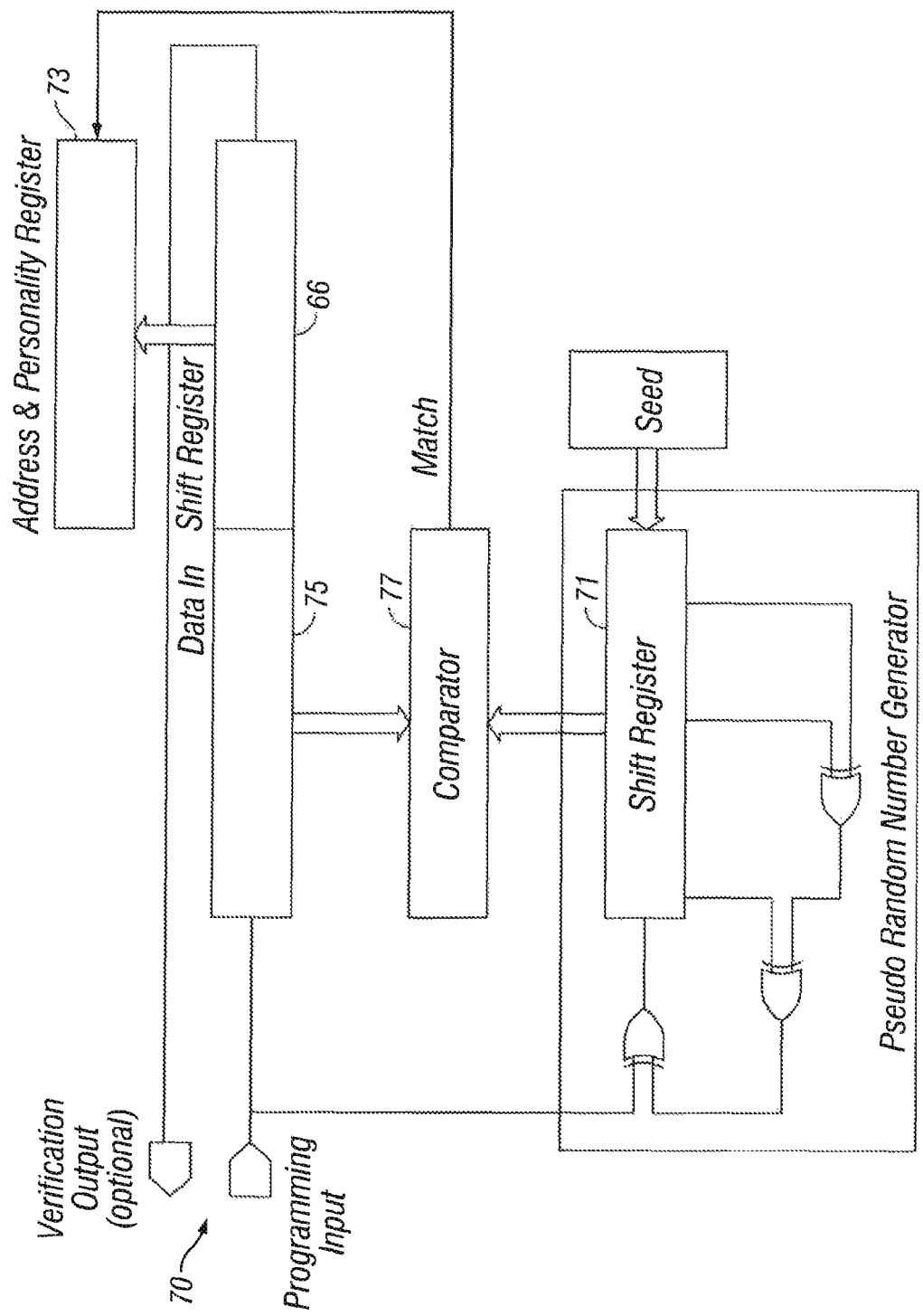
FIG. 7 is a logic circuit diagram of the sensor/transmitter programming input schematic in one embodiment of the present invention.

Referring to FIG. 7 the sensor 14 likewise applies this pseudo randomization algorithm as the security/randomization bits 66 to the outgoing programming data, now forming the incoming programming data 70 to sensor 14 and produces a several bit result in the shift register 71. The scrambling algorithm is devised such that a small difference in the programming bit stream causes a great difference in the pseudo randomization result. As a non-limiting example, the present invention can use a 16 bit polynomial to produce this pseudo randomization.

Optionally, in one embodiment, before a sensor 14 accepts this programming, stored in an address and personality register 73, both the pseudo random code, stored in data in a shift register 75 from system 32 and a sensor 14, in a shift register 71 must match via a comparator ID, 77, indicating unauthorized acceptance use. In addition to insuring authorized access, this process also insures that the data itself is correct. The longer the polynomial sequence used, the greater the security.

In one embodiment, spread spectrum or other RF transmission is used and can include programming to determine that the frequency or spread spectrum code is unique to the area. If a spread spectrum code, system code, or frequency channel is found to be occupied at a future time of use. Re-programming of the user monitoring device 10 is then done with a new, unused spread spectrum code or system code or frequency channel can be selected, or, in the alternative, CPU 20.

As illustrated in FIG. 5, step "E" would include, for example, the step of the sensor 14, inputting the programming message and saving a seed in memory 62; with the sensor 14 utilizing the seed to code digital data bits transmitted.

Figure 8:
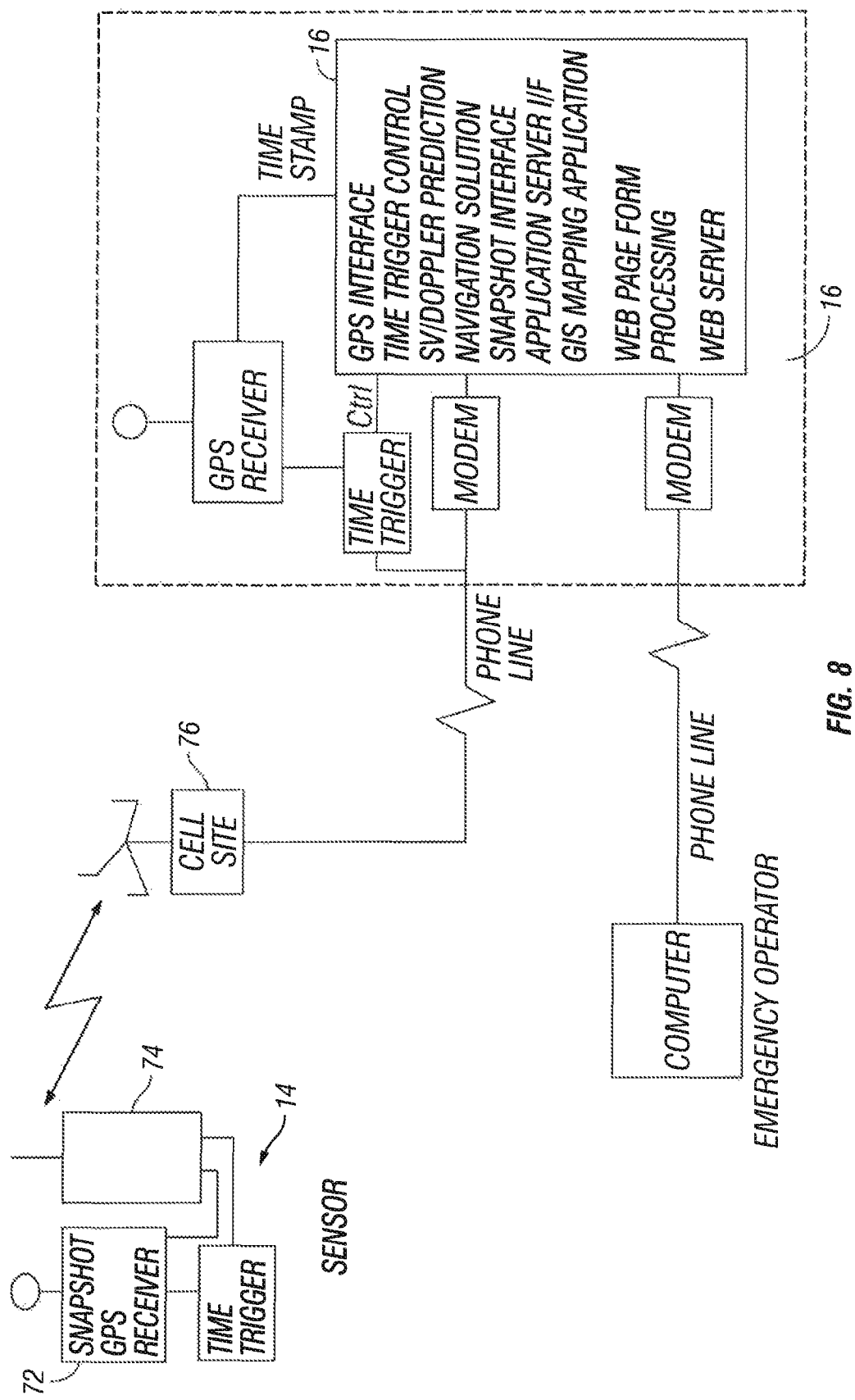
FIG. 8 is a block diagram of an embodiment of a computer implemented system for determining the location of a remote sensor utilizing the methods of the present invention.

As illustrated in FIG. 8, the location of a user monitoring device 10 with the ID and sensors 14 can be determined. As a non-limiting example, in one embodiment the user monitoring device 10 includes a sensor 14 that can provide a position signal having positioning data (e.g., raw GPD data or pseudo ranges) and the ID is transmitted from the user monitoring device 10 to system server 16. Server 16 receives the position signal and analyzes the signal to generate information representing the location of the user monitoring device 10. Server 16 transmits this location information to a client computer where the location of the user monitoring device 10, allowing a user to identify the location of the remote sensor 14.

In one embodiment, the position signal transmitted by the remote sensor 14 can also include an emergency code. For example, in the event of an emergency, such as a medical emergency or otherwise, a user may press a "panic button" that can be on the user monitoring device 10 or by use of a user's mobile device. Pressing the panic button may cause mobile device 74 to transmit an emergency signal to a cell site 76 where the emergency signal is relayed to server 16. In response, server 16 can transmit Doppler information regarding in-view satellites, a fix command and a time trigger signal to the user monitoring device 10.

When the location of the user monitoring device 10 has been determined, software running on server 16 configures server 16 such that a call or other signal is sent to a local emergency operator in the vicinity of remote sensor 14. When the call or signal is received at the emergency operator station, the location of remote sensor 14 is transmitted and displayed. In some cases, where separate panic buttons are available for identifying medical, police, fire or other types of emergencies, the nature of the emergency is also displayed for the emergency operator. Based on this information, the emergency operator can initiate an emergency response by providing the location of remote sensor 14 to the required emergency service (police, fire department, ambulance service, etc.). In other embodiments, instead of or in addition to a position report for the remote sensor 14, the emergency operator may also be provided with information which identifies an emergency response vehicle in close proximity to remote sensor 14.

Figure 9:
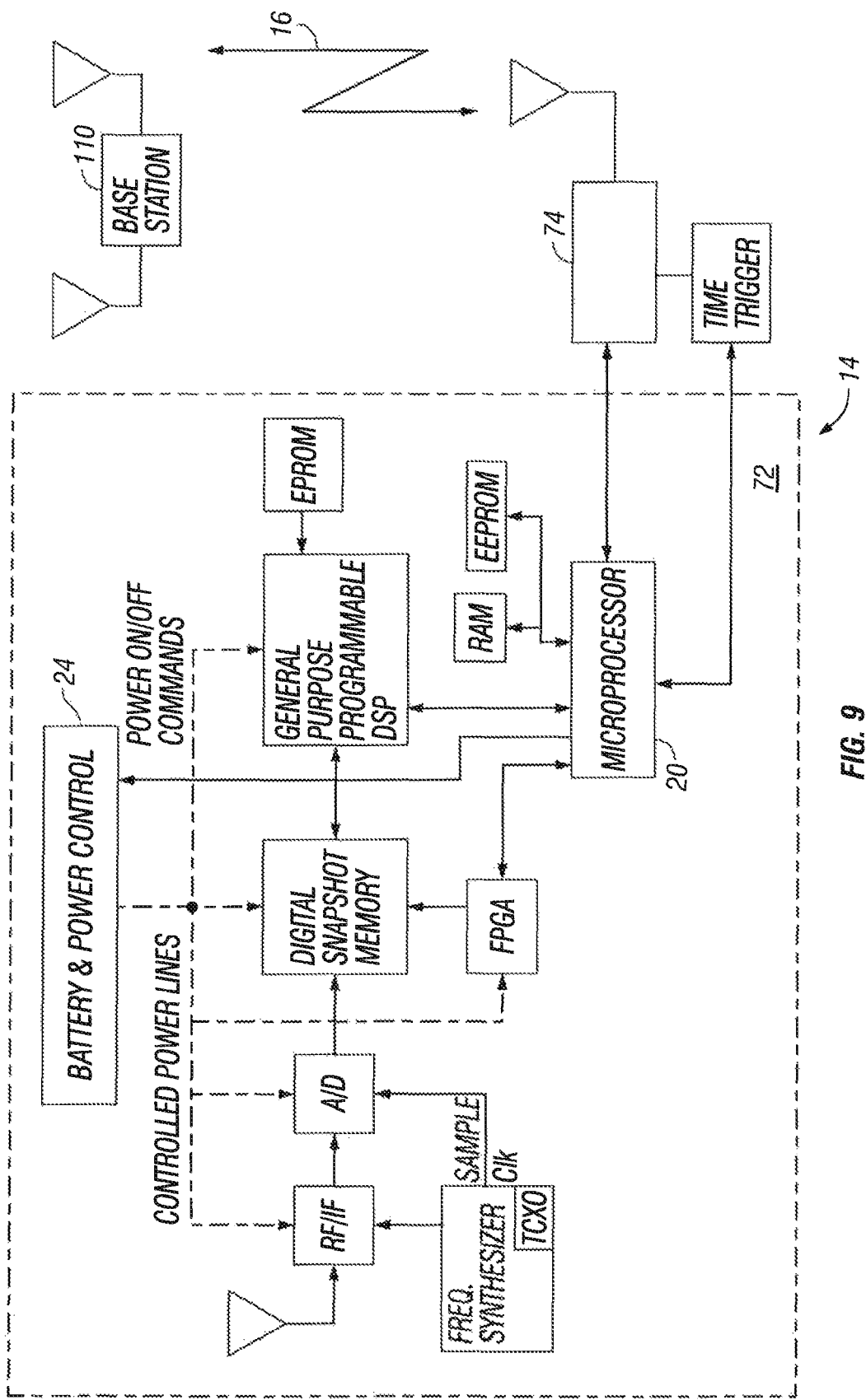
FIG. 9 is a block diagram illustrating one embodiment of a SNAPSHOT GPS receiver for use according to the present invention.

As illustrated in FIG. 9, a sensor 14 of the user monitoring device 10 can include a SNAPSHOT GPS receiver 72. As described above, sensor 14 uses information transmitted from separately located base station 110, mobile devices, computers, and other devices, to assist in determining the position of the remote sensor 14, as more fully disclosed in U.S. Pat. No. 6,661,372, incorporated herein by reference.

Figure 10:
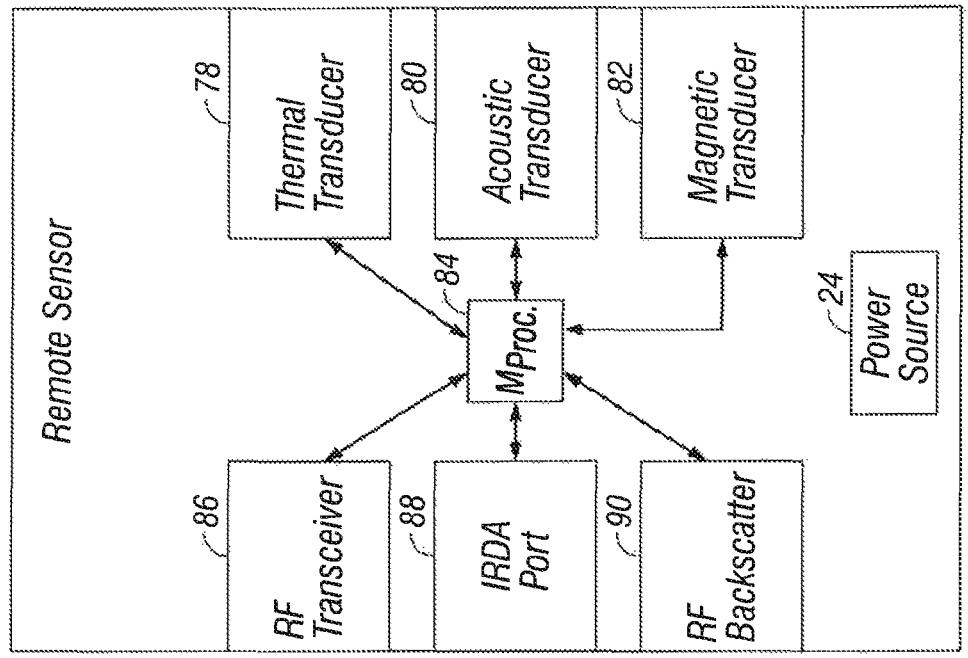
FIG. 10 is a block diagram of a remote sensor shown in communication with two different external communication devices.
Figure 10:
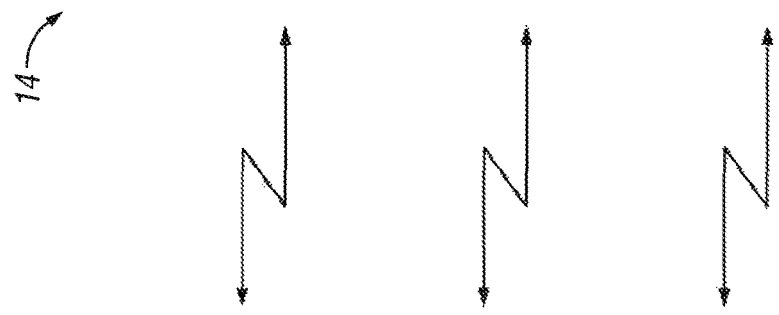
Figure 10:
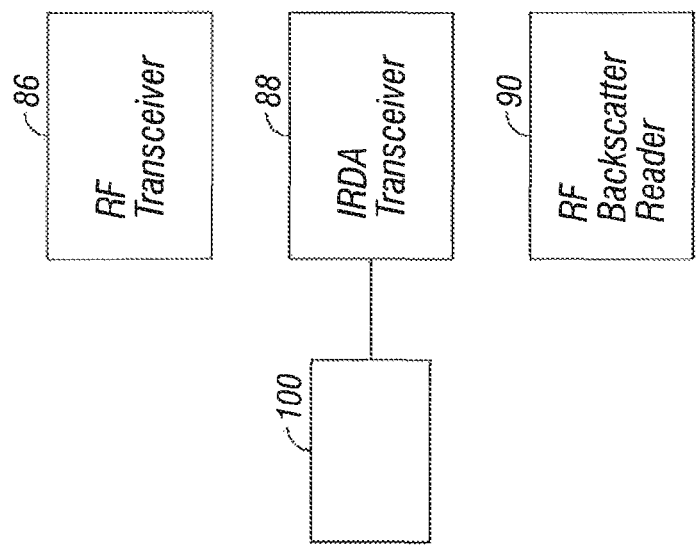

As non-limiting examples, and as illustrated in FIG. 10, the sensors 14 can be a thermal transducer 78, an acoustic transducer 80, and a magnetic transducer 82. It will be appreciated that the present invention is not limited to these transducers. The transducers 78, 80, and 82 in the user monitoring device 10 can communicate with a microprocessor 84 also located in the user monitoring device 10. The user monitoring device 10 can communicate with other devices via an RF transceiver 86, an IRDA transceiver 88, and/or an RF backscatter transceiver 90. Each of the components in the user monitoring device 10 receives power as necessary from the battery 24, which may include the rechargeable battery.

The acoustic transducer 80 may include a microphone, a low-pass filter, a gain amplifier, and a threshold comparator. The acoustic transducer 80 may include an omnidirectional microphone, although any other suitable acoustic transducer device would suffice. The microphone may be a surface mount MEMS device that has a frequency range of 100 Hz to 10 kHz. A single MCP602 operational amplifier is used on the acoustic sensor to amplify and low-pass filter the acoustic signal from the microphone. Another operational amplifier is used to generate a voltage reference used for single biasing and detection. The microphone output is biased to the midway point between the circuit supply voltage and ground to allow for both positive and negative signal swings. The biased signal is filtered with a second order low-pass Butterworth filter to remove upper frequency noise. It is then amplified with an adjustable gain that is controlled by a digital resistor potentiometer. This digital resistor operates on an I2C bus and is controlled by the microprocessor 84. Lastly, the amplified acoustic signal is threshold detected against a static voltage to detect sufficiently large acoustic signals. The digital output of the threshold detector is connected to the microprocessor 84 for processing.

The magnetic transducer 82 can include a magnetic sensor integrated circuit, a differential instrumentation amplifier, a low-pass filter, two gain amplifiers, and a threshold detector. The magnetic transducer 82 may include an NVE AA002-02 GMR (giant magneto resistive) field sensor, although any suitable magnetic sensor would suffice. This sensor has a saturation field of 15 Oe, a linear range of 0 to 10.5 Oe, and a sensitivity of 3 mV/V/Oe. Two MCP602 CMOS operational amplifiers are used on the magnetic sensor to amplify and low-pass filter the analog output signal. An INA122UA instrumentation amplifier is used as a difference amplifier for the differential output from the magnetic sensor. The magnetic sensor IC can be based on Spintronics technology. Its output includes a differential voltage pair proportional to the detected magnetic field. The differential voltage pair is amplified and converted to a single voltage by the instrumentation amplifier. The AC-coupled signal is then amplified and filtered with a low-pass filter to remove upper frequency noise and boost the low-voltage signal output. The signal is amplified a second time by an adjustable gain controlled by a digital resistor similar to the acoustic sensor. Lastly, the amplified magnetic signal is threshold detected against a static voltage, to detect sufficiently large changes in magnetic fields. The digital output of the threshold detector can be connected to the microprocessor 84 for processing.

A DS1803E-010 digitally controlled 10 kOhm variable resistor can be used in both the acoustic and magnetic sensor circuits. It is used to adjust the gain of one gain stage in each circuit. The digital resistor is controlled through an I2C interface. A LMV393IPWR comparator is also used in both the magnetic and acoustic sensor circuits for determining when a sufficiently strong sensor signal has been detected. It compares the analog sensor signal against the voltage reference and its output is tied to the microprocessor 84 for data collection.

The thermal transducer 78 may include a Burr Brown TMP 100NA/250 12-bit digital temperature sensor, although any suitable thermal sensor would suffice. The digital temperature sensor has an operating range of −55 to +120 degree. C, an accuracy of 0.5 degree C. and a maximum resolution of 0.0625 degree C.

Even though it is a 12-bit sensor, suitable results are achieved with only 9-bit conversions with only the 8 most significant bits used. The sensor has an I2C interface and is normally kept in sleep mode for low power operation. When directed by the microprocessor 84, the thermal transducer can perform a 9-bit temperature conversion in 75 milliseconds.

The RF transceiver 86 may include an RF Monolithic DR3000 transceiver, although any suitable transceiver or separate transmitter and receiver 34 would suffice. This transceiver 86 allows for both digital transmission and reception. The transceiver 86 can have an operating frequency of 916.5 MHz and is capable of baud rates between 2.4 kbps and 19.2 kbps. It can use OOK modulation and has an output power of 0.75 mW. It also can use digital inputs and outputs for direct connection with the microprocessor 84. The transceiver 86 can use an antenna 92 (FIG. 11) that may include a 17 mil thick plain steel electric guitar G-string cut to a length of 8.18 cm. It is used in a monopole over ground configuration and can require a matching circuit of one inductor and one capacitor. Alternatively, Frequency Shift Keying (FSK), Quadrature Phase Shift Keying (QPSK), or any other suitable modulation scheme may be utilized.

The IRDA transceiver 88 may include a Sharp GP2W0110YPS infrared transceiver, although any suitable IRDA compliant infrared transceiver would suffice. This transceiver 88 can be IRDA v1.2 compliant and in one embodiment has an operating range of 0.7 meters. In one embodiment, it is capable of 115.2 kbps data speeds.

The RF backscatter transmission device 90 may include circuitry available from Alien Technology (of Morgan Hill, Calif.) for receiving and transmitting signals via RF backscatter. Battery 24 may be a 3.6 volt ½ AA lithium battery with a capacity of 1.2 amp hours. The battery 24 can be a power source 24 that can include a Texas Instruments TPS76930DBVT voltage regulator to regulate the output signal to 3 volts and with a maximum current of 100 mA. The voltage regulator can include a LDO.

The RF backscatter transceiver 86 in the user monitoring device 10 communicates with an RF backscatter reader 94 such as a class 3 reader from Alien Technology. The reader 94 transmits data to the backscatter transceiver 90 of the user monitoring device 10 by broadcasting encoded RF pulses and receives data back from the transceiver 86 by continually broadcasting RF energy to the sensor 10 and monitoring the modulated RF reflections from the sensor 10.

The RF backscatter transceiver 90 can include a printed circuit board (PCB) patch antenna for RF reception, and RF modulation, a Schotky diode detector circuit, a comparator circuit for signal decoding, and a logic circuit for wake-up. The logic circuit monitors the incoming data, and when an appropriate wake-up pattern is detected, it triggers the microprocessor 84 so that data reception can begin. In one embodiment, the reader 94 has an operating frequency between 2402 MHz and 2480 MHz, and uses frequency hopping in this band to reduce noise interference. A modulation method used by the reader 94 can be On-Off Keying (OOK). In one embodiment, the transmission power is 1 watt. The operation of the reader 94 may be controlled by an external computer (not shown) as directed by Labview software via a RS-232 serial link.

The RF transceiver 86 can communicate with an external RF transceiver 96 such as a DR3000 transceiver from Radio Monolithics, Inc. In one embodiment, it operates at 916.5 MHz, uses OOK modulation, has a communication range of 100 meters line of sight, and a baud rate of 19.2 kbps. The active RF antenna 92 can be a quarter-wavelength monopole made from a guitar G-string and appropriate matching circuitry. Two control lines from the microprocessor 84 can be used to select the mode of operation, choosing from transmit, receive, and sleep. The active RF receiver 34 consumes the most power in receive mode compared to the other two communication links.

FIG. 6 shows the relative positioning and shape of the active RF antenna 92 and the RF backscatter antenna 98.

The IRDA transceiver 88 of the user monitoring device 10 can communicate with an external IRDA transceiver 100 that may be identical to the IRDA transceiver 88. Alternatively, the IRDA transceiver 100 can be one such as is provided in most personal digital assistants (PDA) as well as many other consumer devices. The IRDA communication link follows the standard IRDA signal and coding protocol and is modeled after a standard UART interface. In one embodiment, the IRDA transceiver 88 is capable of data speeds less than 115.2 kbps, and may only have a range of 0.7 meters for transmission. One advantage of the IRDA communication link is that it does not require any of the RF spectrums for operation, but it typically does require line-of-sight communication.

When any one of the transceivers 86, 88 and 90 on the user monitoring device 10 detect the beginning of valid data on their respective communication link, all other transceivers are disabled, thereby preventing the corruption of incoming data with the noise or partial data packets on the other communication links. However, if the data on the active transceiver proves to be erroneous, the other transceivers will be re-enabled if appropriate to allow normal operation to continue. If the data received by the active transceiver is valid, however, the other transceivers will remain disabled for several hundred milliseconds longer in the high probability that the next data packet will be transmitted on the same communication link. If, after this extended delay, no additional packets are received, then the other transceivers will be re-enabled as appropriate.

In one embodiment, the active RF protocol has no wake-up or synchronization packets, and the packets sent to and from the sensor are identical. In one embodiment, the format of an active RF packet is shown in FIG. 16. It can include a preamble to reset and spin-up the state machine of the RF receiver 34 and to properly bias the receiver's 34 data slicer/threshold detector for optimum noise rejection and signal regeneration, two framing bits to indicate the beginning and end of the data bytes, and the data bytes themselves.

Figure 12:
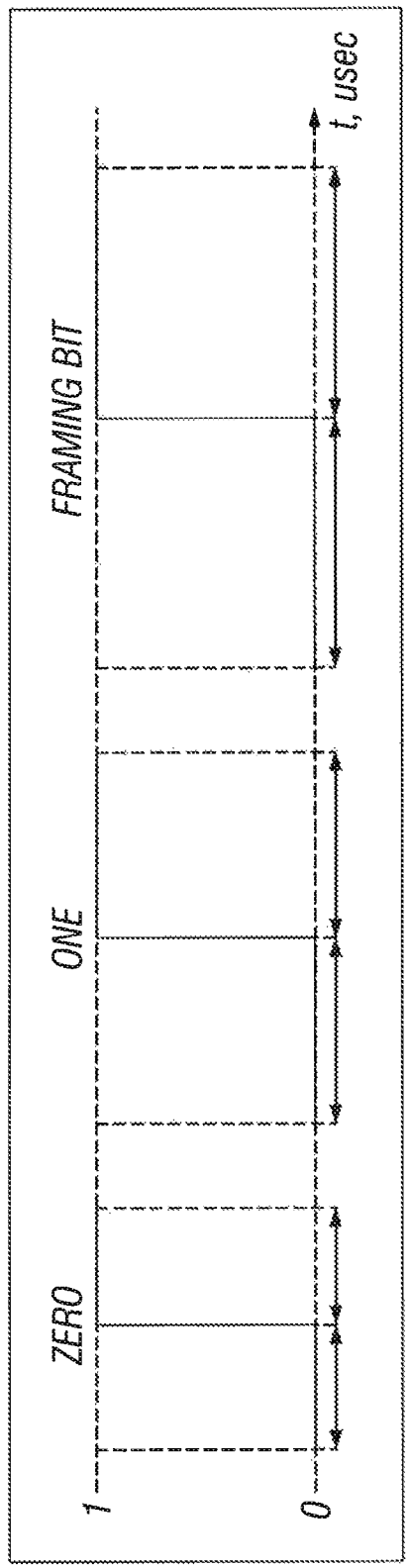
FIG. 12 is a diagram of the encoding scheme for the symbols in the active RF protocol.

Furthermore, the encoding scheme for the three symbols is shown in FIG. 12. The entire packet is DC balanced to maintain an optimal level on the data slicer/threshold detector and the receiver 34. Data is sent most significant bit first.

Figure 13:
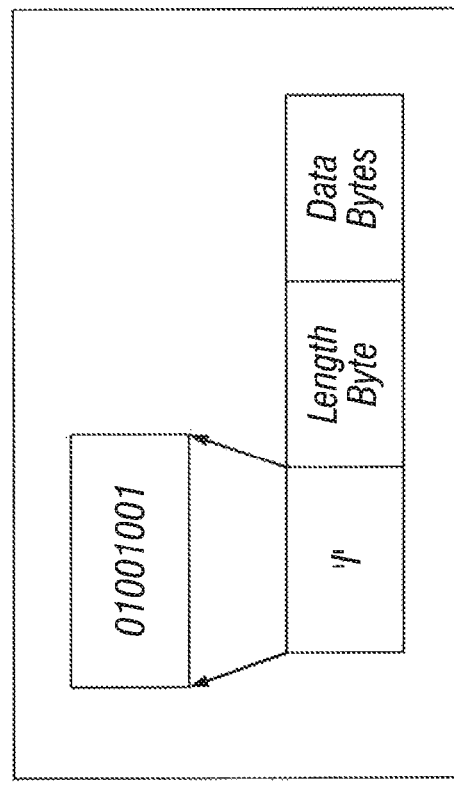
FIG. 13 is a diagram of the packet structure in the IRDA protocol.
Figure 14:
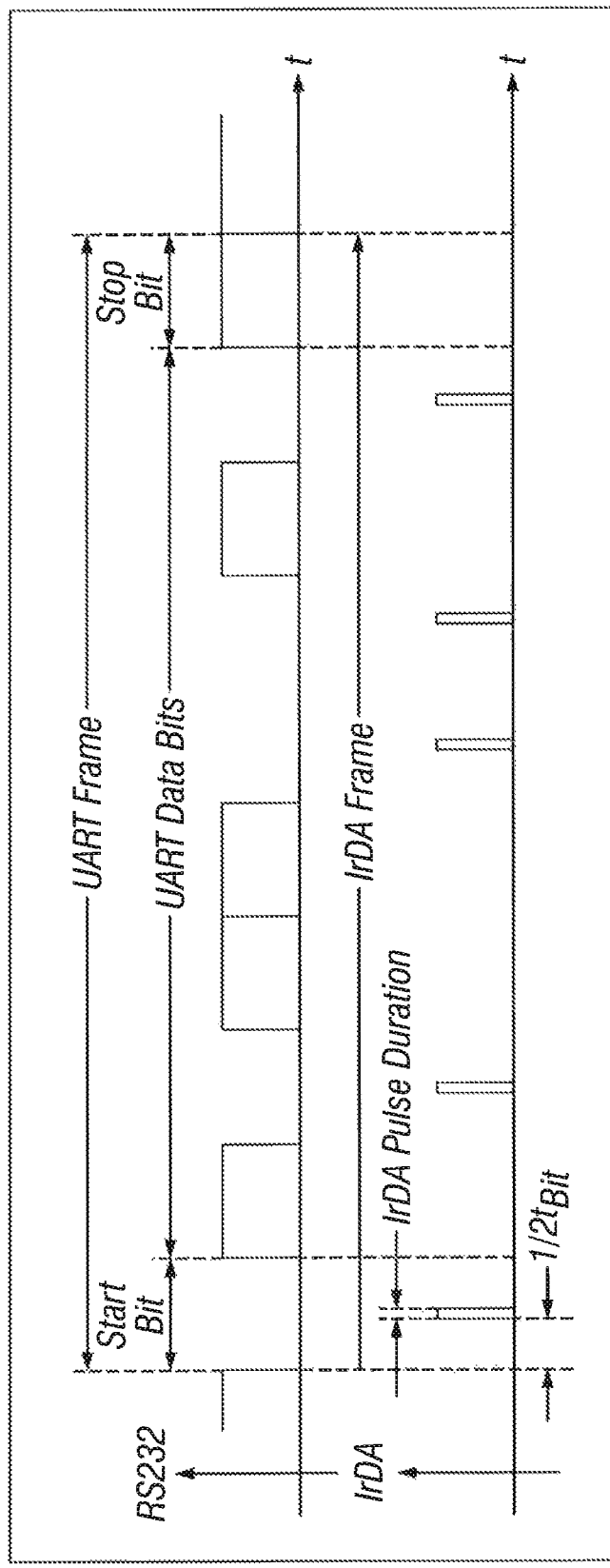
FIG. 14 is a diagram of the encoding scheme in the IRDA protocol.

The IRDA communication link can follow the standard IRDA protocol for bit encoding and UART protocol for byte transmission. Packets transmitted on the IRDA link can contain no preamble or framing bits, but they do have a header that contains two bytes. The first byte is an ASCII "I" which denotes the beginning of a valid IRDA packet. The second byte equals the number of preceding bytes in the packet. This value is used by the receiver 34 to determine when the entire packet has been received and processing of information can begin. The packet structure is shown in FIG. 13 and the IRDA/UART encoding scheme is shown in FIG. 14.

The data bytes contained in a packet transmitted to the sensor 10 through any of the communication links conform to a packet format. The CMD section of a packet is a single byte that identifies the type of packet being sent. The CMD byte appears above the beginning and end of the packet and the two must be identical. The reason for including the redundant byte is to further eliminate the chance of a packet's CMD identifier being corrupted at the receiver 34, even if the CHECKSUM is correct.

The PAYLOAD contains all of the data that must be sent to, or returned from, the sensor. The PAYLOAD is broken down into individual bytes with the overall number of bytes and their content dependent on the type of packet being sent.

The CHECKSUM is a 16-bit CRC that is performed on all bytes in the data packet excluding the end CMD byte in packets generated by the external device. The CHECKSUM is sent most significant byte first.

The transceivers 86, 88 and 90 may be required to communicate over a greater distance than do the components described herein. Upgrading these components to be suitable for longer distance transmission is considered to be within the spirit of this invention. The type of transducer is not limited to the specific transducer types described herein. In addition, the logic described herein for arbitrating between which communication device to use to communicate with the outside world and which sensor data to provide at what time is but one possible approach to arbitration logic within such a remote sensor 10.

Figure 15:
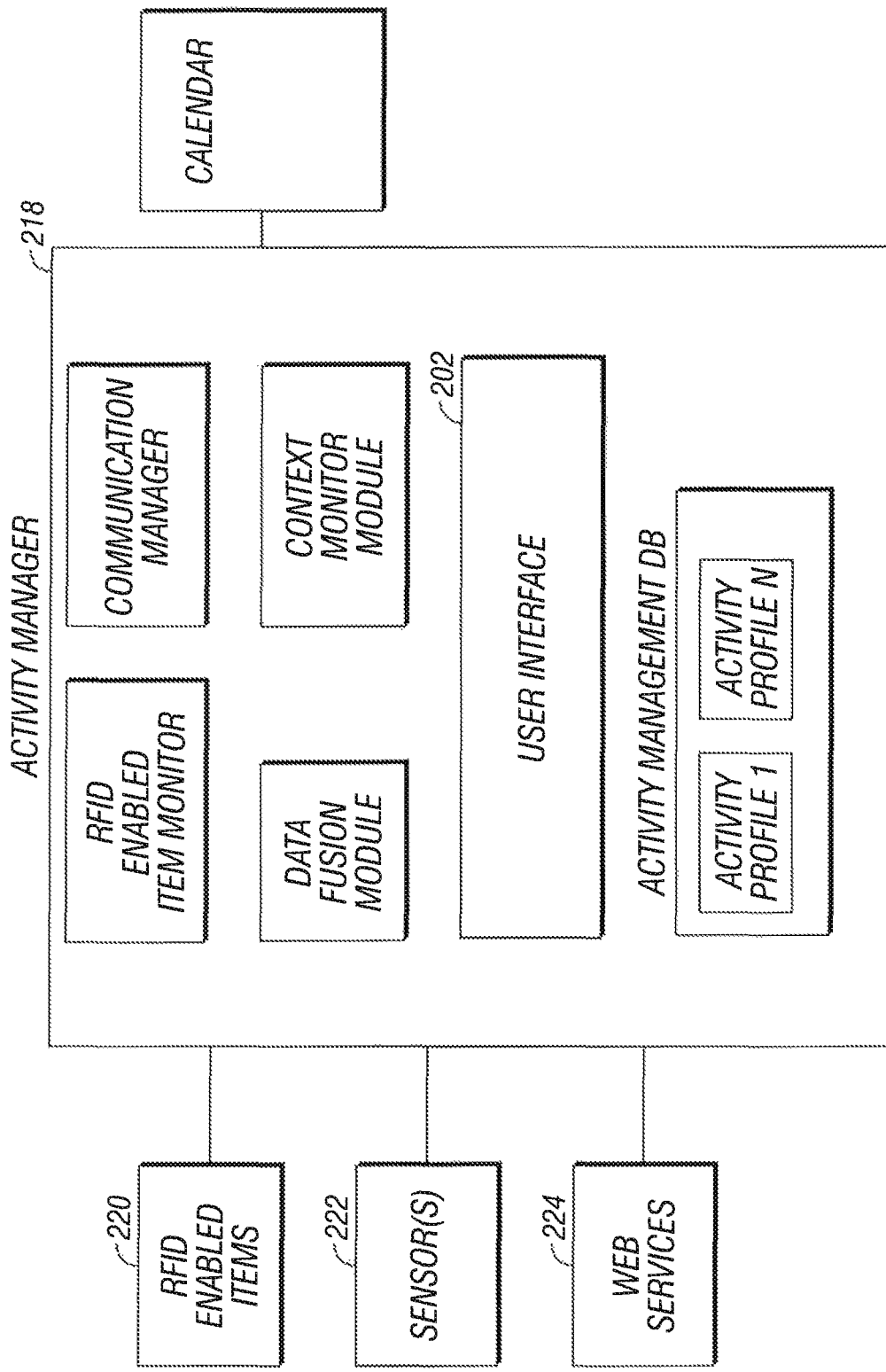
FIG. 15 illustrates one embodiment of an activity manager that is included in the monitoring device, the telemetry system or as a standalone device.

In one embodiment, illustrated in FIG. 15, an activity manager 218 is provided that is used for managing lifestyle activities of the user. Activity manager 218 can be a stand-alone device, or as part of the telemetry system 32 or monitoring device 10. The dynamic activity manager 218 can associate one or more contexts such as time, location, and the like to an activity entered by a user. The dynamic activity manager 218 also manages an activity and any device or item associated with the activity.

In one embodiment, the activity manager 218 communicates with the monitoring device 10 and provides information analysis of the individual information received from the monitoring device, the individual information selected from at least one of, individual physiological information, information that is indicative of the individual's activities, data indicative of one or more contextual parameters of the individual and monitoring a degree to which an individual has followed a routine. The routine includes at least one of individual, nutrition, activity level, mind centering, sleep, daily activities, exercise and the like.

In one embodiment, one or more of sensors 14 can be a lifestyle sensor. For example, the sensor 14 can be a physiological sensor such as a heart rate sensor, body temperature sensor, caloric sensor, or the like. Another example of a sensor is a pedometer. It should be noted that any sensor or device capable of taking measurements is applicable to the present invention. These sensors can be embedded, for example, in clothing and/shoes or can be stand-alone items. One specific example of these types of sensors is a sensor that is embedded in running shoes. As a user walks or runs, the sensor 14 monitors various functions such as speed, stride length, body functions (heart rate, temperatures, hydration, and the like), and the like.

This information can then be relayed back to the dynamic activity manager 218 if desired. A web service 124 can be any type of service subscribed to by the user over the Internet. For example, a user can be subscribed to a weather service that is used by the dynamic activity manager 218 when monitoring an activity such as running. The dynamic activity manager 218, identifier enable items, including but not limited to RFID enabled items 220, sensors 14, and Network System 224 are discussed in greater detail below.

The dynamic activity manager 218 provides management for managing user lifestyle activities and can be included as part of the telemetry system 32. In one embodiment, the activity manager 218 is in communication to a user interface 202, which can be at the monitoring device 10, for allowing a user to enter information associated with an activity that the user wants managed and/or monitored. As a non-limiting example, FIG. 17 shows one example of the user interface 202 being displayed on the monitoring device 14. It will be appreciated the sensors can generate this information and communicate it with telemetry system. It should be noted that some fields can be automatically populated based on user activity entry, activity history, rules, or the like.

In one embodiment, a name entry field 302 can be used that allows the user to enter the name of an existing activity or the field 302 can be a drop down box including existing activities. In another embodiment, the monitoring device 10 or the telemetry system 32 can perform this activity and function.

FIG. 16 show that a user has entered the activity of "running". Therefore, the user is configuring the activity manager 218 to manage and monitor a running activity. The user interface 202 can also include an activity description field 304, which allows a user to enter a description of the activity. A date entry field 306 is also included on the user interface 202. The date field 306 allows a user to enter the date or dates when the activity is to occur. A time start field 308 and an end time field 310 are also provided in the user interface 202. The start time field 308 indicates when the activity begins and the end time field 310 indicates when the activity ends.

A user may also want the activity manager 218 to track specific items associated with the activity. For example, with respect to the running activity, a user may want to have her running shoes and headphones tracked to ensure that she has these items when she begins the activity. This information can be entered in the items to be tracked field 312. The tracking process is discussed in further detail below. The user may also want to use specific sensors 14 during the activity such as sensors 14 in the running shoes and a heart rate monitor. The sensor IDs or names can be added into the sensor field 314. A user can also configure the sensor parameters that she wants used during the activity. Alternatively, the sensor parameters can be transparent to a user. For example, the parameters can be pre-populated based on success of data collection of prior activity history. This information is entered in a sensor parameter field 316. In addition to having items tracked and sensors 14 monitored during the activity, the user may want to associate a web service with the activity.

For example, a user may want to associate a weather service with the running activity so that the activity manager 218 can automatically and dynamically adjust settings on the sensors 14; determine to track different items; and the like. For example, the activity manager 218 can monitor the web service to determine if the weather is sunny, cloudy, raining, or the like. If the weather is sunny, the activity manager may determine that a first pair of running shoes, sun glasses, and the like need to be tracked. On the other hand, if the weather is raining, the activity manager 218 can determine not to track sunglasses and to track a second pair of running shoes. It should be noted that the term "tracked" as used throughout this discussion refers to use of the ID of the monitoring device.

Alternatively, a user can setup rules that allow a web service to perform a function based on contexts. For example, if the weather is rainy, a user can have a rule setup that has a web service make a reservation at an indoor track. FIG. 16 also shows a web sensor rule(s) entry field 320. The web service field 320 allows a user to enter various rules associated with Network Systems. For example, a user can setup a web service via the web service rules field 320 to reserve a running track if the temperature outside is less than 60° F. or if it is raining.

It should also be noted that the user interface of FIG. 16 is only one example of a user interface applicable to the present invention. One or more fields may be added or deleted. For example, the user interface 218 can also provide a mechanism to a user for reviewing all entered activities, deleting activities, and the like. It should also be noted that the user interface 202 can also reside on an information processing system coupled to the monitoring device 14. For example, the activity manager 218 can have software loaded on a personal computer that allows the user to enter the above information or to interact with the activity manger 218. The activity manager 218 can then sync with database 18 to update its data. In yet another embodiment, a user can enter information directly at an identifier enabled item 220 or a sensor 14. For example, a sensor 14 can include a user interface with a calendar. Any information entered here can then be synced with the activity manager 216. Any configuration parameters such as a heart rate baseline, stride length, and the like are then communicated to the activity manager 218.

Referring again to FIG. 15, the information received from a user, for example, via the user interface 202 can also be provided to a calendar 204 residing within the monitoring device 14. Alternatively, information from the calendar 204 can also be extracted by the activity manager 218. For example, if the activity manager 218 determines that a user has entered a new activity in the calendar 204, the activity manager 218 can prompt the user to determine if the user wants the activity manager 218 to monitor and manage that activity. Although shown residing outside of the activity manager 218, the activity manager 218 can include an internal calendar for monitoring lifestyle activities. In other words, the monitoring device 14 can include a calendar and the activity manager 218 can also include an internal calendar used in conjunction with the wireless device calendar 204.

Figure 17A:
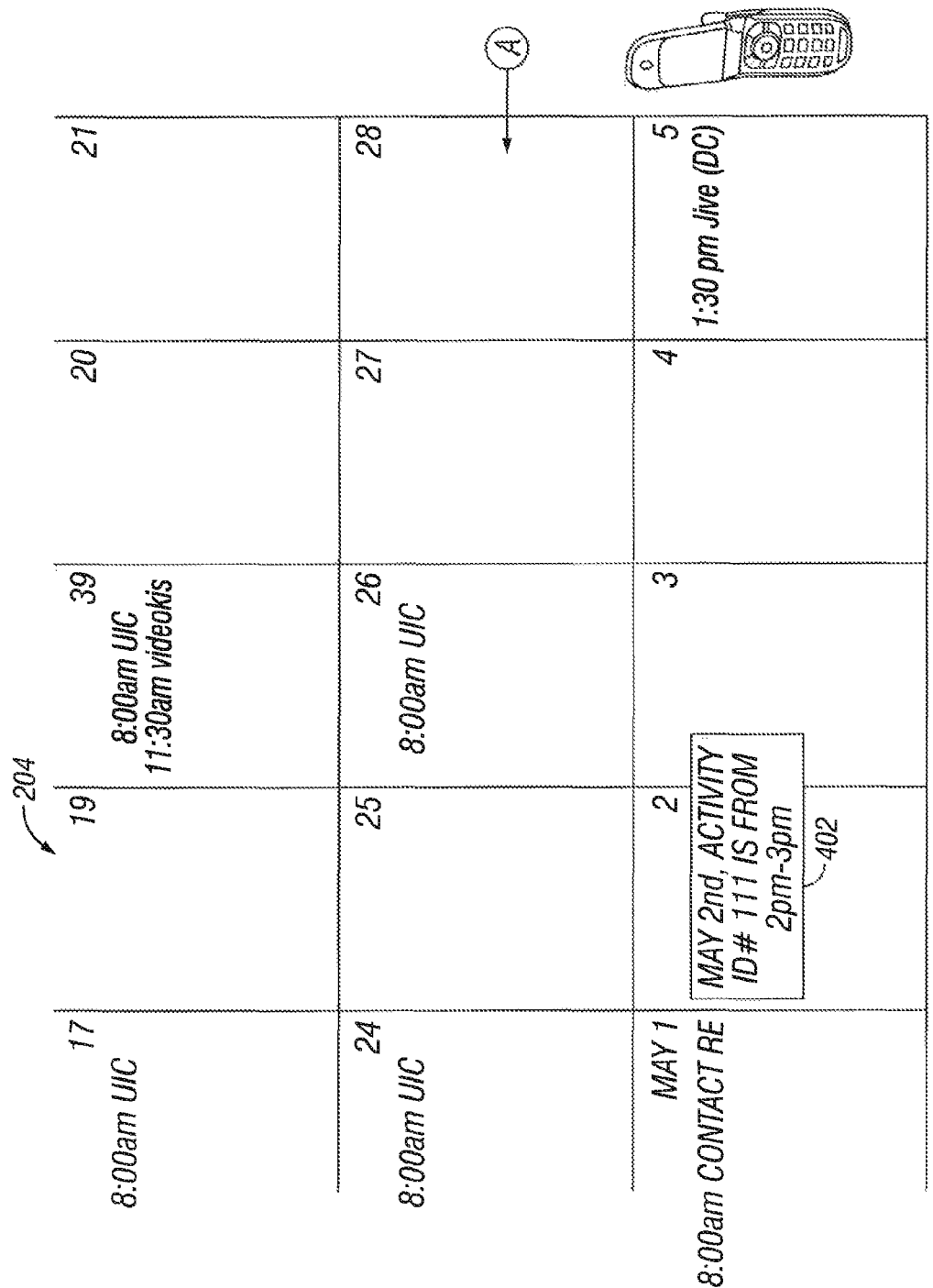
FIGS. 17(a) and (b) illustrate an exemplary user interface for an activity management application according to an embodiment of the present invention.
Figure 18:
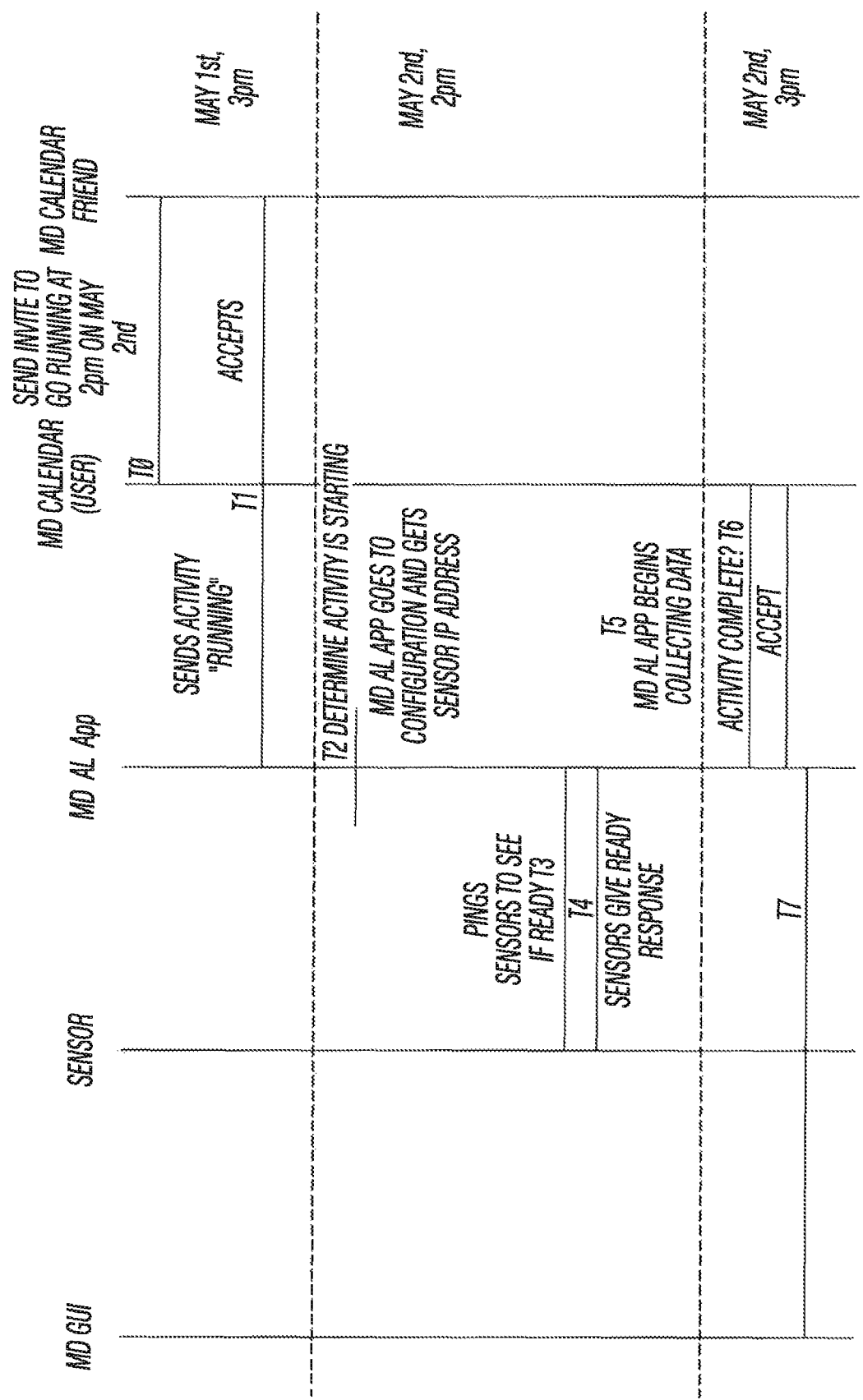
FIG. 18 is a timing diagram illustrating one example of monitoring an activity based on one or more contexts according to an embodiment of the present invention.

Based upon the received activity information, the activity manager 218 creates activity profiles 210, 212 that are stored in an activity management database 208. FIGS. 17(a) and (b) shows an example of an activity profile 210 for a variety of activities. Although FIGS. 17(a) and (b) show a single table that includes multiple activities, each activity can be stored within a separate activity profile. FIG. 18 also shows a calendar 204 comprising calendar events associated with an activity. The activity profile 210 includes various information associated with an activity such as a name 404 of an activity, an activity ID 406, a sensor or device name 408 associated with the activity, an identifier/device IP address 410 if available, data configuration 412 for the sensor/device and the like.

Also, FIGS. 17(*a*) and (*b*) show Network Systems 414 and web service rules 416 associated with a web service. For example, a web service A is associated with the "running" activity. A web service rule is associated with the web service A that indicates that if the temperature outside is less than 60° F. then reserve an indoor track. As can be seen, the activity profile associates a sensor/device context with activity. The sensor/device context indicates what sensors 14/devices or associated with the activity and their current configurations.

In the example of FIG. 18, the information within the activity profile 210 is independent of a time context or location context associated with an activity. In one embodiment, the calendar 204 associates a time context with and activity and an optional location context. For example, FIG. 18 shows a calendar event 402 set for May 2nd with a "running" activity from 2 p.m. to 3 p.m. The calendar 204 can also show the location of the activity such as "Millennium Park". Therefore, the "running" activity has a time context and a location context associated with it. The information within the activity profile 210 can be used by the activity manager 218 regardless of the time and location contexts.

For example, if the user has defined a "running" activity on two different days at two different times and at two different locations, the activity manager 218 can still refer to the "running" activity profile and use the information included therein for the two instances of the "running" activity. Therefore, the activity manger 218 monitors both the calendar 402 and the activity management database 208. However, the activity profiles 210 can also include time and location contexts as well. In this example, a separate activity profile is stored in the activity management database for each instance of an activity.

Returning now to FIG. 16, the activity manager 218 also includes a context monitoring module 210. In one embodiment, the content monitoring module 210 allows the activity manager to determine whether an activity is about to start, has started, or has ended and either monitor for identifier enabled items 220 and/or initialize sensors 14 associated with the activity. For example, the context monitoring module 210 monitors context such as time, location, device, and the like. The context monitoring module 210 can monitor the calendar 204, GPS, or information entered by the user to determine the current and/or location of the wireless device. The activity manager 218 can compare activity profiles and/or calendar events with the determined time and/or location to determine whether an activity is starting, ending, or the like.

In one embodiment, the dynamic activity manager 218 is communicatively coupled to a GPS module 246 and a display 244. The GPS module can be used by the dynamic activity manager 218 to determine the location of the monitoring device 14. The display 244 can be used for, among other things, to display data/information, visual alerts to a user.

As discussed above, the activity manager 218 manages and monitors identifier, enabled items 220, sensors 14, and Network Systems 224 associated with a user activity, identifier enabled items 220 can be any item that is coupled to an identifier or other communication tag. The activity manager 218 monitors identifier enabled items 220 via an identifier enabled item monitor 206, herein referred to as the "identifier monitor" 206. The identifier monitor 206, in one embodiment, can be an identifier transceiver embedded with monitoring software or can be a separate monitoring software module coupled to an identifier transceiver.

The identifier monitor 206 can be configured by the user to automatically start monitoring for items associated with an activity or to continuously monitor for identifier enabled items 220. For example, when the activity manager determines, based on a time context and/or a location context associated with an activity, that it is time for an activity to start, the activity manager 218 can begin monitoring for associated identifier enabled items 220. For example, if the activity manager 218 determines that the running activity is about to begin, the identifier monitor analyzes the activity profile 210 to determine what items are needed for the activity. The identifier monitor 206 then determines if items such as running shoes and heart beat monitor are present. In other words, the identifier monitor 206 determines if an identifier signal from the running shoes and the heartbeat monitor has been detected. The activity manager 218 can then visually, audibly, and/or tactilely notify the user of the presence or non-presence of the items 220.

Based on the activity profiles 210, calendar 204, and/or an internal clock the activity manager 218 can determine that the user has not left for work, to go running, or whatever the activity may be. For example, a user can have a calendar entry or an activity defined for "leave for work", which begins at 8:00 a.m. Therefore, if the time is 7:30 a.m. the activity manager 218 can determine that the user has not left for work. In another example, a user can have an activity defined for "running". The activity manager 218 can detect that the user has left the house, entered his/her car or the like either by passing an identifier sensor at a door or via GPS and analyzes the activity profiles 210 accordingly.

The activity manager 218, based on activity profiles and/or calendar events determines that the user is going straight from work to her running activity. Therefore, the activity manager 218 monitors for the items associated with the running activity. The activity manager 218 then notifies the user if these items have been protected.

In addition to monitoring for associated identifier enabled items 220 when an activity is to begin, the activity manager 218 manages sensors 14 associated with the activity. For example, when an activity is about to begin, the activity manager 218 analyzes the activity profile 210 associated with the activity and identifies the sensors 14 associated with the activity. If the sensor 14 has not been initialized, the activity manager 218 initializes the sensor 14 using the configuration parameters in the activity profile 210. For example, the sensors 14 and the monitoring device 14 can communicate via a communication manager 212 within the activity manager 218. The sensors 14 and the monitoring device 14 can communicate using a wireless connection such as BLUETOOTH®, Zigbee, or the like. In one embodiment, the dynamic activity manager also includes a data fusion module 214 for performing data fusion with respect to health and fitness information monitored by the sensors 14.

FIG. 18 shows a timing diagram for one example of initializing a sensor 14 based on the activity manager 218 detecting the start of an activity. In the example of FIG. 18, a user has a "running" activity defined on the user's monitoring device 14 and wants to invite a friend to the activity. At time T0 the activity manager 218 sends an invite associated with the "running" activity to another wireless device. The invite includes the time context, e.g., May 2nd at 2 p.m., and can include an optional location context. At time T1 the invitee wireless device sends an acceptance message to user's monitoring device 14. At time T2, the activity manager 218 determines that the time is 2:00 p.m. and queries the activity management database 208 to identify the sensors 14 associated with the "running" activity. The activity manager 218 also obtains the IP address of the sensor(s) 14. The IP address is used by the communication manager 212 to communicate with the sensor 14. In one example, the sensors 14 associated with the running activity are a sensor within running shoes that measures average speed, distance traveled, and the like. Another sensor can be a hear rate monitor worn in the wrist or an audio headset of the user.

At time T3 the activity manager 218 pings the sensors 14 to determine if they have been initialized. If the sensors 14 have not been initialized the activity manager 218 identifies that configurations parameters of the sensor from the activity profile 210 and initializes the sensors 14 accordingly. The sensors 14, at time T4, send a ready response to the activity manager 218. At time T5 the activity manager 218 begins collecting data from the sensors 14. The activity manager 218, at time T6, determines that the activity has completed. At time T7, the activity manager 218 displays collected data from the sensors 14 to the user via the user interface 202.

In another embodiment, a user can configure the activity manager 218 to only collect specific data from a sensor 14 or not all data. Also, the activity manager 218 does not have to communicate with a sensor 14 during an activity. For example, a user may have forgotten the monitoring device 10 at her house. The application manager 218 determines that an activity is starting, but sensors 14 are not in the vicinity. When sensors 14 come back into range with the monitoring device 14, e.g., the user comes home from running, the activity manager 218 queries the sensor 14 for the data collected during the activity. In one example, the sensors 14 collect data continuously and in another example the sensor 14 only collects data during scheduled activities. For example, a user's watch may have a biometric sensor that collects data throughout the day. However, the user may only be concerned with plotting data during athletic activities such as bicycling. Therefore, the activity manager 218 can query the sensor 14 for data only collected during a bicycling activity. In the above embodiments, the sensors include memory for storing data.

As illustrated in FIG. 15, the activity manager 218 can also monitor and manage Network Systems 224 associated with an activity. For example, a user can define rules associated with Network Systems 124 that are to be applied to the activity manager 218 with respect to an activity. One example is where a user subscribes to a weather service. The user can define a rule that states if the weather is rainy during the time period associated with an activity, then delay any monitoring or managing for that activity for 1 hour. Another rule can state to delay any managing or monitoring until a user prompt is received. The activity manager 218 can query the web service 124 at the start or prior to an activity starting to obtain the required information.

The activity manager 218 can also make dynamic decisions for when to monitor and/or manage an activity. For example, a user has an activity defined for "pick up drycleaning" at 3:00 p.m. However, at 12:00 p.m. the user runs errands and is approaching the dry cleaners. The activity manager 218 can detect the location of the user via GPS and determines that the user is near the dry cleaners. The activity manager then determines that the user needs to pick up the dry cleaning and prompts the user to pick up the dry cleaning even though the time is prior to the 3:00 p.m. scheduled pickup time.

Figure 19:
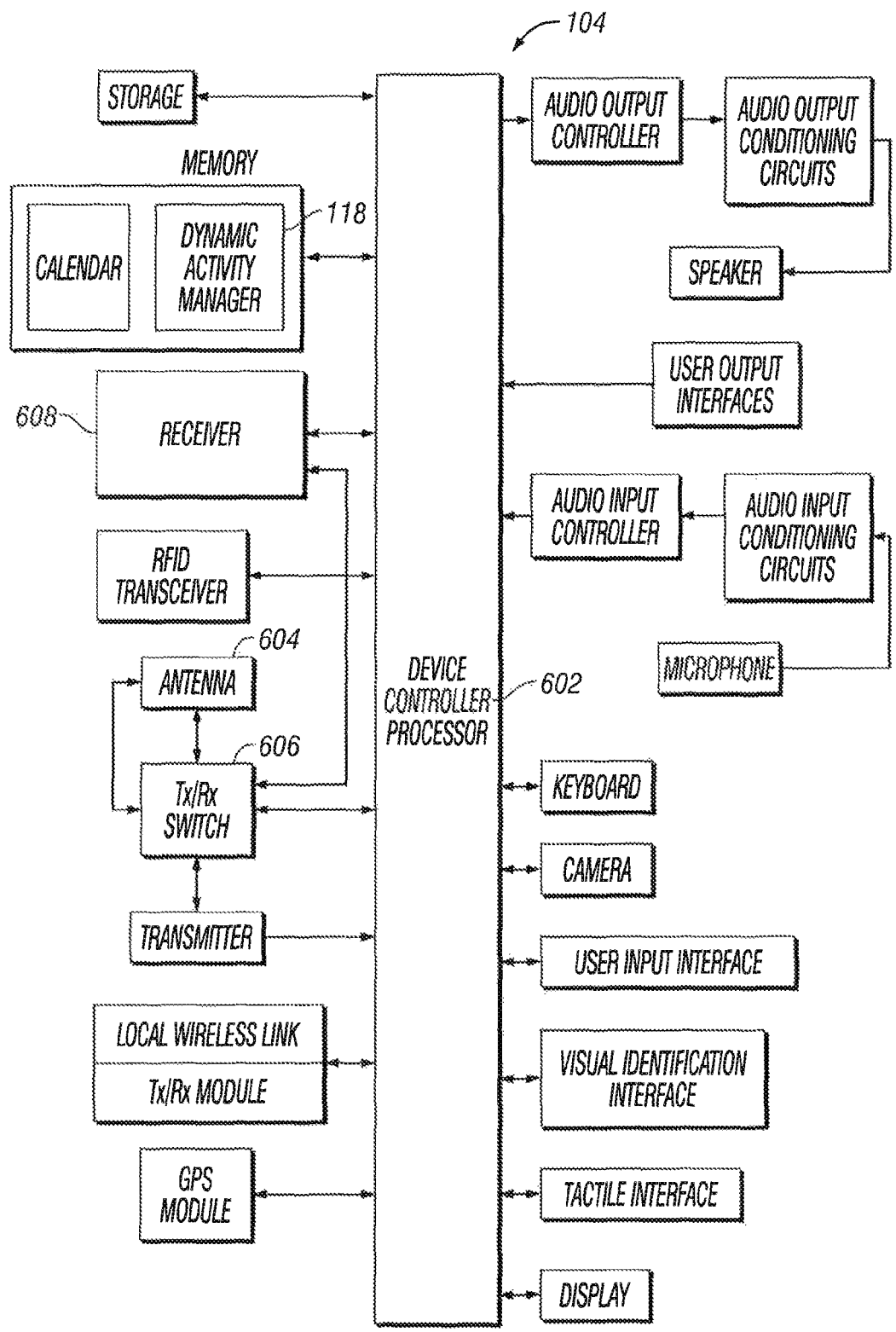
FIG. 19 is a block diagram illustrating one embodiment of a monitoring device of the present invention.

FIG. 19 is a block diagram illustrating a detailed view of the wireless device 104 according to an embodiment of the present invention. The wireless device 104 operates under the control of a device controller/processor 602, that controls the sending and receiving of wireless communication signals. In receive mode, the device controller 602 electrically couples an antenna 604 through a transmit/receive switch 606 to a receiver 608. The receiver 608 decodes the received signals and provides those decoded signals to the device controller 602.

Figure 20:
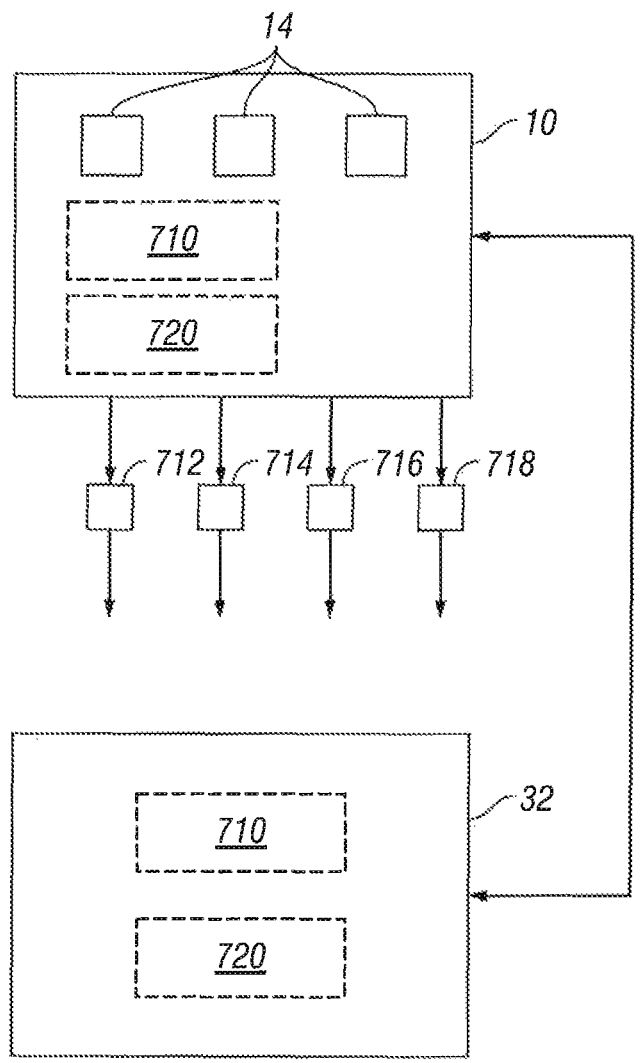
FIG. 20 illustrates an embodiment of the present invention that includes a feedback system or subsystem.

Referring now to FIG. 20, monitoring device 10 and/or telemetry system 32 can include a feedback system or subsystem 710 coupled to processor 20 and/or 34 to communicate feedback data back to the monitoring device 10. In one embodiment, the feedback system or subsystem 710 can generate and communicate closed-loop control data ("CCD") 712 to monitoring device 10. For example, closed-loop control data 712 can provide feedback to the monitoring device user or patient. It will be appreciated that feedback system or system 710 can be included in monitoring device, telemetry system 32 or be a standalone system or subsystem.

In another embodiment, feedback system or subsystem 710 can generate and communicate signals 714 for video/audio data communication to the monitoring device user or patient.

In another embodiment feedback system or subsystem 710 can generate and communicate monitoring device user or patient control data ("PCD") 716 to the monitoring device user or patient. In another embodiment, feedback system or subsystem 710 generates and communicates sensing control data ("SCD") 718 to a feedback system 720 associated with the monitoring device 10 for providing feedback to the monitoring device user or patient. Signals and data 712 through 718 can be converted into signals for executing feedback information, visual, audio and the like, to the monitoring device user or patient.

An example of feedback system or subsystem 710 includes, but is not limited to, a feedback engine installed as software and/or firmware on any type at the telemetry system 32. In one embodiment, the feedback system or subsystem 710 is at monitoring device 10 and receives feedback signals from telemetry system.

Figure 21:
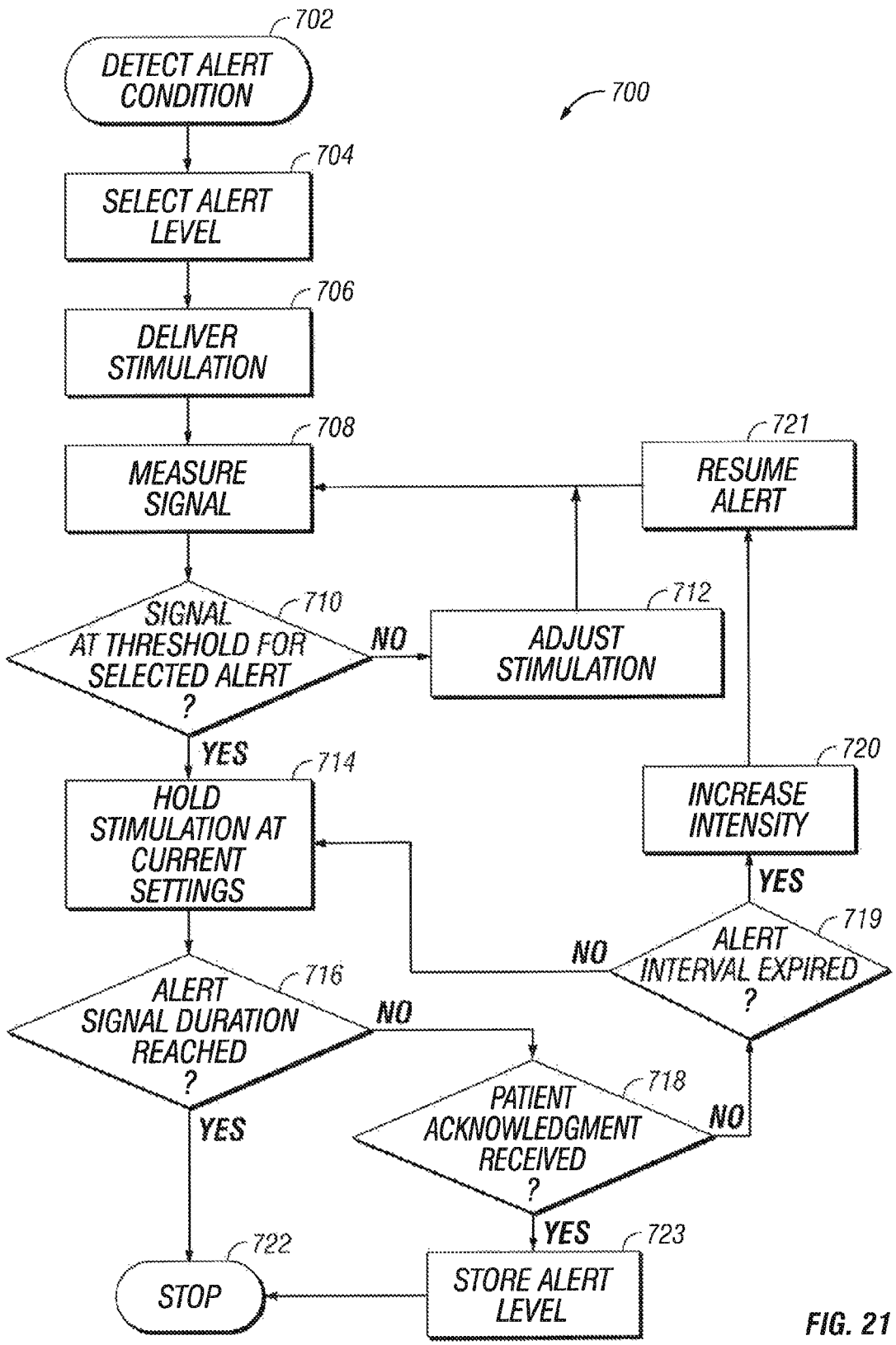
FIG. 21 is a flow chart illustrating one embodiment of proving feedback and/or alerts to a user or patient.

FIG. 21 is a flow chart 700 illustrating one embodiment of proving feedback and/or alerts to a user through or without monitoring device 10. Flow chart 700 and other flow charts presented herein are intended to illustrate the functional operation of the device feedback system or subsystem 710 and should not be construed as reflective of a specific form of software or hardware necessary to practice the methods described. It is believed that the particular form of software will be determined primarily by the particular system architecture employed in the device and by the particular detection and electrical stimulation delivery methodologies employed by the device.

At block 702, user or patient feedback is detected. Examples of feedback include but are not limited to lifestyle parameters, medical conditions, lifestyle events, exercise parameters, battery 24 life of the monitoring device 10, battery 24 replacement required, lead or sensor 14 function, pending therapy delivery, and the like. The type of feedback and alert conditions detected can vary.

At block 704, a feedback or alert is selected that is associated with a detected feedback or alert condition. Selection of a feedback or alert signal may involve the selection of any of the above listed parameters listed above relative to user or patient, used to control the feedback or alert signal. At block 706 the feedback or alert signal is delivered according to settings selected at block 704.

At block 708, a sensor 14 signal is measured at telemetry system 32 or monitoring device 10, analyzed and compared to a threshold level corresponding to the selected alert level at block 710. An alert threshold level may be predefined or tailored to a given monitoring device user or patient. If the measured sensor 14 response does not correspond to an expected threshold signal level or characteristic pattern of the selected feedback or alert signal, the feedback or alert signal is adjusted at block 712 in a closed-loop feedback method until the sensor signal measured at block 708 falls within a desired range of an expected threshold level, as determined at block 710. Once the desired feedback or alert signal level is reached, the feedback or alert signal stimulation parameters are maintained at the current settings at block 714 to maintain the sensor signal measurement within a desired range of the threshold. Maintaining the feedback or alert signal response within a desired threshold range promotes the reliability of the feedback or alert signal in informing the monitoring device user or patient of a detected parameter described above.

Determining that the sensor signal corresponds to a selected feedback or alert threshold at block 710 may involve detecting a magnitude of the a sensor signal amplitude or frequency, and/or recognizing an intended alert pattern (e.g. short-long burst sequences, strong-weak burst sequences, or the like) based on a morphology of the sensor signal. As such, measuring the sensor signal at block 708 may involve measuring signal magnitude as well as frequency characteristics during the feedback or alert signal delivery.

Additionally or alternatively, frequency characteristics of the sensor signal may be determined to detect sensor 10 signals. The frequency power band of the sensor may be analyzed for correspondence to frequency, amplitude and the like. Additionally, a sensor waveform may be evaluated for correspondence to a frequency or amplitude. A combination of the amplitude and frequency of the sensor signal may also be measured to determine a monitoring device user or patient medical or lifestyle condition.

The feedback or alert signal may be terminated if a predetermined maximum alert duration has expired, as determined at block 716. If a maximum feedback or alert signal duration is not reached, the feedback or alert signal may continue to be held at the current stimulation signal settings at block 714 until the alert expires. Alternatively, the process may return to block 708 to continue monitoring the sensor signal throughout the duration of the alert delivery in order to make further adjustments at block 712 as needed to maintain a desired strength and pattern of the monitoring device user or patient feedback or alert signal. If the feedback or alert signal maximum duration is reached, the signal may be immediately terminated at block 722.

In some embodiments, if a monitoring device user or patient acknowledgement signal is received prior to the maximum signal duration expiring, as determined at decision block 718, the feedback or alert signal is terminated at block 722. A monitoring device user or patient acknowledgment may be in a variety of forms.

In one specific embodiment, if monitoring device user or patient acknowledgement is not received or detected at block 718, the intensity of the feedback or alert signal may be increased at block 720, steadily or in step-wise, predetermined intervals within a feedback or alert signal maximum duration. It will be appreciated that monitoring device user or patient acknowledgement is not required. The intensity may be increased at block 720 according to a predefined pattern by increasing pulse amplitude (up to some maximum), increasing pulse width, increasing pulse frequency or other adjustment that causes a relatively stronger contraction, i.e., greater recruitment of the muscle being stimulated. Adjusting the intensity of the feedback or alert signal at block 720 may also be performed using sensor signal feedback control by returning to block 708 to compare measured sensor signal characteristics to a next higher feedback or alert signal threshold level. In other words, the sensor signal is compared to a different, increased intensity, threshold than an initial threshold in order to control the feedback or alert signal to elicit a stronger response as compared to the initial feedback or alert signal settings. Thus for a given alert condition, multiple alert intensity levels may be stored in the telemetry system 32 memory along with multiple expected sensor signal responses or thresholds for each intensity level. The sensor signal is used in a closed-loop feedback method to adjust feedback or alert signal control parameters to achieve a feedback or alert signal with the desired intensity at each level.

The feedback or alert signal may be delivered continuously, with continuous or stepwise increasing intensity according to a predefined pattern, until either a maximum alert duration is reached or a monitoring device user or patient acknowledgment is received. In other embodiments, a feedback or alert signal may be delivered intermittently until monitoring device user or patient acknowledgement or expiration of a maximum feedback or alert signal duration, whichever occurs earlier. When delivered intermittently, the feedback or alert signal is delivered at an initial intensity for a predefined alert interval. The feedback or alert signal is held at the current settings at block 714 until the alert interval has expired as determined at block 719. If the alert interval expires, the intensity is increased at block 720 and the feedback or alert signal is resumed for another feedback or alert signal interval at block 721. A pause between differing feedback and alert signal intensities may be applied. As a non-limiting example, the feedback or alert signal may be delivered for a 30 second interval at an initial intensity. This process may continue until a maximum alert duration is reached as determined at block 716, or monitoring device user or patient acknowledgement is received at block 718.

As non-limiting examples, a maximum alert duration may be set at 5 minutes, 10 minutes, 30 minutes, one hour or more and may be set differently for different alert conditions, e.g. according to the seriousness of a particular alert condition. Alert intervals applied during the maximum alert duration may be set differently for different alert conditions and different alert intervals may be applied during a given maximum alert duration. For example, the alert intervals may increase in length as feedback or alert signal intensity is increased.

The same is true relative to the amplitude and duration of the alert signal.

If a maximum alert duration is not reached the alert is terminated at block 722 and optionally repeated at a later time. As described above, a maximum alert duration may correspond to a continuously delivered feedback or alert signal, which may be increased in intensity according to a predefined pattern, or an intermittently delivered feedback or alert signal that includes successive intervals of increasing intensity of the feedback or alert signal with intervening pauses of no feedback or alert signal.

In some embodiments, initial feedback or alert signal settings may be "learned" over time, based on a monitoring device user or patient's response to prior alerting attempts. When a monitoring device user or patient acknowledgement is received at block 718, the feedback or alert signal control parameters are stored at block 723. These alert settings may be used as the initial feedback or alert signal settings the next time the same alert condition is detected (or another condition using the same feedback or alert signal). These stored settings can also be used for further analysis. In one embodiment, the user or patient can provide input relative to the feedback or alert signal. This input can be used to adjust the thresholds for the alerts. In this way, if a previous alert was generated and no monitoring device user or patient acknowledgement occurred until a particular sensor signal amplitude or frequency measurement was reached, the next time the alert is generated, the alert is delivered using a lower setting at which a monitoring device user or patient acknowledgement occurred to improve responsiveness of the monitoring device user or patient to feedback or alert signals.

Adjustment of user or patient parameters at block 712, as the result of an input provided by the user or patient can be provided for maintaining a feedback or alert signal within a targeted threshold level.

The monitoring device 10 and/or the telemetry system 32 can include a feedback loop. User and patient profiles can be stored in database 18, which can include a non-volatile memory. A user or patient can input information 64 about the desired circumstances or parameters relative to a parameter that is measured by a sensor 14. The processor 20 and/or 34 can include a variety of different user and patient profiles relating to information obtained from sensors 14. The processor 20 and/or 34 can customize by either scaling or modifying the user or patient profile based on additional user or patient input information.

Furthermore, feedback or alert signals corresponding to different alert conditions may be distinguished by the monitoring device user or patient by delivering the feedback or alert signals to different body locations. When feedback or alert signals are delivered to different body locations, multiple sensors may be required in the telemetry system 32 system such that a sensor signal responsive to alert stimulation at each body location is available. Depending on the number of body locations and relative distance there between, one or more sensors may be implanted in order to provide at least one sensor in operative relation to each of the targeted alert stimulation sites.

Figure 22:
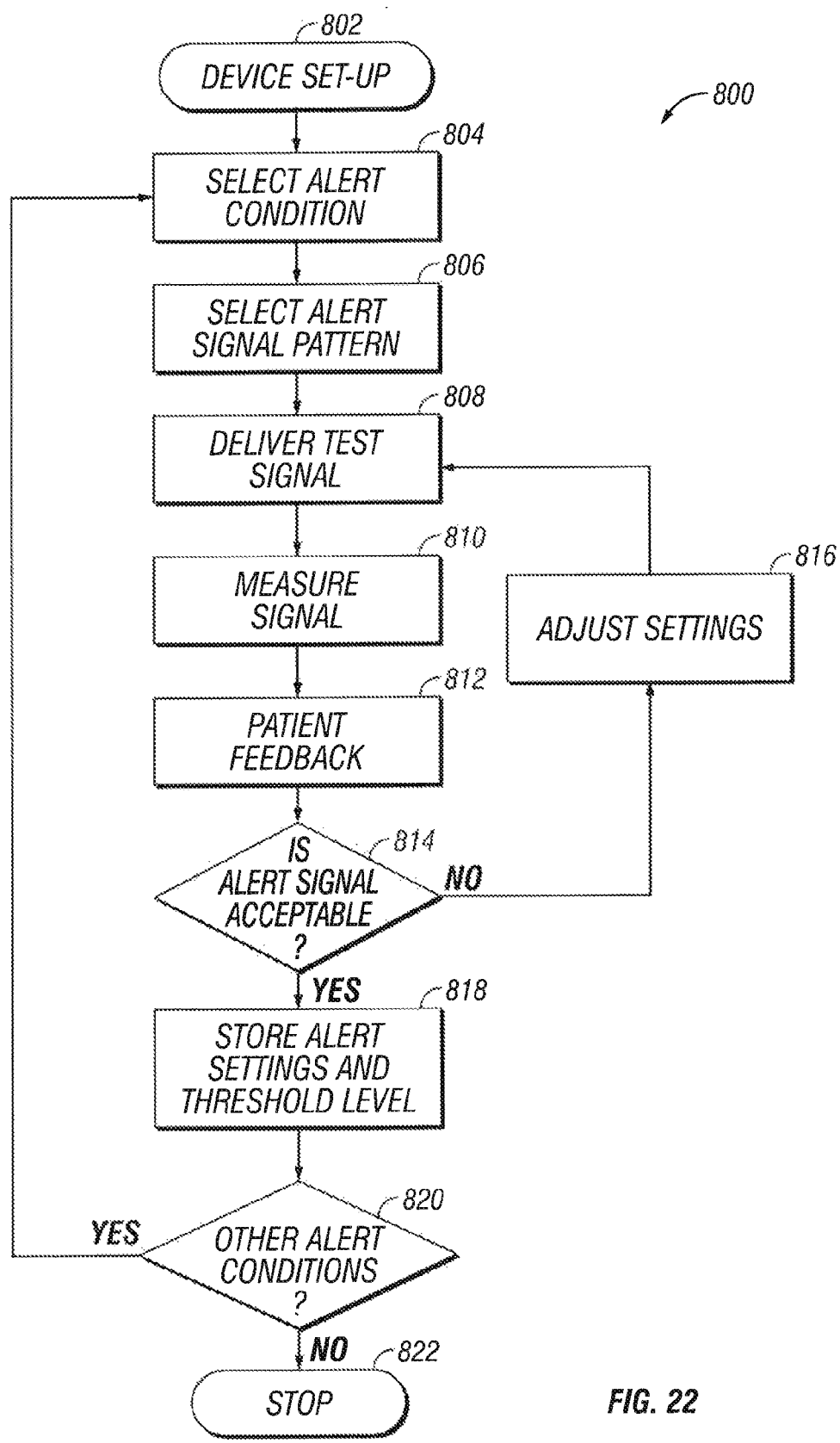
FIG. 22 is a flow chart illustrating one embodiment for a method of establishing control parameters for a monitoring device user or patient feedback or alert signal and a sensor signal threshold range for the feedback or alert signal.

FIG. 22 is a flow chart, illustrating one embodiment for a method of establishing control parameters for a monitoring device user or patient feedback or alert signal and a sensor signal threshold range for the feedback or alert signal. At block 802, a set-up procedure is initiated. In one embodiment, this can be achieved using an external programmer having a user interface. In another embodiment, information from the telemetry system database 18 that has been collected is utilized, along with any user or patient input. The process shown in flow chart 800 may be performed at any time. In one embodiment, it is done at the time the user or patient is connected to monitoring device 10. In another embodiment, it is done at a time subsequent the initial connection of the user or patient to the monitoring device 10. The process allows the establishment alert conditions and corresponding feedback or alert signals tailored to a particular monitoring device user or patient's needs. An alert condition is selected at block 804, which may be any of the parameters listed above, that receive input from a sensor 14. Alert conditions may be predefined or customized for a monitoring device user or patient.

At block 806, a feedback or alert signal pattern for the alert is selected from a person or from telemetry system database 18, and the like, which may be a default pattern for a selected alert condition or customized using any combination signals from sensors 14. Various parameters controlling the alert signal may be programmable.

Optionally, at block 808 a test signal is delivered to the monitoring device user or patient according to a selected sensor signal value. In one embodiment, the sensor signal is measured during the test signal at block 810, which may include measurements of both signal magnitude and frequency characteristics. At block 812, the patient/user may optionally provide input to establish whether the test signal is adequately perceivable and distinct from any other feedback or alert signals that have already been established. User or patient feedback may be received by a user interface included in a monitoring device 10, home monitor, device programmer, or other external device in communication with the telemetry system 32. User or patient feedback may be received by a variety of different ways known in the art when the signal is acceptable or using a signal transmitted by telemetry system 32 or monitoring device 10. A feedback or alert signal may be unacceptable to the monitoring device user or patient.

If the signal is not acceptable to the monitoring device user or patient, or not adequately measured by a sensor 14 to facilitate closed-loop feedback of the signal, as determined at block 814, one or more feedback or alert signal control parameters is adjusted at block 816, and the process at blocks 808 through 814 repeats until an acceptable feedback or alert signal is established. The feedback or alert signal settings and the sensor signal characteristic(s) associated with the acceptable feedback or alert signal are stored at block 818 to establish a threshold range of the magnitude and/or frequency characteristics of the sensor signal for the given feedback or alert signal.

If additional alert conditions can be detected by the telemetry system 32, as determined at block 820, a unique feedback or alert signal pattern can be selected for the next alert condition by returning to block 804 and repeating the process shown in blocks 804 through 818. Each alert condition may be assigned a unique monitoring device user or patient feedback or alert signal that is established by storing expected sensor signal characteristics with corresponding feedback or alert signal parameters. The monitoring device user or patient can provide feedback such that each feedback or alert signal is easily perceived, recognized and distinguished from other feedback or alert signals.

For each acceptable feedback or alert signal, a sensor threshold level is established, which may include both a magnitude component and a frequency component. The stored sensor signal thresholds allow the feedback or alert signal to be adjusted as needed during an actual monitoring device user or patient alert to most closely match the magnitude and/or frequency characteristics of the established feedback or alert signal. The monitoring device user or patient can be "trained" to recognize different feedback or alert signal patterns, intensities (strength or duration of the muscle response), and/or locations and their correspondence to different alert conditions.

Once all sensor-based threshold characteristics have been stored for all alert conditions, the process is terminated at block 822. The stored sensor signal data can then be used in a closed-loop feedback method for controlling feedback or alert signal stimulation parameters during normal operation of the telemetry system 32 as described in conjunction with FIG. 21.

As illustrated in FIG. 21, one or more analysis tools 724 at the telemetry system 32 the user information and produces analysis information that is sent to the telemetry system 32. The one or more analysis tools 724 can be part of or separate from the database 18.

The database includes base standards for at least one of user, activities, behaviors, habit information and health information that is indicative of a healthy lifestyle of activities, behaviors, habit information, exercise programs and health condition. The user information received from the monitoring device 10 is analyzed relative to the base standards in the database. In one embodiment, the base standards in operation are updatable. The update information includes updated base standards.

As set forth above, the monitoring device 10 generates data indicative of various physiological parameters of an individual, as set forth above, including but not limited to, the individual's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and UV radiation absorption. In certain cases, the data indicative of the various physiological parameters is the signal or signals themselves generated by the one or more sensors 14 and in certain other cases the data is calculated by telemetry system 32. Methods for generating data indicative of various physiological parameters and sensors to be used therefor are well known. Table 1 provides several examples of such well known methods and shows the parameter in question, the method used, the sensor device used, and the signal that is generated. Table 1 also provides an indication as to whether further processing based on the generated signal is required to generate the data.

TABLE 1

| Parameter | Method | Sensor | Signal | Processing |
|---|---|---|---|---|
| Heart Rate | EKG | 2 Electrodes | DC Voltage | Yes |
| Pulse Rate | BVP | LED Emitter and Optical Sensor | Change in Resistance | Yes |
| Beat-to-Beat Variability | Heart Rate | 2 Electrodes | DC Voltage | Yes |
| EKG | Skin surface potentials | 3-10 electrodes | DC Voltage | No |
| Respiration Rate | Chest Volume change | Strain Gauge | Change in Resistance | Yes |
| Skin Temperature | Surface temperature probe | Thermistors | Change in Resistance | Yes |
| Core Temperature | Esophageal or rectal probe | Thermistors | Change in Resistance | Yes |
| Heat Flow | Heat Flux | Thermopile | DC Voltage | Yes |
| Galvanic Skin Response | Skin Conductance | 2 Electrodes | Change in Resistance | No |
| EMG | Skin surface potentials | 3 electrodes | DC Voltage | No |
| EEG | Skin surface potentials | Multiple electrodes | DC Voltage | Yes |
| EOG | Eye Movement | Thin film piezoelectric sensors | DC Voltage | Yes |
| Blood Pressure | Non-invasive Korotkuff sounds | Electronic sphygromarometer | Change in Resistance | Yes |
| Body Fat | Body impedance | 2 active electrodes | Change in Resistance | Yes |

TABLE 1-continued

| Parameter | Method | Sensor | Signal | Processing |
|---|---|---|---|---|
| Activity in Interpreted G shocks per minute | Body movement | Accelerometer | DC Voltage, capacitance changes | Yes |
| Oxygen Consumption | Oxygen update | Electro-chemical | DC Voltage Change | Yes |
| Glucose Level | Non-invasive | Electro-chemical | DC Voltage Change | Yes |
| Body position (e.g., supine, erect, sitting) | N/A | Mercury switch | DC Voltage Change | Yes |
| Muscle pressure | N/A | Thin film piezoelectric sensors | DC Voltage Change | Yes |
| UV Radiation Absorption | N/A | UV Sensitive photo cells | DC Voltage Change | Yes |

The types of data listed in Table 1 are intended to be examples of the types of data that can be generated by monitoring device 10. It is to be understood that other types of data relating to other parameters can be generated by sensor device 10 without departing from the scope of the present invention.

Telemetry system 32 can be programmed to summarize and analyze the data. For example, processor 18 or 34 can be programmed to calculate an average, minimum or maximum heart rate or respiration rate over a defined period of time, such as ten minutes. Monitoring device 10 may be able to derive information relating to an individual's physiological state based on the data indicative of one or more physiological parameters. Processor 18 or 34 can be programmed to derive such information using known methods based on the data indicative of one or more physiological parameters. Table 2 provides examples of the type of information that can be derived, and indicates some of the types of data that can be used therefor.

TABLE 2

| Derived Information | Data Used |
|---|---|
| Ovulation | Skin temperature, core temperature, oxygen consumption Beat-to-beat variability, heart rate, pulse rate, respiration rate, skin temperature, core temperature, heat flow, galvanic skin response, EMG, EEG, EOG, blood pressure, oxygen consumption |
| Sleep onset/wake | Beat-to-beat variability, heart rate, pulse rate, respiration rate, skin temperature, core temperature, heat flow, galvanic skin response, EMG, EEG, EOG, blood pressure, oxygen consumption |
| Calories burned | Heart rate, pulse rate, respiration rate, heat flow, activity, oxygen consumption |
| Basal metabolic rate | Heart rate, pulse rate, respiration rate, heat flow, activity, oxygen consumption |
| Basal temperature | Skin temperature, core temperature |
| Activity level | Heart rate, pulse rate, respiration rate, heat flow, activity, oxygen consumption |
| Stress level | EKG, beat-to-beat variability, heart rate, pulse rate, respiration rate, skin temperature, heat flow, galvanic skin response, EMG, EEG, blood pressure, activity, oxygen consumption |
| Maximum oxygen consumption rate | EKG, heart rate, pulse rate, respiration rate, heat flow, blood pressure, activity, oxygen consumption |
| Rise time or the time it takes to rise from a resting rate to 85% of a target maximum | Heart rate, pulse rate, heat flow, oxygen consumption |

TABLE 2-continued

| Derived Information | Data Used |
| --- | --- |
| Time in zone or the time heart rate was above 85% of a target maximum | Heart rate, pulse rate, heat flow, oxygen consumption |
| Recovery time or the time it takes heart rate to return to a resting rate after heart rate was above 85% of a target maximum | Heart rate, pulse rate, heat flow, oxygen consumption |

Additionally, monitoring device 10 with telemetry system 32 may also generate data indicative of various contextual parameters relating to the environment surrounding the individual. For example, monitoring device 10 can generate data indicative of the air quality, sound level/quality, light quality or ambient temperature near the individual, or even the global positioning of the individual. Sensor device 10 may include one or more sensors for generating signals in response to contextual characteristics relating to the environment surrounding the individual, the signals ultimately being used to generate the type of data described above. Such sensors are well known, as are methods for generating contextual parametric data such as air quality, sound level/quality, ambient temperature and global positioning.

In addition to using monitoring device 10 to automatically collect physiological data relating to an individual user, a kiosk could be adapted to collect such data by, for example, weighing the individual, providing a sensing device similar to monitoring device 10 on which an individual places his or her hand or another part of his or her body, or by scanning the individual's body using, for example, laser technology or an iStat blood analyzer. The kiosk would be provided with processing capability as described herein and access to the relevant electronic network, and would thus be adapted to send the collected data to the telemetry system 32. A desktop sensing device, again similar to monitoring device 10, on which an individual places his or her hand or another part of his or her body, may also be provided. For example, such a desktop sensing device could be a blood pressure monitor in which an individual places his or her arm.

Furthermore, in addition to collecting data by automatically sensing such data in the manners described above, individuals can also manually provide data relating to various life activities that is ultimately transferred to and stored at telemetry system 32 An individual user can access a web site maintained by monitoring system 32 and can directly input information relating to life activities by entering text freely, by responding to questions posed by the web site, or by clicking through dialog boxes provided by the web site. Telemetry system 32 can also be adapted to periodically send electronic mail messages containing questions designed to elicit information relating to life activities to monitoring device 10, a mobile device, PC or to some other device that can receive electronic mail. The individual would then provide data relating to life activities to telemetry system 32 by responding to the appropriate electronic mail message with the relevant data. Telemetry system 32 may also be adapted to place a telephone call to an individual user in which certain questions would be posed to the individual user. The user could respond to the questions by entering information using a telephone keypad, or by voice, in which case conventional voice recognition technology would be used by telemetry system 32 to receive and process the response. The telephone call may also be initiated by the user, in which case the user could speak to a person directly or enter information using the keypad or by voice/voice recognition technology. Monitoring system 32 may also be given access to a source of information controlled by the user, for example the user's electronic calendar such as that provided with the Outlook® calendaring system sold by Microsoft Corporation of Redmond, Wash., from which it could automatically collect information. The data relating to life activities may relate to the eating, sleep, exercise, mind centering or relaxation, and/or daily living habits, patterns and/or activities of the individual. Thus, sample questions may include: What did you have for lunch today? What time did you go to sleep last night? What time did you wake up this morning? How long did you run on the treadmill today?

Feedback may also be provided to a user directly through monitoring device 10 in a visual form, for example through an LED or LCD or by constructing sensor device 10, at least in part, of a thermochromatic plastic, in the form of an acoustic signal or in the form of tactile feedback such as vibration. Such feedback may be a reminder or an alert to eat a meal or take medication or a supplement such as a vitamin, to engage in an activity such as exercise or meditation, or to drink water when a state of dehydration is detected. Additionally, a reminder or alert can be issued in the event that a particular physiological parameter such as ovulation has been detected, a level of calories burned during a workout has been achieved or a high heart rate or respiration rate has been encountered.

As will be apparent to those of skill in the art, it may be possible to "download" data from monitoring system 32 to sensor device 10. The flow of data in such a download process would be substantially the reverse of that described above with respect to the upload of data monitoring device 10. Thus, it is possible that the firmware monitoring device 10 can be updated or altered remotely, i.e., new firmware added, and the like.

It is also contemplated that a user will input additional data during a session, for example, information relating to the user's eating or sleeping habits.

Data collected by monitoring device 10 can be periodically uploaded to telemetry system 32.

Third parties such as insurance companies or research institutions may be given access, possibly for a fee, to certain of the information stored in monitoring system 32.

When an individual user first becomes a registered user or member of telemetry system, that user can complete a detailed survey. The purposes of the survey are to: identify unique characteristics/circumstances for each user that they might need to address in order to maximize the likelihood that they will implement and maintain a healthy lifestyle as suggested by telemetry system 32; gather baseline data which will be used to set initial goals for the individual user and facilitate the calculation and display of certain graphical data output such as the Health Index pistons; identify unique user characteristics and circumstances that will help telemetry system 32 customize the type of content provided to the user; and identify unique user characteristics and circumstances that can guide the user to address as possible barriers to a healthy lifestyle through the problem-solving function monitoring system.

The specific information to be surveyed may include: key individual temperamental characteristics, including activity level, regularity of eating, sleeping, and bowel habits, initial response to situations, adaptability, persistence, threshold of responsiveness, intensity of reaction, and quality of mood; the user's level of independent functioning, i.e., self-organization and management, socialization, memory, and academic achievement skills; the user's ability to focus and sustain attention, including the user's level of arousal, cognitive tempo, ability to filter distractions, vigilance, and self-monitoring; the user's current health status including current weight, height, and blood pressure, most recent general physician visit, gynecological exam, and other applicable physician/healthcare contacts, current medications and supplements, allergies, and a review of current symptoms and/or health-related behaviors; the user's past health history, i.e., illnesses/surgeries, family history, and social stress events, such as divorce or loss of a job, that have required adjustment by the individual; the user's beliefs, values and opinions about health priorities, their ability to alter their behavior and, what might contribute to stress in their life, and how they manage it; the user's degree of self-awareness, empathy, empowerment, and self-esteem, and the user's current daily routines for eating, sleeping, exercise, relaxation and completing activities of daily living; and the user's perception of the temperamental characteristics of two key persons in their life, for example, their spouse, a friend, a co-worker, or their boss, and whether there are clashes present in their relationships that might interfere with a healthy lifestyle or contribute to stress.

Figure 23:
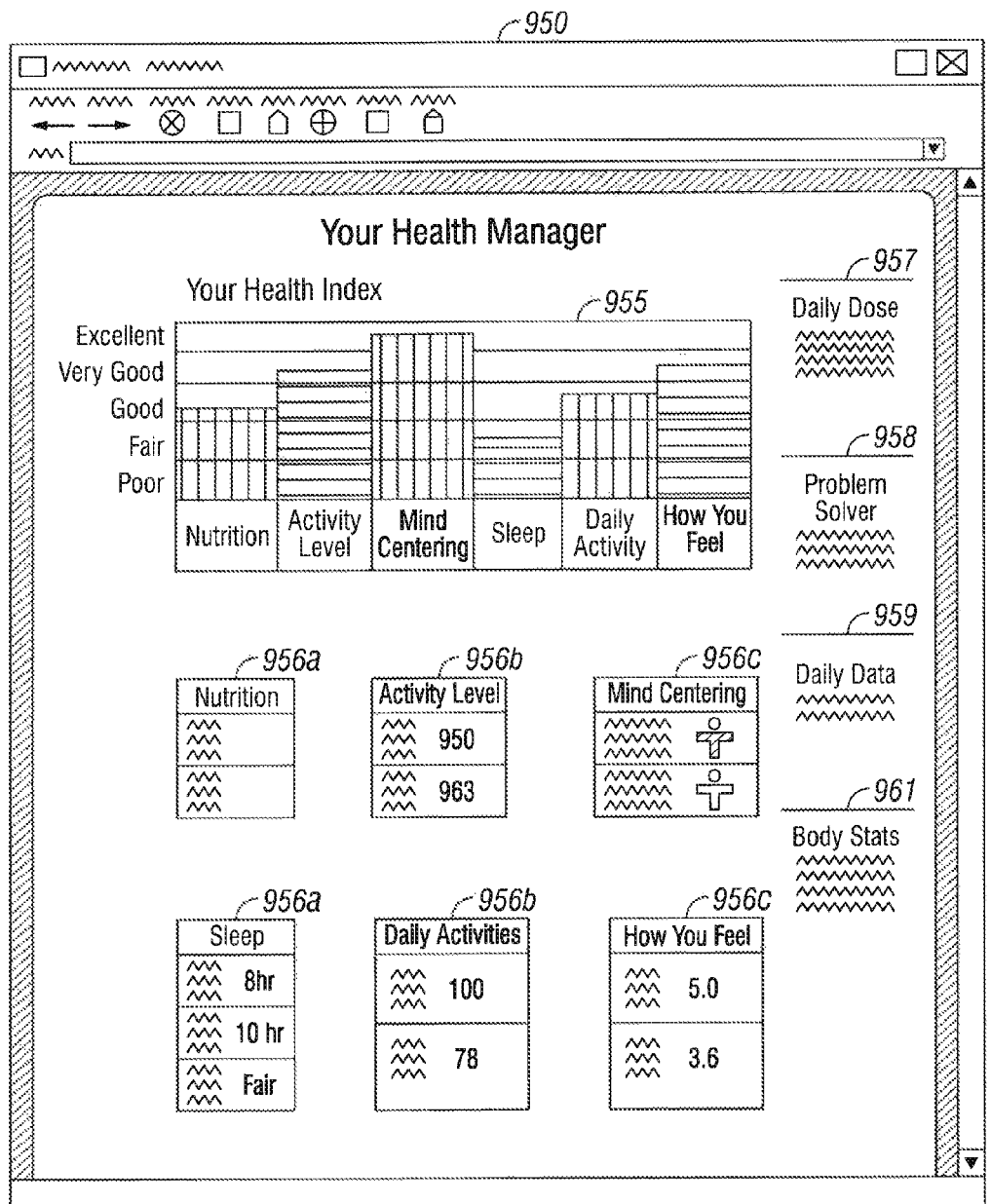
FIG. 23 is a representation of an embodiment of the Health Manager web page according to an aspect of the present invention.

Each member user can access, through a home web page of telemetry system 32, to a series of web pages customized for that user, referred to as the Health Manager. The opening Health Manager web page 950 is shown in FIG. 23. The Health Manager web pages are the main workspace area for the member user. The Health Manager web pages comprise a utility through which telemetry system 32 provides various types and forms of data, commonly referred to as analytical status data, to the user that is generated from the data it collects or generates, namely one or more of: the data indicative of various physiological parameters generated by monitoring device 10; the data derived from the data indicative of various physiological parameters; the data indicative of various contextual parameters generated by monitoring device 10; and the data input by the user. Analytical status data is characterized by the application of certain utilities or algorithms to convert one or more of the data indicative of various physiological parameters generated by monitoring device 10, the data derived from the data indicative of various physiological parameters, the data indicative of various contextual parameters generated by monitoring device 10, and the data input by the user into calculated health, wellness and lifestyle indicators. For example, based on data input by the user relating to the foods he or she has eaten, things such as calories and amounts of proteins, fats, carbohydrates, and certain vitamins can be calculated. As another example, skin temperature, heart rate, respiration rate, heat flow and/or GSR can be used to provide an indicator to the user of his or her stress level over a desired time period. As still another example, skin temperature, heat flow, beat-to-beat heart variability, heart rate, pulse rate, respiration rate, core temperature, galvanic skin response, EMG, EEG, EOG, blood pressure, oxygen consumption, ambient sound and body movement or motion as detected by a device such as an accelerometer can be used to provide indicators to the user of his or her sleep patterns over a desired time period.

Located on the opening Health Manager web page 950 is Health Index 955. Health Index 955 is a graphical utility used to measure and provide feedback to member users regarding their performance and the degree to which they have succeeded in reaching a healthy daily routine suggested by monitoring system 32. Health Index 955 thus provides an indication for the member user to track his or her progress. Health Index 955 includes six categories relating to the user's health and lifestyle: Nutrition, Activity Level, Mind Centering, Sleep, Daily Activities and How You Feel. The Nutrition category relates to what, when and how much a person eats and drinks. The Activity Level category relates to how much a person moves around. The Mind Centering category relates to the quality and quantity of time a person spends engaging in some activity that allows the body to achieve a state of profound relaxation while the mind becomes highly alert and focused. The Sleep category relates to the quality and quantity of a person's sleep. The Daily Activities category relates to the daily responsibilities and health risks people encounter. Finally, the How You Feel category relates to the general perception that a person has about how they feel on a particular day. Each category has an associated level indicator or piston that indicates, can be on a scale ranging from poor to excellent, how the user is performing with respect to that category.

When each member user completes the initial survey described above, a profile is generated that provides the user with a summary of his or her relevant characteristics and life circumstances. A plan and/or set of goals are provided in the form of a suggested healthy daily routine. The suggested healthy daily routine may include any combination of specific suggestions for incorporating proper nutrition, exercise, and mind centering, sleep, and selected activities of daily living in the user's life. Prototype schedules may be offered as guides for how these suggested activities can be incorporated into the user's life. The user may periodically retake the survey, and based on the results, the items discussed above will be adjusted accordingly.

The Nutrition category is calculated from both data input by the user and sensed by monitoring device 10. The data input by the user comprises the time and duration of breakfast, lunch, dinner and any snacks, and the foods eaten, the supplements such as vitamins that are taken, and the water and other liquids consumed during a relevant, pre-selected time period. Based upon this data and on stored data relating to known properties of various foods, monitoring system 32 calculates well known nutritional food values such as calories and amounts of proteins, fats, carbohydrates, vitamins, etc., consumed.

The Nutrition Health Index piston level can be determined with respect to the following suggested healthy daily routine: eat at least three meals; eat a varied diet consisting of 6-11 servings of bread, pasta, cereal, and rice, 2-4 servings fruit, 3-5 servings of vegetables, 2-3 servings of fish, meat, poultry, dry beans, eggs, and nuts, and 2-3 servings of milk, yogurt and cheese; and drink 8 or more 8 ounce glasses of water. This routine may be adjusted based on information about the user, such as sex, age, height and/or weight. Certain nutritional targets may also be set by the user or for the user, relating to daily calories, protein, fiber, fat, carbohydrates, and/or water consumption and percentages of total consumption. Parameters utilized in the calculation of the relevant piston level include the number of meals per day, the number of glasses of water, and the types and amounts of food eaten each day as input by the user.

Figure 24:
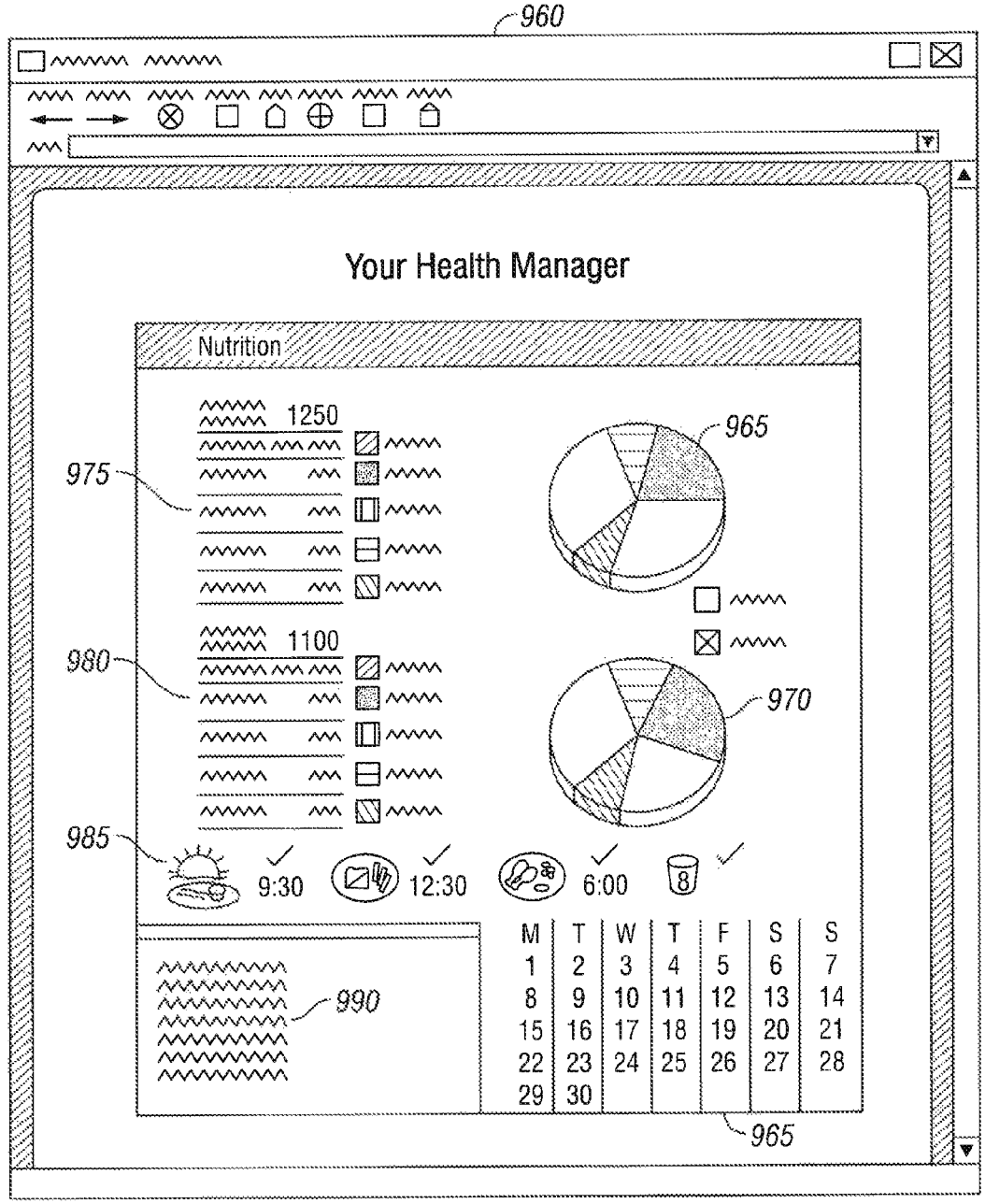
FIG. 24 is a representation of an embodiment of the nutrition web page according to an aspect of the present invention.

Nutritional information is presented to the user through nutrition web page 960 as shown in FIG. 24. The preferred nutritional web page 960 includes nutritional fact charts 965 and 970 which illustrate actual and target nutritional facts, respectively as pie charts, and nutritional intake charts 975 and 980 which show total actual nutritional intake and target nutritional intake, respectively as pie charts. Nutritional fact charts 965 and 970 preferably show a percentage breakdown of items such as carbohydrates, protein and fat, and nutritional intake charts 975 and 980 are preferably broken down to show components such as total and target calories, fat, carbohydrates, protein, and vitamins. Web page 960 also includes meal and water consumption tracking 985 with time entries, hyperlinks 990 which allow the user to directly access nutrition-related news items and articles, suggestions for refining or improving daily routine with respect to nutrition and affiliate advertising elsewhere on the network, and calendar 995 for choosing between views having variable and selectable time periods. The items shown at 990 may be selected and customized based on information learned about the individual in the survey and on their performance as measured by the Health Index.

The Activity Level category of Health Index 955 is designed to help users monitor how and when they move around during the day and utilizes both data input by the user and data sensed by monitoring device 10. The data input by the user may include details regarding the user's daily activities, for example the fact that the user worked at a desk from 8 a.m. to 5 p.m. and then took an aerobics class from 6 p.m. to 7 p.m. Relevant data sensed by monitoring device 10 may include heart rate, movement as sensed by a device such as an accelerometer, heat flow, respiration rate, calories burned, GSR and hydration level, which may be derived by monitoring device 10 or telemetry system 32. Calories burned may be calculated in a variety of manners, including: the multiplication of the type of exercise input by the user by the duration of exercise input by the user; sensed motion multiplied by time of motion multiplied by a filter constant; or sensed heat flux multiplied by time multiplied by a filter constant.

The Activity Level Health Index piston level is preferably determined with respect to a suggested healthy daily routine that includes: exercising aerobically for a pre-set time period, preferably 20 minutes, or engaging in a vigorous lifestyle activity for a pre-set time period, preferably one hour, and burning at least a minimum target number of calories, preferably 205 calories, through the aerobic exercise and/or lifestyle activity. The minimum target number of calories may be set according to information about the user, such as sex, age, height and/or weight. Parameters utilized in the calculation of the relevant piston level include the amount of time spent exercising aerobically or engaging in a vigorous lifestyle activity as input by the user and/or sensed by monitoring device 10, and the number of calories burned above pre-calculated energy expenditure parameters.

Figure 25:
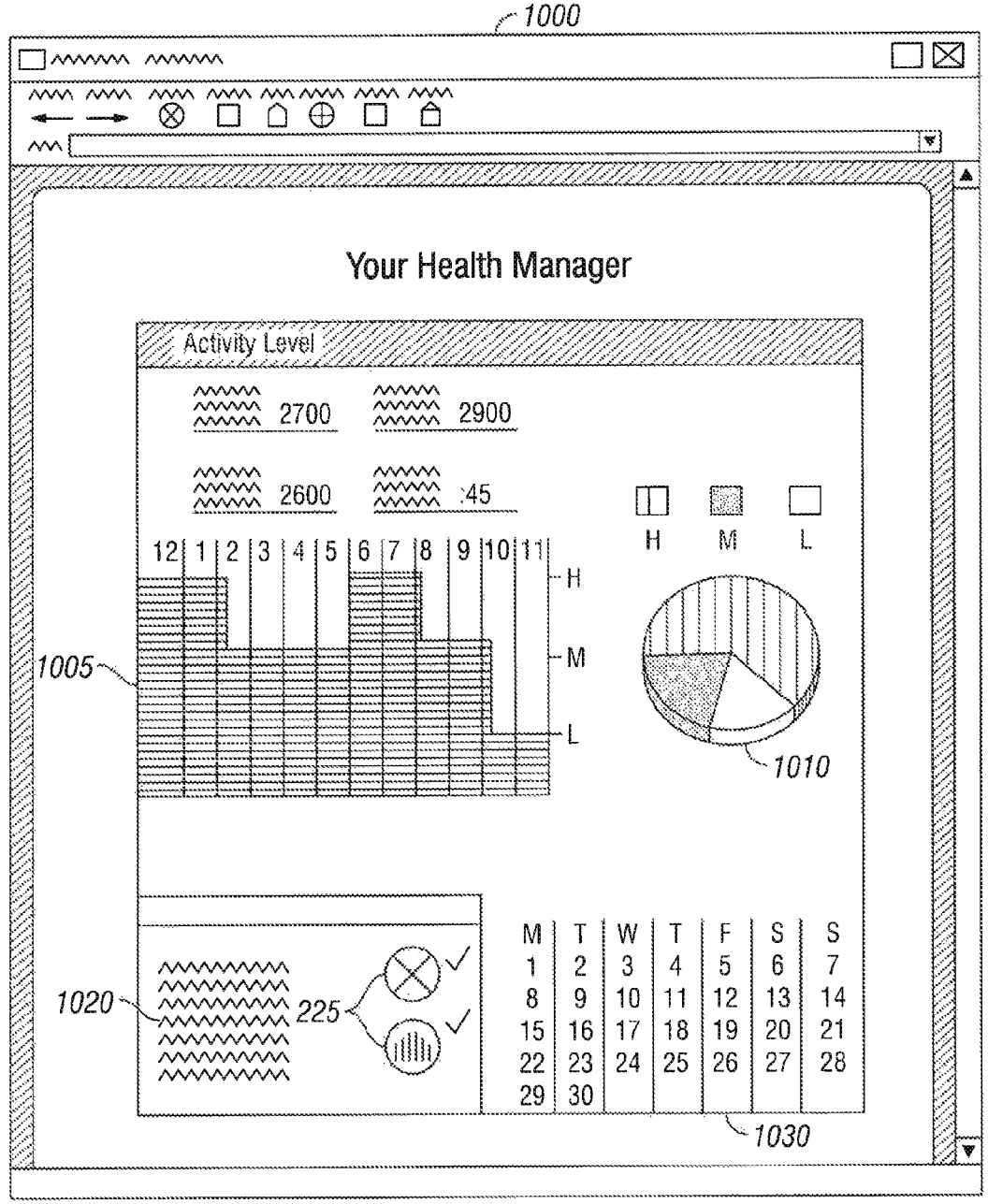
FIG. 25 is a representation of an embodiment of the activity level web page according to an aspect of the present invention.

Information regarding the individual user's movement is presented to the user through activity level web page 1000 shown in FIG. 25, which may include activity graph 1005 in the form of a bar graph, for monitoring the individual user's activities in one of three categories: high, medium and low intensity with respect to a pre-selected unit of time. Activity percentage chart 1010, in the form or a pie chart, may also be provided for showing the percentage of a pre-selected time period, such as one day, that the user spent in each category. Activity level web page 1000 may also include calorie section 1015 for displaying items such as total calories burned, daily target calories burned, total caloric intake, and duration of aerobic activity. Finally, activity level web page 1000 may include at least one hyperlink 1020 to allow a user to directly access relevant news items and articles, suggestions for refining or improving daily routine with respect to activity level and affiliate advertising elsewhere on the network. Activity level web page 1000 may be viewed in a variety of formats, and may include user-selectable graphs and charts such as a bar graph, pie chart, or both, as selectable by Activity level check boxes 1025. Activity level calendar 1030 is provided for selecting among views having variable and selectable time periods. The items shown at 1020 may be selected and customized based on information learned about the individual in the survey and on their performance as measured by the Health Index.

The Mind Centering category of Health Index 955 is designed to help users monitor the parameters relating to time spent engaging in certain activities which allow the body to achieve a state of profound relaxation while the mind becomes focused, and is based upon both data input by the user and data sensed by the monitoring device 10. In particular, a user may input the beginning and end times of relaxation activities such as yoga or meditation. The quality of those activities as determined by the depth of a mind centering event can be measured by monitoring parameters including skin temperature, heart rate, respiration rate, and heat flow as sensed by monitoring device 10. Percent change in GSR as derived either by monitoring device 10 or monitoring system 32 may also be utilized.

The Mind Centering Health Index piston level is preferably calculated with respect to a suggested healthy daily routine that includes participating each day in an activity that allows the body to achieve profound relaxation while the mind stays highly focused for at least fifteen minutes. Parameters utilized in the calculation of the relevant piston level include the amount of time spent in a mind centering activity, and the percent change in skin temperature, heart rate, respiration rate, heat flow or GSR as sensed by monitoring device 10 compared to a baseline which is an indication of the depth or quality of the mind centering activity.

Figure 26:
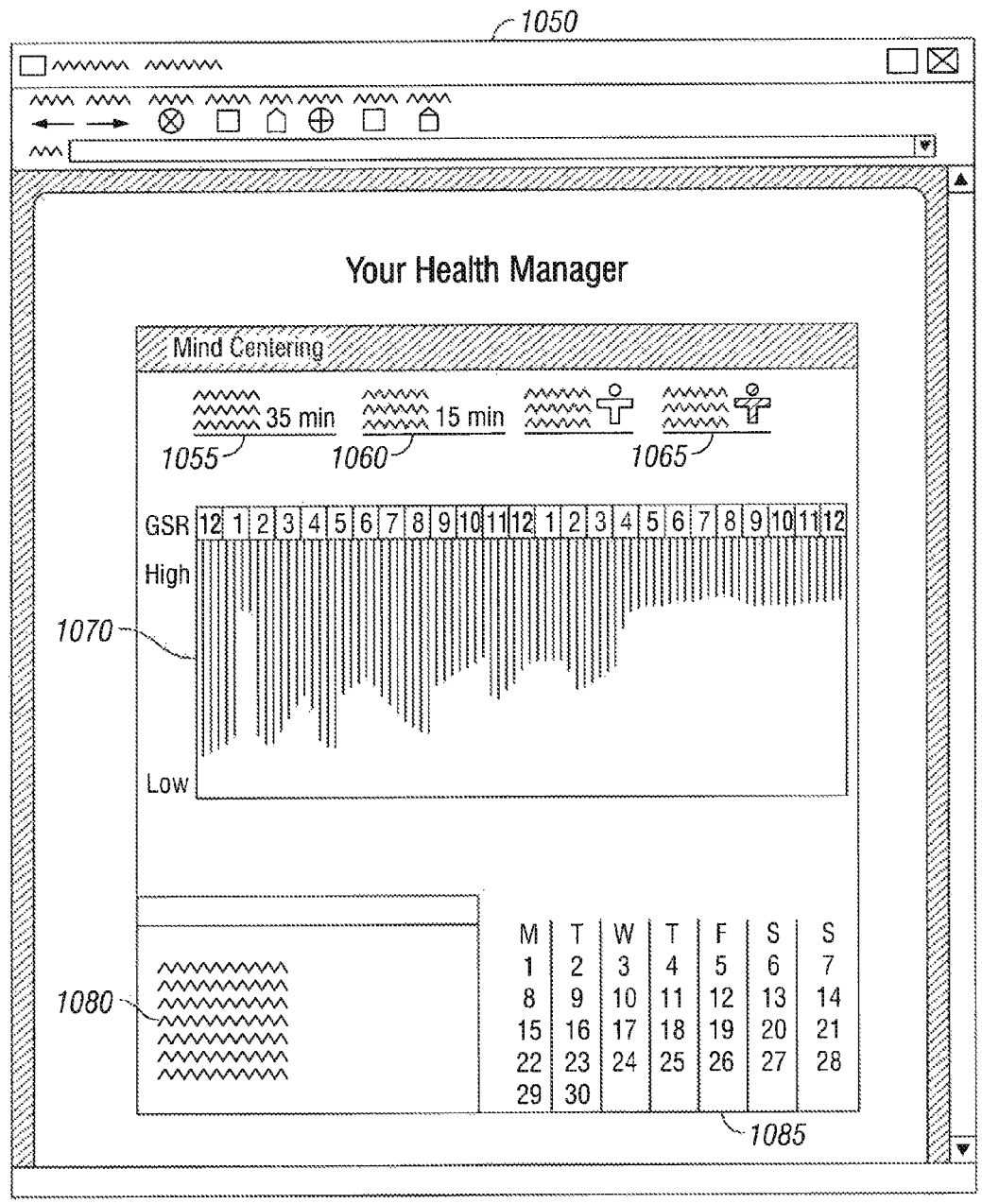
FIG. 26 is a representation of an embodiment of the mind centering web page according to an aspect of the present invention.

Information regarding the time spent on self-reflection and relaxation is presented to the user through mind centering web page 1050 shown in FIG. 26. For each mind centering activity, referred to as a session, the preferred mind centering web page 1050 includes the time spent during the session, shown at 1055, the target time, shown at 1060, comparison section 1065 showing target and actual depth of mind centering, or focus, and a histogram 1070 that shows the overall level of stress derived from such things as skin temperature, heart rate, respiration rate, heat flow and/or GSR. In comparison section 1065, the human figure outline showing target focus is solid, and the human figure outline showing actual focus ranges from fuzzy to solid depending on the level of focus. The preferred mind centering web page may also include an indication of the total time spent on mind centering activities, shown at 1075, hyperlinks 1080 which allow the user to directly access relevant news items and articles, suggestions for refining or improving daily routine with respect to mind centering and affiliate advertising, and a calendar 1085 for choosing among views having variable and selectable time periods. The items shown at 1080 may be selected and customized based on information learned about the individual in the survey and on their performance as measured by the Health Index.

The Sleep category of Health Index 955 is designed to help users monitor their sleep patterns and the quality of their sleep. It is intended to help users learn about the importance of sleep in their healthy lifestyle and the relationship of sleep to circadian rhythms, being the normal daily variations in body functions. The Sleep category is based upon both data input by the user and data sensed by monitoring device 10. The data input by the user for each relevant time interval includes the times the user went to sleep and woke up and a rating of the quality of sleep. The data from monitoring device 10 that is relevant includes skin temperature, heat flow, beat-to-beat heart variability, heart rate, pulse rate, respiration rate, core temperature, galvanic skin response, EMG, EEG, EOG, blood pressure, and oxygen consumption. Also relevant is ambient sound and body movement or motion as detected by a device such as an accelerometer. This data can then be used to calculate or derive sleep onset and wake time, sleep interruptions, and the quality and depth of sleep.

The Sleep Health Index piston level is determined with respect to a healthy daily routine including getting a minimum amount, preferably eight hours, of sleep each night and having a predictable bed time and wake time. The specific parameters which determine the piston level calculation include the number of hours of sleep per night and the bed time and wake time as sensed by monitoring device 10 or as input by the user, and the quality of the sleep as rated by the user or derived from other data.

Figure 27:
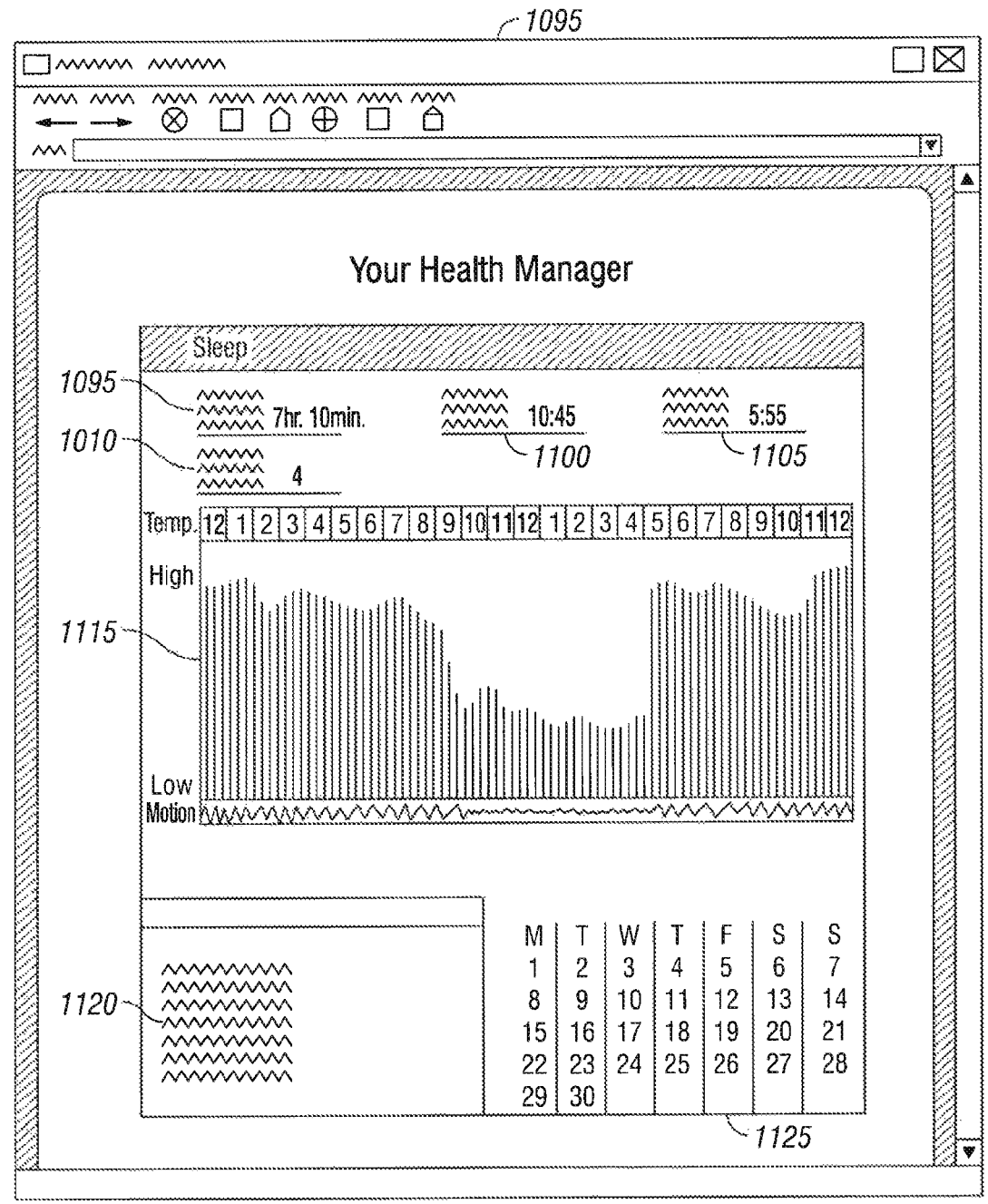
FIG. 27 is a representation of an embodiment of the sleep web page according to an aspect of the present invention.

Information regarding sleep is presented to the user through sleep web page 1090 shown in FIG. 27. Sleep web page 1090 includes a sleep duration indicator 1095, based on either data from monitoring device 10 or on data input by the user, together with user sleep time indicator 1100 and wake time indicator 1105. A quality of sleep rating 1110 input by the user may also be utilized and displayed. If more than a one day time interval is being displayed on sleep web page 1090, then sleep duration indicator 1095 is calculated and displayed as a cumulative value, and sleep time indicator 1100, wake time indicator 1105 and quality of sleep rating 1110 are calculated and illustrated as averages. Sleep web page 1090 also includes a user-selectable sleep graph 1115 which calculates and displays one sleep related parameter over a pre-selected time interval. For illustrative purposes, FIG. 27 shows heat flow over a one-day period, which tends to be lower during sleeping hours and higher during waking hours. From this information, a person's biorhythms can be derived. Sleep graph 1115 may also include a graphical representation of data from an accelerometer incorporated in monitoring device 10 which monitors the movement of the body. The sleep web page 1090 may also include hyperlinks 1120 which allow the user to directly access sleep related news items and articles, suggestions for refining or improving daily routine with respect to sleep and affiliate advertising available elsewhere on the network, and a sleep calendar 1125 for choosing a relevant time interval. The items shown at 1120 may be selected and customized based on information learned about the individual in the survey and on their performance as measured by the Health Index.

The Activities of Daily Living category of Health Index 955 is designed to help users monitor certain health and safety related activities and risks and is based entirely on data input by the user. The Activities of Daily Living category is divided into four sub-categories: personal hygiene, which allows the user to monitor activities such as brushing and flossing his or her teeth and showering; health maintenance, that tracks whether the user is taking prescribed medication or supplements and allows the user to monitor tobacco and alcohol consumption and automobile safety such as seat belt use; personal time, that allows the user to monitor time spent socially with family and friends, leisure, and mind centering activities; and responsibilities, that allows the user to monitor certain work and financial activities such as paying bills and household chores.

The Activities of Daily Living Health Index piston level is preferably determined with respect to the healthy daily routine described below. With respect to personal hygiene, the routine requires that the users shower or bathe each day, brush and floss teeth each day, and maintain regular bowel habits. With respect to health maintenance, the routine requires that the user take medications and vitamins and/or supplements, use a seat belt, refrain from smoking, drink moderately, and monitor health each day with the Health Manager. With respect to personal time, the routine requires the users to spend at least one hour of quality time each day with family and/or friends, restrict work time to a maximum of nine hours a day, spend some time on leisure or play activity each day, and engage in a mind stimulating activity. With respect to responsibilities, the routine requires the users to do household chores, pay bills, be on time for work, and keep appointments. The piston level is calculated based on the degree to which the user completes a list of daily activities as determined by information input by the user.

Figure 28:
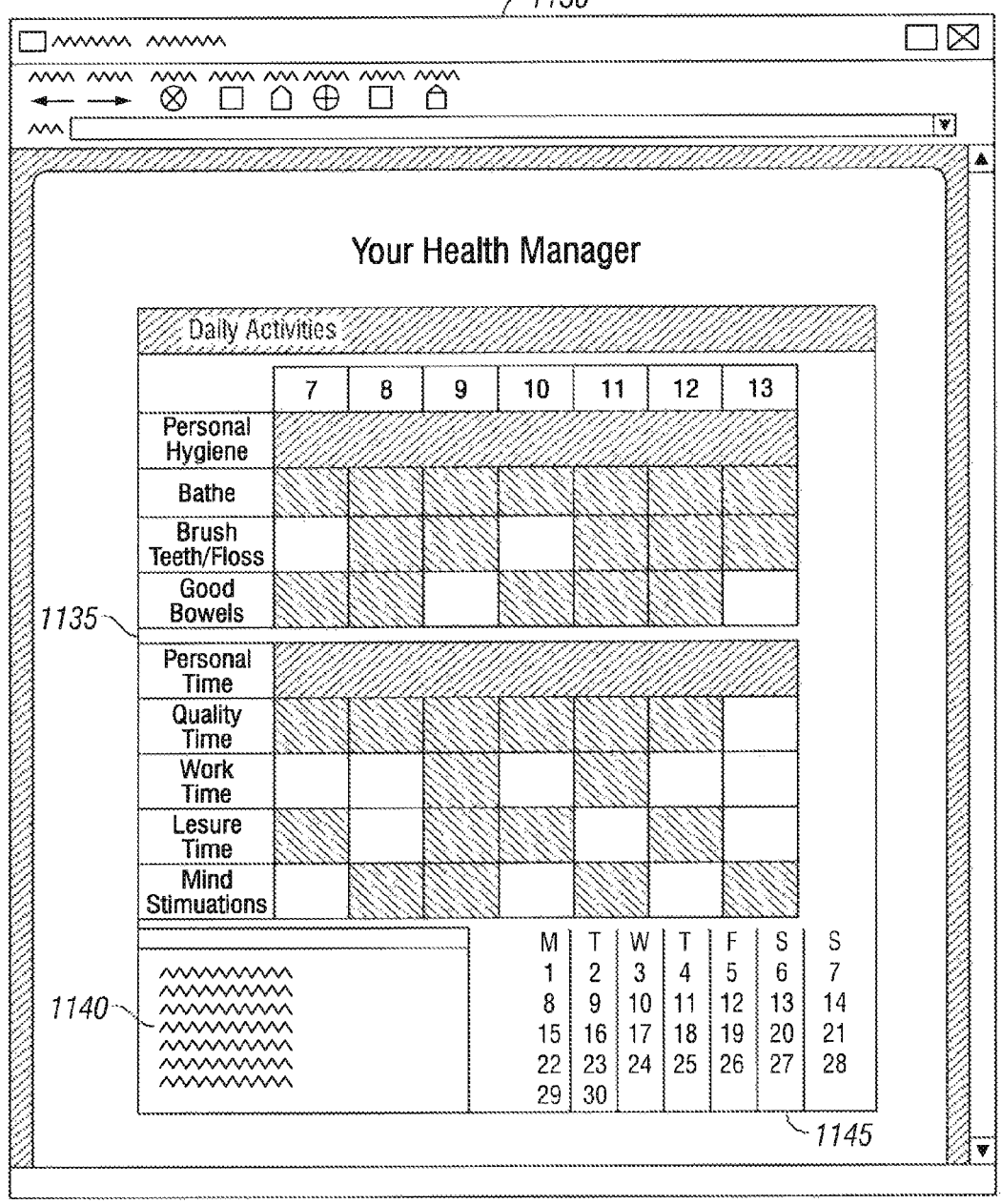
FIG. 28 is a representation of an embodiment of the daily activities web page according to an aspect of the present invention.

Information relating to these activities is presented to the user through daily activities web page 1130 shown in FIG. 28. In preferred daily activities web page 1130, activities chart 1135, selectable for one or more of the sub-categories, shows whether the user has done what is required by the daily routine. A colored or shaded box indicates that the user has done the required activity, and an empty, non-colored or shaded box indicates that the user has not done the activity. Activities chart 1135 can be created and viewed in selectable time intervals. For illustrative purposes, FIG. 28 shows the personal hygiene and personal time sub-categories for a particular week. In addition, daily activities web page 1130 may include daily activity hyperlinks 1140 which allow the user to directly access relevant news items and articles, suggestions for improving or refining daily routine with respect to activities of daily living and affiliate advertising, and a daily activities calendar 1145 for selecting a relevant time interval. The items shown at 1140 may be selected and customized based on information learned about the individual in the survey and on their performance as measured by the Health Index.

The How You Feel category of Health Index 955 is designed to allow users to monitor their perception of how they felt on a particular day, and is based on information, essentially a subjective rating, that is input directly by the user. A user provides a rating, preferably on a scale of 1 to 5, with respect to the following nine subject areas: mental sharpness; emotional and psychological wellbeing; energy level; ability to cope with life stresses; appearance; physical wellbeing; self-control; motivation; and comfort in relating to others. Those ratings are averaged and used to calculate the relevant piston level.

Figure 11:
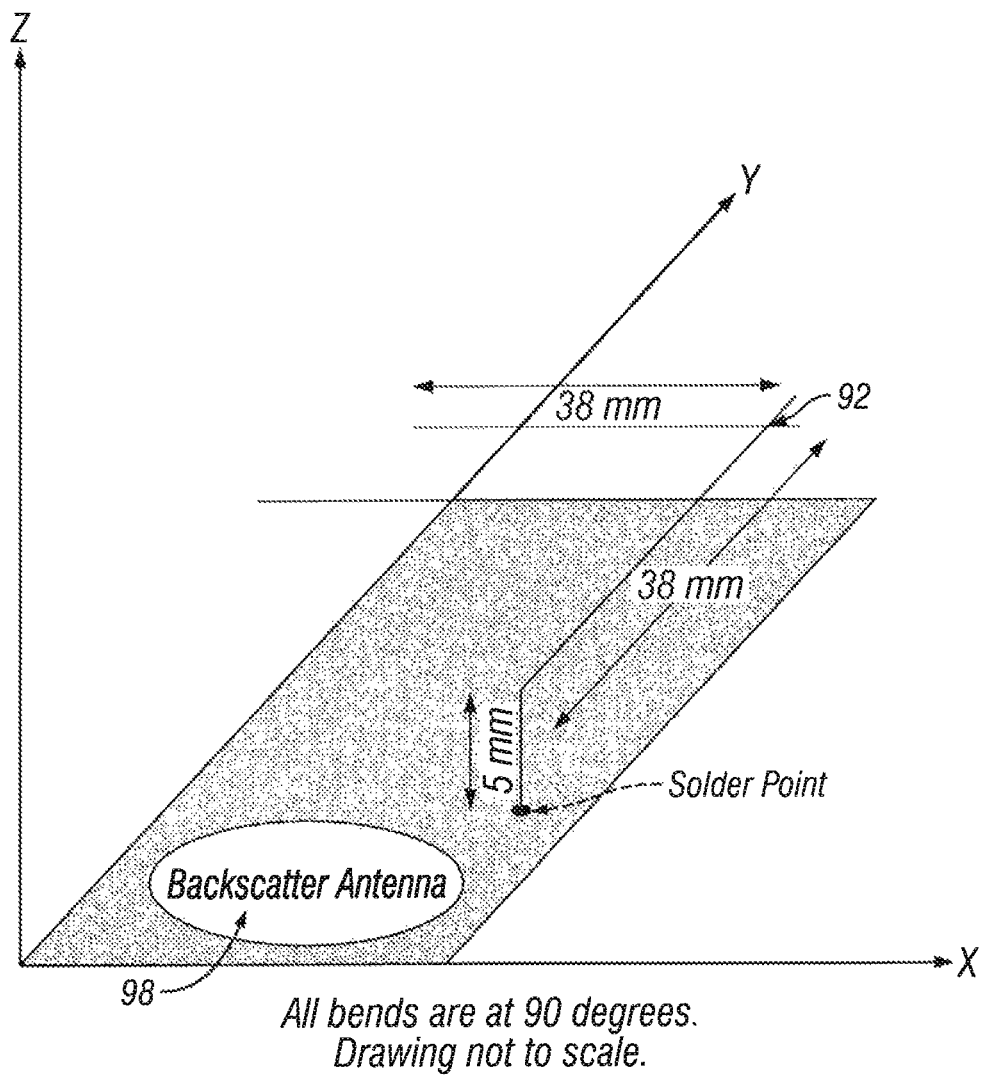
FIG. 11 is a diagram of the active RF and RF backscatter antennas.
Figure 29:
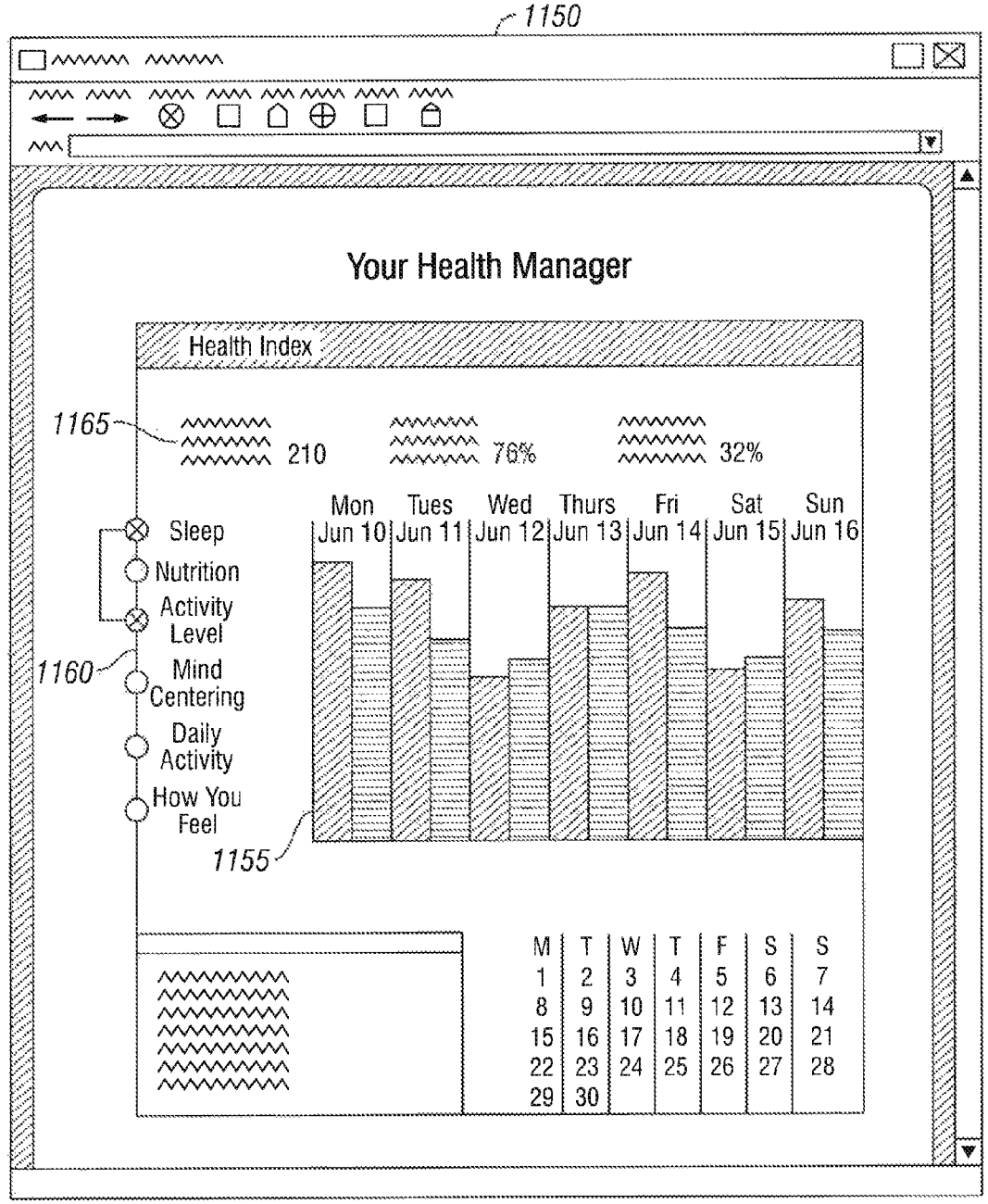
FIG. 29 is a representation of an embodiment of the Health Index web page according to an aspect of the present invention.

Referring to FIG. 29, Health Index web page 1150 is shown. Health Index web page 1150 enables users to view the performance of their Health Index over a user selectable time interval including any number of consecutive or non-consecutive days. Using Health Index selector buttons 1160, the user can select to view the Health Index piston levels for one category, or can view a side-by-side comparison of the Health Index piston levels for two or more categories. For example, a user might want to just turn on Sleep to see if their overall sleep rating improved over the previous month, much in the same way they view the performance of their favorite stock. Alternatively, Sleep and Activity Level might be simultaneously displayed in order to compare and evaluate Sleep ratings with corresponding Activity Level ratings to determine if any day-today correlations exist. Nutrition ratings might be displayed with How You Feel for a pre-selected time interval to determine if any correlation exists between daily eating habits and how they felt during that interval. For illustrative purposes, FIG. 11 illustrates a comparison of Sleep and Activity Level piston levels for the week of June 10 through June 16. Health Index web page 1150 also includes tracking calculator 1165 that displays access information and statistics such as the total number of days the user has logged in and used the Health Manager, the percentage of days the user has used the Health Manager since becoming a subscriber, and percentage of time the user has used the monitoring device 10 to gather data.

Referring again to FIG. 23, opening Health Manager web page 950 may include a plurality of user selectable category summaries 956a through 956f, one corresponding to each of the Health Index 955 categories. Each category summary 956a through 956f presents a pre-selected filtered subset of the data associated with the corresponding category. Nutrition category summary 956a displays daily target and actual caloric intake. Activity Level category summary 956b displays daily target and actual calories burned. Mind Centering category summary 956c displays target and actual depth of mind centering or focus. Sleep category summary 956d displays target sleep, actual sleep, and a sleep quality rating. Daily Activities category summary 956e displays a target and actual score based on the percentage of suggested daily activities that are completed. The How You Feel category summary 956f shows a target and actual rating for the day.

Opening Health Manager web page 950 also may include Daily Dose section 957 which provides, on a daily time interval basis, information to the user, including, but not limited to, hyperlinks to news items and articles, commentary and reminders to the user based on tendencies, such as poor nutritional habits, determined from the initial survey. The commentary for Daily Dose 957 may, for example, be a factual statement that drinking 8 glasses of water a day can reduce the risk of colon cancer by as much as 32%, accompanied by a suggestion to keep a cup of water by your computer or on your desk at work and refill often. Opening Health Manager web page 950 also may include a Problem Solver section 958 that actively evaluates the user's performance in each of the categories of Health Index 955 and presents suggestions for improvement. For example, if the system detects that a user's Sleep levels have been low, which suggest that the user has been having trouble sleeping, Problem Solver 958 can provide suggestions for way to improve sleep. Problem Solver 958 also may include the capability of user questions regarding improvements in performance. Opening Health Manager web page 950 may also include a Daily Data section 959 that launches an input dialog box. The input dialog box facilitates input by the user of the various data required by the Health Manager. As is known in the art, data entry may be in the form of selection from pre-defined lists or general free form text input. Finally, opening Health Manager web page 950 may include Body Stats section 961 which may provide information regarding the user's height, weight, body measurements, body mass index or BMI, and vital signs such as heart rate, blood pressure or any of the identified physiological parameters.

Figure 30:
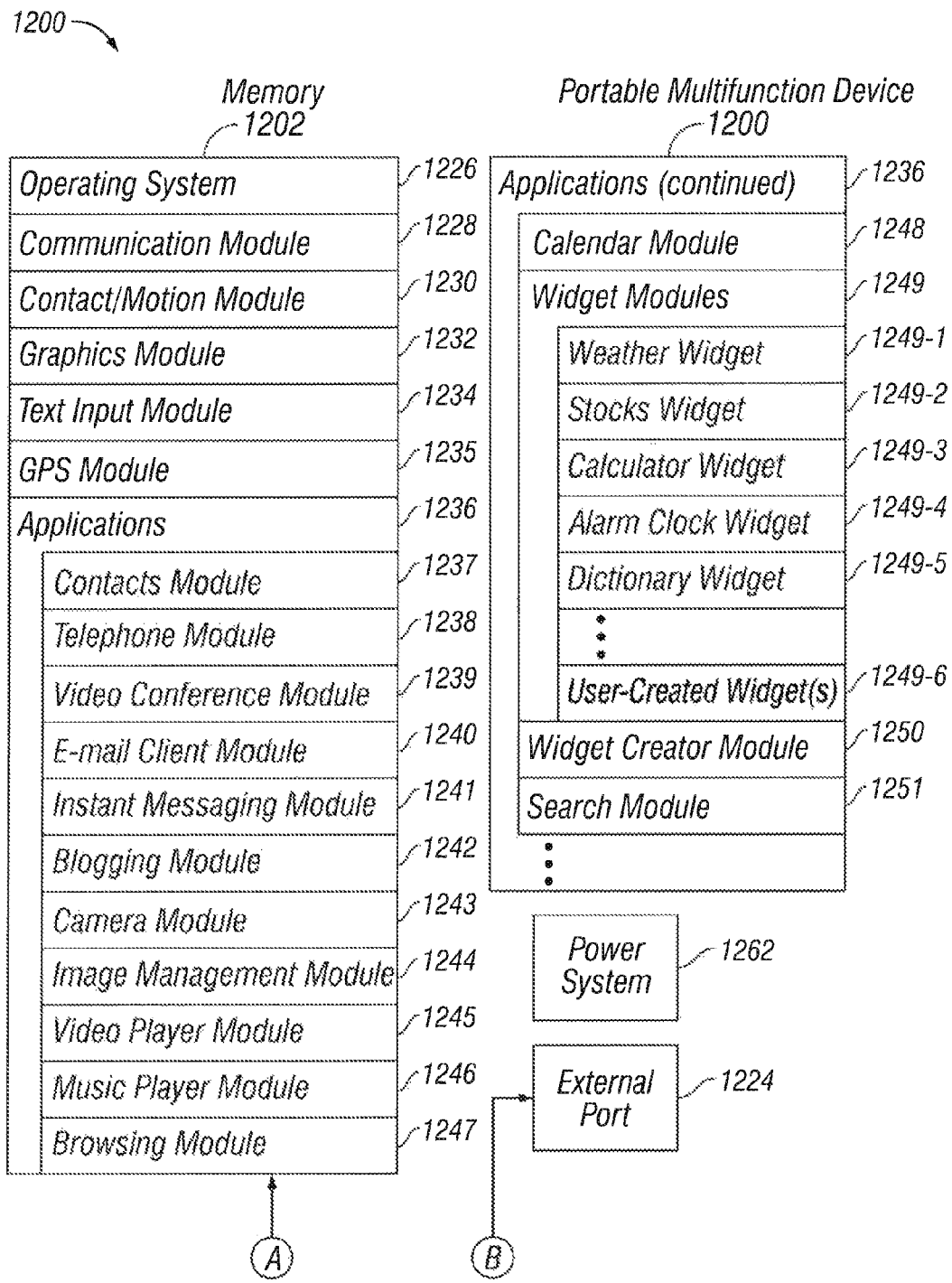
FIG. 30 is a block diagrams\illustrating portable multi-function devices with touch-sensitive displays in accordance with some embodiments.
Figure 30:
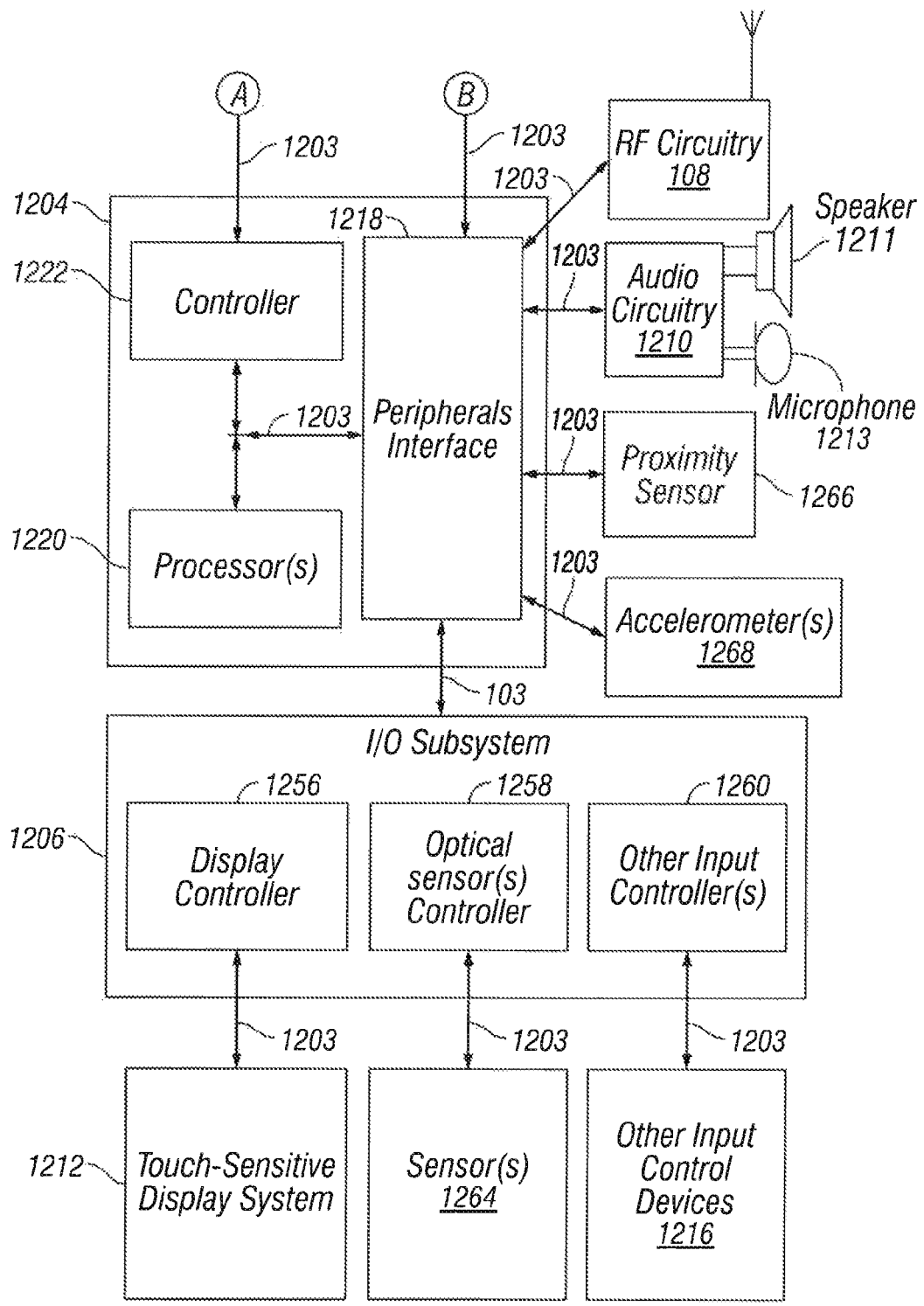

FIG. 30 is a block diagram illustrating embodiments of a mobile device 1200 for obtaining monitored information about an individual. The mobile device 1200 can include a display 1212 that can be a touch sensitive display. In one embodiment, the mobile device 1200 is monitoring device 10 with mobile device components, and is used for obtaining monitored information about an individual The touch-sensitive display 1212 is sometimes called a "touch screen" for convenience, and may also be known as or called a touch-sensitive display system. The mobile device 1200 may include a memory 1202 (which may include one or more computer readable storage mediums), a memory controller 1222, one or more processing units (CPU's) 1220, a peripherals interface 1218, Network Systems circuitry 1208, including but not limited to RF circuitry, audio circuitry 1210, a speaker 1211, a microphone 1213, an input/output (I/O) subsystem 1206, other input or control devices 1216, and an external port 124. The mobile device 1200 may include one or more optical sensors 1264. These components may communicate over one or more communication buses or signal lines 1203.

It should be appreciated that the mobile device 1200 is only one example of a portable multifunction mobile device 1200, and that the mobile device 1200 may have more or fewer components than shown, may combine two or more components, or a may have a different configuration or arrangement of the components. The various components shown in FIG. 30 may be implemented in hardware, software or a combination of both hardware and software, including one or more signal processing and/or application specific integrated circuits.

Memory 1202 may include high-speed random access memory and may also include non-volatile memory, such as one or more magnetic disk storage devices, flash memory devices, or other non-volatile solid-state memory devices. Access to memory 1202 by other components of the mobile device 1200, such as the CPU 1220 and the peripherals interface 1218, may be controlled by the memory controller 1222.

The peripherals interface 1218 couples the input and output peripherals of the device to the CPU 1220 and memory 1202. The one or more processors 1220 run or execute various software programs and/or sets of instructions stored in memory 1202 to perform various functions for the mobile device 1200 and to process data.

In some embodiments, the peripherals interface 1218, the CPU 1220, and the memory controller 1222 may be implemented on a single chip, such as a chip 1204. In some other embodiments, they may be implemented on separate chips.

The Network System circuitry 1208 receives and sends signals, including but not limited to RF, also called electromagnetic signals. The Network System circuitry 1208 converts electrical signals to/from electromagnetic signals and communicates with communications networks and other communications devices via the electromagnetic signals. The Network Systems circuitry 1208 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The Network Systems circuitry 1208 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), BLUETOOTH®, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

The audio circuitry 1210, the speaker 1211, and the microphone 1213 provide an audio interface between a user and the mobile device 1200. The audio circuitry 1210 receives audio data from the peripherals interface 1218, converts the audio data to an electrical signal, and transmits the electrical signal to the speaker 1211. The speaker 1211 converts the electrical signal to human-audible sound waves. The audio circuitry 1210 also receives electrical signals converted by the microphone 1213 from sound waves. The audio circuitry 1210 converts the electrical signal to audio data and transmits the audio data to the peripherals interface 1218 for processing. Audio data may be retrieved from and/or transmitted to memory 1202 and/or the Network Systems circuitry 1208 by the peripherals interface 1218. In some embodiments, the audio circuitry 1210 also includes a headset jack (e.g. 1212, FIG. 31). The headset jack provides an interface between the audio circuitry 1210 and removable audio input/output peripherals, such as output-only headphones or a headset with both output (e.g., a headphone for one or both ears) and input (e.g., a microphone).

The I/O subsystem 1206 couples input/output peripherals on the mobile device 1200, such as the touch screen 1212 and other input/control devices 1216, to the peripherals interface 1218. The I/O subsystem 1206 may include a display controller 1256 and one or more input controllers 1260 for other input or control devices. The one or more input controllers 1260 receive/send electrical signals from/to other input or control devices 1216. The other input/control devices 1216 may include physical buttons (e.g., push buttons, rocker buttons, etc.), dials, slider switches, joysticks, click wheels, and so forth. In some alternate embodiments, input controller(s) 1260 may be coupled to any (or none) of the following: a keyboard, infrared port, USB port, and a pointer device such as a mouse. The one or more buttons (e.g., 1208, FIG. 31) may include an up/down button for volume control of the speaker 1211 and/or the microphone 1213. The one or more buttons may include a push button (e.g., 206, FIG. 31). A quick press of the push button may disengage a lock of the touch screen 1212 or begin a process that uses gestures on the touch screen to unlock the device, as described in U.S. patent application Ser. No. 11/322,549, "Unlocking a Device by Performing Gestures on an Unlock Image," filed Dec. 23, 2005, which is hereby incorporated by reference in its entirety. A longer press of the push button may turn power to the mobile device 1200 on or off. The user may be able to customize a functionality of one or more of the buttons. The touch screen 1212 is used to implement virtual or soft buttons and one or more soft keyboards.

The touch-sensitive touch screen 1212 provides an input interface and an output interface between the device and a user. The display controller 1256 receives and/or sends electrical signals from/to the touch screen 1212. The touch screen 1212 displays visual output to the user. The visual output may include graphics, text, icons, video, and any combination thereof (collectively termed "graphics"). In some embodiments, some or all of the visual output may correspond to user-interface objects, further details of which are described below.

A touch screen 1212 has a touch-sensitive surface, sensor or set of sensors that accepts input from the user based on haptic and/or tactile contact. The touch screen 1212 and the display controller 1256 (along with any associated modules and/or sets of instructions in memory 1202) detect contact (and any movement or breaking of the contact) on the touch screen 1212 and converts the detected contact into interaction with user-interface objects (e.g., one or more soft keys, icons, web pages or images) that are displayed on the touch screen. In an exemplary embodiment, a point of contact between a touch screen 1212 and the user corresponds to a finger of the user.

The touch screen 1212 may use LCD (liquid crystal display) technology, or LPD (light emitting polymer display) technology, although other display technologies may be used in other embodiments. The touch screen 1212 and the display controller 1256 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 1212.

A touch-sensitive display in some embodiments of the touch screen 1212 may be analogous to the multi-touch sensitive tablets described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in their entirety. However, a touch screen 1212 displays visual output from the portable mobile device 1200, whereas touch sensitive tablets do not provide visual output.

A touch-sensitive display in some embodiments of the touch screen 1212 may be as described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

The touch screen 1212 may have a resolution in excess of 1000 dpi. In an exemplary embodiment, the touch screen has a resolution of approximately 1060 dpi. The user may make contact with the touch screen 1212 using any suitable object or appendage, such as a stylus, a finger, and so forth. In some embodiments, the user interface is designed to work primarily with finger-based contacts and gestures, which are much less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, the mobile device 1200 may include a touchpad (not shown) for activating or deactivating particular functions. In some embodiments, the touchpad is a touch-sensitive area of the device that, unlike the touch screen, does not display visual output. The touchpad may be a touch-sensitive surface that is separate from the touch screen 1212 or an extension of the touch-sensitive surface formed by the touch screen.

In some embodiments, the mobile device 1200 may include a physical or virtual click wheel as an input control device 1216. A user may navigate among and interact with one or more graphical objects (henceforth referred to as icons) displayed in the touch screen 1212 by rotating the click wheel or by moving a point of contact with the click wheel (e.g., where the amount of movement of the point of contact is measured by its angular displacement with respect to a center point of the click wheel). The click wheel may also be used to select one or more of the displayed icons. For example, the user may press down on at least a portion of the click wheel or an associated button. User commands and navigation commands provided by the user via the click wheel may be processed by an input controller 1260 as well as one or more of the modules and/or sets of instructions in memory 1202. For a virtual click wheel, the click wheel and click wheel controller may be part of the touch screen 1212 and the display controller 1256, respectively. For a virtual click wheel, the click wheel may be either an opaque or semitransparent object that appears and disappears on the touch screen display in response to user interaction with the device. In some embodiments, a virtual click wheel is displayed on the touch screen of a portable multifunction device and operated by user contact with the touch screen.

The mobile device 1200 also includes a power system 1262 for powering the various components. The power system 1262 may include a power management system, one or more power sources (e.g., battery 24, alternating current (AC)), a recharging system, a power failure detection circuit, a power converter or inverter, a power status indicator (e.g., a light-emitting diode (LED)) and any other components associated with the generation, management and distribution of power in portable devices.

The mobile device 1200 may also include one or more sensors 14, including not limited to optical sensors 1264. FIG. 30 illustrates how an optical sensor coupled to an optical sensor controller 1258 in I/O subsystem 1206. The optical sensor 1264 may include charge-coupled device (CCD) or complementary metal-oxide semiconductor (CMOS) phototransistors. The optical sensor 1264 receives light from the environment, projected through one or more lens, and converts the light to data representing an image. In conjunction with an imaging module 1243 (also called a camera module), the optical sensor 1264 may capture still images or video. In some embodiments, an optical sensor is located on the back of the mobile device 1200, opposite the touch screen display 1212 on the front of the device, so that the touch screen display may be used as a viewfinder for either still and/or video image acquisition. In some embodiments, an optical sensor is located on the front of the device so that the user's image may be obtained for videoconferencing while the user views the other video conference participants on the touch screen display. In some embodiments, the position of the optical sensor 1264 can be changed by the user (e.g., by rotating the lens and the sensor in the device housing) so that a single optical sensor 1264 may be used along with the touch screen display for both video conferencing and still and/or video image acquisition.

The mobile device 1200 may also include one or more proximity sensors 1266. In one embodiment, the proximity sensor 1266 is coupled to the peripherals interface 1218. Alternately, the proximity sensor 1266 may be coupled to an input controller 1260 in the I/O subsystem 1206. The proximity sensor 1266 may perform as described in U.S. patent application Ser. No. 11/241,839, "Proximity Detector In Handheld Device," filed Sep. 30, 2005; Ser. No. 11/240,788, "Proximity Detector In Handheld Device," filed Sep. 30, 2005; Ser. No. 11/620,702, "Using Ambient Light Sensor To Augment Proximity Sensor Output"; Ser. No. 11/586,862, "Automated Response To And Sensing Of User Activity In Portable Devices," filed Oct. 24, 2006; and Ser. No. 11/638,251, "Methods And Systems For Automatic Configuration Of Peripherals," which are hereby incorporated by reference in their entirety. In some embodiments, the proximity sensor turns off and disables the touch screen 1212 when the multifunction device is placed near the user's ear (e.g., when the user is making a phone call). In some embodiments, the proximity sensor keeps the screen off when the device is in the user's pocket, purse, or other dark area to prevent unnecessary battery drainage when the device is a locked state.

The mobile device 1200 may also include one or more accelerometers 1268. FIG. 30 shows an accelerometer 1268 coupled to the peripherals interface 1218. Alternately, the accelerometer 1268 may be coupled to an input controller 1260 in the I/O subsystem 1206. The accelerometer 1268 may perform as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are which are incorporated by reference in their entirety. In some embodiments, information is displayed on the touch screen display in a portrait view or a landscape view based on an analysis of data received from the one or more accelerometers.

In some embodiments, the software components stored in memory 1202 may include an operating system 1226, a communication module (or set of instructions) 1228, a contact/motion module (or set of instructions) 1230, a graphics module (or set of instructions) 1232, a text input module (or set of instructions) 1234, a Global Positioning System (GPS) module (or set of instructions) 1235, and applications (or set of instructions) 1236.

The operating system 1226 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

The communication module 1228 facilitates communication with other devices over one or more external ports 1224 and also includes various software components for handling data received by the Network Systems circuitry 1208 and/or the external port 1224. The external port 1224 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with the 30-pin connector used on iPod (trademark of Apple Computer, Inc.) devices.

The contact/motion module 1230 may detect contact with the touch screen 1212 (in conjunction with the display controller 1256) and other touch sensitive devices (e.g., a touchpad or physical click wheel). The contact/motion module 1230 includes various software components for performing various operations related to detection of contact, such as determining if contact has occurred, determining if there is movement of the contact and tracking the movement across the touch screen 1212, and determining if the contact has been broken (i.e., if the contact has ceased). Determining movement of the point of contact may include determining speed (magnitude), velocity (magnitude and direction), and/or an acceleration (a change in magnitude and/or direction) of the point of contact. These operations may be applied to single contacts (e.g., one finger contacts) or to multiple simultaneous contacts (e.g., "multitouch"/multiple finger contacts). In some embodiments, the contact/motion module 1230 and the display controller 1256 also detects contact on a touchpad. In some embodiments, the contact/motion module 1230 and the controller 1260 detects contact on a click wheel.

The graphics module 1232 includes various known software components for rendering and displaying graphics on the touch screen 1212, including components for changing the intensity of graphics that are displayed. As used herein, the term "graphics" includes any object that can be displayed to a user, including without limitation text, web pages, icons (such as user-interface objects including soft keys), digital images, videos, animations and the like. An animation in this context is a display of a sequence of images that gives the appearance of movement, and informs the user of an action that has been performed (such as moving an email message to a folder). In this context, a respective animation that confirms an action by the user of the device typically takes a predefined, finite amount of time, such as an amount of time between 0.2 and 10.0 seconds, or between 0.5 and 2.0 seconds, depending on the context.

The text input module 1234, which may be a component of graphics module 1232, provides soft keyboards for entering text in various applications (e.g., contacts 1237, e-mail 1240, IM 1241, blogging 1242, browser 1247, and any other application that needs text input).

The GPS module 1235 determines the location of the device and provides this information for use in various applications (e.g., to telephone 1238 for use in location-based dialing, to camera 1243 and/or blogger 1242 as picture/video metadata, and to applications that provide location-based services such as weather widgets, local yellow page widgets, and map/navigation widgets).

The applications 1236 may include the following modules (or sets of instructions), or subset or superset thereof: contacts module 1237 (sometimes called an address book or contact list); telephone module 1238; video conferencing module 1239; mail client module 1240; an instant messaging (IM) module 1241; blogging module 1242; a camera module 1243 for still and/or video images; image management module 1244; video player module 1245; music player module 1246; browser module 1247; c lend r module 1248; widget modules 1249, which m y include weather widget 1249-1, stocks widget 1249-2, calculator widget 1249-3, alarm clock widget 1249-4, dictionary widget 1249-5, and other widgets obtained by the user, as well as user-created widgets 1249-6; widget creator module 1250 for making user-created widgets 1249-6; search module 1251; video and music player module 1252, which merges video player module 1245 and music player module 1246; notes module 1253; and/or map module 1254.

Examples of other applications 1236 that may be stored in memory 1202 include other word processing applications, JAVA-enabled applications, encryption, digital rights management, voice recognition, and voice replication.

In conjunction with touch screen 1212, display controller 1256, contact module 1230, graphics module 1232, and text input module 1234, the contacts module 1237 may be used to manage an address book or contact list, including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 1238, video conference 1239, e-mail 1240, or IM 1241; and so forth. Embodiments of user interfaces and associated processes using contacts module 1237 are described further below.

In conjunction with Network Systems circuitry 1208, audio circuitry 1210, speaker 1211, microphone 1213, touch screen 1212, display controller 1256, contact module 1230, graphics module 1232, and text input module 1234, the telephone module 1238 may be used to enter a sequence of characters corresponding to a telephone number, access one or more telephone numbers in the address book 1237, modify a telephone number that has been entered, dial a respective telephone number, conduct a conversation and disconnect or hang up when the conversation is completed. As noted above, the wireless communication may use any of a plurality of communications standards, protocols and technologies. Embodiments of user interfaces and associated processes using telephone module 1238 are described further below.

In conjunction with Network Systems circuitry 1208, audio circuitry 1210, speaker 1211, microphone 1213, touch screen 1212, display controller 1256, optical sensor 1264, optical sensor controller 1258, contact module 1230, graphics module 1232, text input module 1234, contact list 1237, and telephone module 1238, the videoconferencing module 1239 may be used to initiate, conduct, and terminate a video conference between a user and one or more other participants.

In conjunction with Network Systems circuitry 1208, touch screen 1212, display controller 1256, contact module 1230, graphics module 1232, and text input module 1234, the e-mail client module 1240 may be used to create, send, receive, and manage e-mail. In conjunction with image management module 1244, the e-mail module 1240 makes it very easy to create and send e-mails with still or video images taken with camera module 1243. Embodiments of user interfaces and associated processes using e-mail module 1240 are described further below.

In conjunction with Network Systems circuitry 1208, touch screen 1212, display controller 1256, contact module 1230, graphics module 1232, and text input module 1234, the instant messaging module 1241 may be used to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages and to view received instant messages. In some embodiments, transmitted and/or received instant messages may include graphics, photos, audio files, video files and/or other attachments as are supported in a MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS). Embodiments of user interfaces and associated processes using instant messaging module 1241 are described further below.

In conjunction with Network Systems circuitry 1208, touch screen 1212, display controller 1256, contact module 1230, graphics module 1232, text input module 1234, image management module 1244, and browsing module 1247, the blogging module 1242 may be used to send text, still images, video, and/or other graphics to a blog (e.g., the user's blog).

In conjunction with touch screen 1212, display controller 1256, optical sensor(s) 1264, optical sensor controller 1258, contact module 1230, graphics module 1232, and image management module 1244, the camera module 1243 may be used to capture still images or video (including a video stream) and store them into memory 1202, modify characteristics of a still image or video, or delete a still image or video from memory 1202. Embodiments of user interfaces and associated processes using camera module 1243 are described further below.

In conjunction with touch screen 1212, display controller 1256, contact module 1230, graphics module 1232, text input module 1234, and camera module 1243, the image management module 1244 may be used to arrange, modify or otherwise manipulate, label, delete, present (e.g., in a digital slide show or album), and store still and/or video images. Embodiments of user interfaces and associated processes using image management module 1244 are described further below.

In conjunction with touch screen 1212, display controller 1256, contact module 1230, graphics module 1232, audio circuitry 1210, and speaker 1211, the video player module 1245 may be used to display, present or otherwise play back videos (e.g., on the touch screen or on an external, connected display via external port 1224). Embodiments of user interfaces and associated processes using video player module 1245 are described further below.

In conjunction with touch screen 1212, display system controller 1256, contact module 1230, graphics module 1232, audio circuitry 1210, speaker 1211, Network Systems circuitry 1208, and browser module 1247, the music player module 1246 allows the user to download and play back recorded music and other sound files stored in one or more file formats, such as MP3 or AAC files. In some embodiments, the mobile device 1200 may include the functionality of an MP3 player, such as an iPod (trademark of Apple Computer, Inc.). Embodiments of user interfaces and associated processes using music player module 1246 are described further below.

In conjunction with Network Systems circuitry 1208, touch screen 1212, display system controller 1256, contact module 1230, graphics module 1232, and text input module 1234, the browser module 1247 may be used to browse the Internet, including searching, linking to, receiving, and displaying web pages or portions thereof, as well as attachments and other files linked to web pages. Embodiments of user interfaces and associated processes using browser module 1247 are described further below.

In conjunction with Network Systems circuitry 1208, touch screen 1212, display system controller 1256, contact module 1230, graphics module 1232, text input module 1234, e-mail module 1240, and browser module 1247, the calendar module 1248 may be used to create, display, modify, and store calendars and data associated with calendars (e.g., calendar entries, to do lists, etc.). Embodiments of user interfaces and associated processes using calendar module 1248 are described further below.

In conjunction with Network Systems circuitry 1208, touch screen 1212, display system controller 1256, contact module 1230, graphics module 1232, text input module 1234, and browser module 1247, the widget modules 1249 are mini-applications that may be downloaded and used by a user (e.g., weather widget 1249-1, stocks widget 1249-2, calculator widget 1249-3, alarm clock widget 1249-4, and dictionary widget 1249-5) or created by the user (e.g., user-created widget 1249-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with Network Systems circuitry 1208, touch screen 1212, display system controller 1256, contact module 1230, graphics module 1232, text input module 1234, and browser module 1247, the widget creator module 1250 may be used by a user to create widgets (e.g., turning a user-specified portion of a web page into a widget).

In conjunction with touch screen 1212, display system controller 1256, contact module 1230, graphics module 1232, and text input module 1234, the search module 1251 may be used to search for text, music, sound, image, video, and/or other files in memory 1202 that match one or more search criteria (e.g., one or more user-specified search terms).

In conjunction with touch screen 1212, display controller 1256, contact module 1230, graphics module 1232, and text input module 1234, the notes module 1253 may be used to create and manage notes, to do lists, and the like.

In conjunction with Network Systems circuitry 1208, touch screen 1212, display system controller 1256, contact module 1230, graphics module 1232, text input module 1234, GPS module 1235, and browser module 1247, the map module 1254 may be used to receive, display, modify, and store maps and data associated with maps (e.g., driving directions; data on stores and other points of interest at or near a particular location; and other location-based data).

Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments. For example, video player module 1245 may be combined with music player module 1246 into a single module (e.g., video and music player module. In some embodiments, memory 1202 may store a subset of the modules and data structures identified above. Furthermore, memory 1202 may store additional modules and data structures not described above.

In some embodiments, the mobile device 1200 is a device where operation of a predefined set of functions on the device is performed exclusively through a touch screen 1212 and/or a touchpad. By using a touch screen and/or a touchpad as the primary input/control device for operation of the mobile device 1200, the number of physical input/control devices (such as push buttons, dials, and the like) on the mobile device 1200 may be reduced.

The predefined set of functions that may be performed exclusively through a touch screen and/or a touchpad include navigation between user interfaces. In some embodiments, the touchpad, when touched by the user, navigates the mobile device 1200 to a main, home, or root menu from any user interface that may be displayed on the mobile device 1200. In such embodiments, the touchpad may be referred to as a "menu button." In some other embodiments, the menu button may be a physical push button or other physical input/control device instead of a touchpad.

Figure 31:
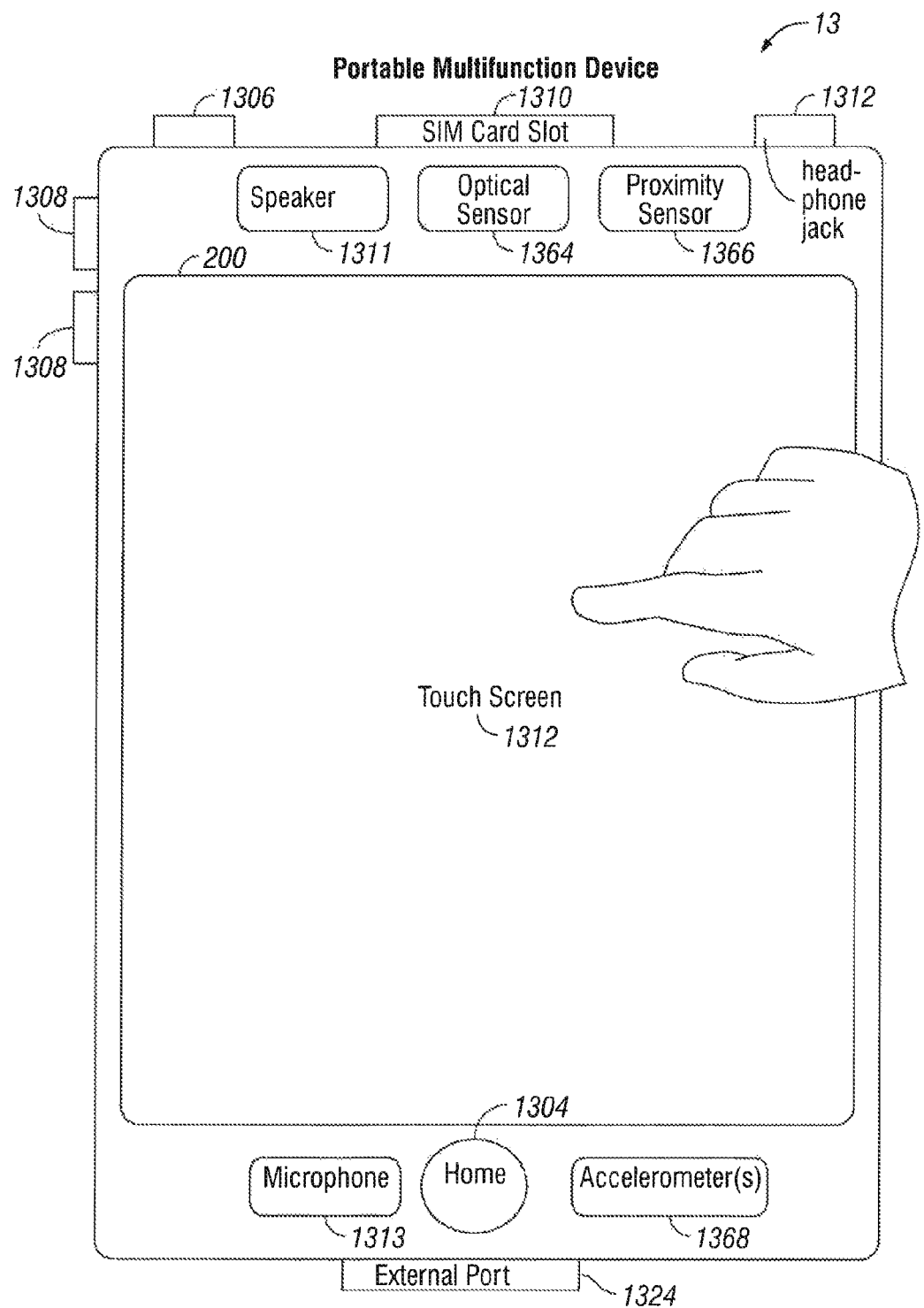
FIG. 31 illustrates one embodiment of a touch screen of a monitoring device used with the present invention.

FIG. 31 illustrates a portable multifunction mobile device 1200 having a touch screen 1212 in accordance with some embodiments. The touch screen may display one or more graphics within user interface (UI) 1200. In this embodiment, as well as others described below, a user may select one or more of the graphics by making contact or touching the graphics, for example, with one or more fingers 1202 (not drawn to scale in the figure). In some embodiments, selection of one or more graphics occurs when the user breaks contact with the one or more graphics. In some embodiments, the contact may include a gesture, such as one or more taps, one or more swipes (from left to right, right to left, upward and/or downward) and/or a rolling of a finger (from right to left, left to right, upward and/or downward) that has made contact with the mobile device 1200. In some embodiments, inadvertent contact with a graphic may not select the graphic. For example, a swipe gesture that sweeps over an application icon may not select the corresponding application when the gesture corresponding to selection is a tap.

The mobile device 1200 may also include one or more physical buttons, such as "home" or menu button 1204. As described previously, the menu button 1204 may be used to navigate to any application 1236 in a set of applications that may be executed on the mobile device 1000. Alternatively, in some embodiments, the menu button is implemented as a soft key in a GUI in touch screen 1212.

In one embodiment, the mobile device 1200 includes a touch screen 1212, a menu button 1204, a push button 1206 for powering the device on/off and locking the device, volume adjustment button(s) 1208, a Subscriber Identity Module (SIM) card slot 1210, a head set jack 1212, and a docking/charging external port 1224. The push button 1206 may be used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, the mobile device 1200 also may accept verbal input for activation or deactivation of some functions through the microphone 1212.

In one embodiment of the present invention, the wearable device is made entirely or partially of silicone rubber, either gum or liquid.

Silicone rubber is highly inert and does not react with most chemicals. silicone rubber chain.

In one embodiment, the silicone rubber is a polysiloxanes with backbones of Si—O—Si units. Polysiloxane is very flexible due to large bond angles and bond lengths when compared to those found in more basic polymers such as polyethylene. For example, a C—C backbone unit has a bond length of 1.54 Å and a bond angle of 112°, whereas the siloxane backbone unit Si—O has a bond length of 1.63 Å and a bond angle of 130°. The following structure is repeated in the silicone rubber.

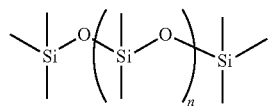

The siloxane backbone has a much more flexible polymer. Because the bond lengths are longer, they can move farther and change conformation easily, making for a flexible material. Polysiloxanes also tend to be chemically inert, due to the strength of the silicon-oxygen bond. Despite silicone being a congener of carbon, silicone analogues of carbonaceous compounds generally exhibit different properties, due to the differences in electronic structure and electronegativity between the two elements; the silicon-oxygen bond in polysiloxanes is significantly more stable than the carbon-oxygen bond in polyoxymethylene (a structurally similar polymer) due to its higher bond energy.

Silicone rubber is an elastomer (rubber-like material) composed of silicone—itself a polymer, containing silicon together with carbon, hydrogen, and oxygen. Silicone rubbers are often one- or two-part polymers, and may contain fillers to improve properties or reduce cost. Silicone rubber is generally non-reactive, stable, and resistant to extreme environments and temperatures from −55° C. to +300° C. while still maintaining its useful properties.

In its uncured state, the silicone rubber used can be a highly-adhesive gel or liquid. To convert it to a solid, it is cured, vulcanized, or catalyzed. In one embodiment, this is normally carried out in a two stage process at the point of manufacture into the desired shape, and then in a prolonged post-cure process. It can also be injection molded. Suitable methods for the injection molding that can be used with the present invention are disclosed in, WO1999056922, EP1785454B1, EP0640663B1, U.S. Publication No. 20130175732, EP2614945A2, EP1172414B1, EP0183553A2, EP1113042A2, EP1555297A1, and EP1595676A4, all incorporated fully herein by reference. In one embodiment, the silicone rubber can also be compression molded.

Silicone rubber's special features as "Organosiloxanes Polymer" have originated from its unique molecular structure that they carry both inorganic and organic rubbers, In other words, due to the Si—O bond of silicone rubber and its inorganic properties, silicone rubber is superior to ordinary organic rubbers in terms of heat resistance, chemical stability, electrical insulating, abrasion resistance, weatherability and ozone resistance, and the like.

Silicone rubber is classified into HTV silicone rubber (High Temperature Vulcanization silicone rubber) and RTV silicone rubber (Room Temperature Vulcanization silicone rubber) by its curing temperature. Also, HTV silicone rubber is divided into Millable Type silicone rubber and Liquid Type silicone rubber by its degree of polymerization.

LSR is Liquid Type and High Temperature Vulcanization silicone rubber. LSR differs from Millable Type silicone rubber and RTV (Room Temperature Vulcanization) by its degree of viscosity and curing temperature. LSR (Liquid silicone rubber) is perfect rubber material for automated injection molding due to its excellent liquidity. Also, LSR (Liquid silicone rubber) is ideal for complex molds, demanding design and tolerance because it can easily fill the most complex part of a mold.

HRS RTV 2K (RTV silicone rubber) is fire-stop material and designed based on silicone rubber's unique characteristics such as high temperature resistance, flame retardant, sound-proofness and air-tightness. HRS RTV 2K (RTV silicone rubber) is two parts and the mixing ratio is 1:1.

The reaction to make chlorosilanes is quite complex and is carried out at a temperature of about 300° C., under pressures typically of 3 bars. The reaction mass needs to be heated in order to obtain reaction, but once the reaction temperature is reached, the reaction becomes exothermic, and consequently requires very stringent temperature control. The reaction is carried out in a fluidized bed reactor and occurs in a solid/gaseous reaction. In order to maximize the reaction efficiency, the solid silicon must be low in other metallic components. The fine residue that is extracted from the process is dependent upon the quality of the silicon going into the process but is generally made up of Cu, Fe, Al, and Ca. Consequently, silicon having low concentrations of these elements is desired for the process.

The preparation of silicone compounds from chlorosilanes is an important synthetic pathway. The most important process to achieve this transformation is the so-called hydrolysis process. In the hydrolysis process the chlorosilanes compounds produced in the Rochow process are reacted with water converting them into a mixture of linear, and cyclic compounds. The exact composition of the Rochow products, the conditions of pH, concentration of water and temperature of hydrolysis determines the exact composition of the hydrolysis produced.

Since the Rochow process produces primarily dimethyldichlorosilane, the reaction of that component with water is shown below;

Hydrolysis of Chlorosilane to Produce HCl and Siloxanediol

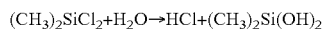

This step results in the formation of hydrochloric acid and a siloxanediol. The corrosive nature of the HCl has to be carefully considered and handled in the plant to avoid corrosion of the equipment.

Dehydration of Siloxanediol to Cyclomethicone and Silanols

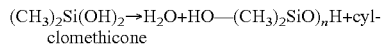

This process results in two types of compounds that are used by the cosmetic chemist. They are silanol (dimethiconol) and cyclomethicone. The former is used in hair gloss compounds and the latter is commonly used in antiperspirant compositions.

In one embodiment, cyclomethicone is distilled from the mixture. The predominate cyclomethicone produced is D4, with lesser amounts of D5 and D3.

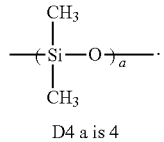

D4 a is 4
D5 a is 5

The ratio of D4 to D5 in the above reaction is generally 85% D4 to 15% D5. The cyclomethicone mixture distills off the hydrolysis process as an azeotrope. This common azeotrope is the least expensive cyclomethicone composition produced. Since separation of the two from each other requires distillation, the pure D4 is more expensive than the azeotrope and the D5 is still more expensive. Cyclomethicone refers to a series of cyclic a silicone compounds. The structure of which is:

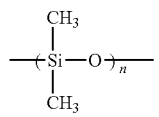

wherein n is an integer ranging from 3 to 30. It is interesting that the terms "volatile silicone" and "cyclomethicone" are sometimes confused. This is because lower cyclomethicone compounds (n is 3-6) are volatile compounds used in applications like antiperspirants and as cleaning solvents for electronic parts like circuit boards. It is important to realize that all cyclomethicone compounds are not volatile (for example n=30), and likewise all volatile silicones are not cyclic (for example MM). The term cyclomethicone refers to a structure; the term cyclomethicone refers to a physical property.

Cyclomethicone is available in a variety of compositions. Pure D3, D4, and D5 are available as well as a more common lower cost 85% D4/15% D5 composition. This becomes important for skin feel and solubility in many solvents. Volatile, cyclomethicone compounds are much more organic soluble than silicone fluids that are higher molecular weight and are linear.

In one embodiment, silanol compounds, also called dimethiconols' can be used with the present invention. These compounds have terminal Si—OH groups present on the molecule. The Si—OH group is reactive toward many organic reactions and is in many regards analogous to the carbanol group CH2-OH. There is one major exception. The silanol groups can homopolymerize under many conditions to produce water and a higher molecular weight silanol. The reaction is as follows:

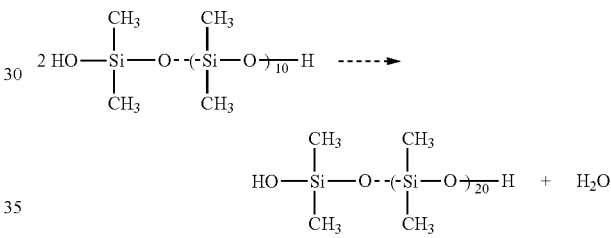

Despite the fact that these materials can homopolymerize under certain conditions, these materials find utilization in a variety of applications, most notable waxes, textiles, and personal care applications.

Silanols are available in a range of viscosity from 5,000 to 50,000 cst. These materials by virtue of their hydroxyl reactive groups are raw materials for a sealant, paints and more recently a series of silanol based esters.

In order to better understand the polymer chemistry, a shorthand has been developed. The nomenclature is based upon the type of groups present in the molecule.

"M unit" is monosubstituted (one oxygen atom on silicon)

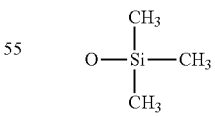

"D unit" is disubstituted (two oxygen atoms on silicon)

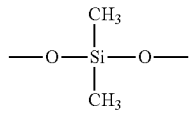

"T unit" is trisubstituted (three oxygen atoms on silicon)

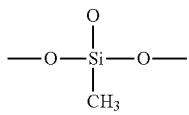

"Q unit" is tetrasubstituted (four oxygen atoms on silicon)

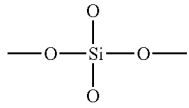

If organofunctional groups other than carbon are introduced, the group is given a "*"
Is added to its designation.

"M* unit" is monosubstituted (one oxygen atom on silicon)

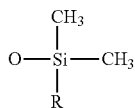

"D* unit" is disubstituted (two oxygen atoms on silicon) with organofunctionality

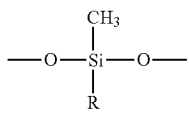

"T* unit" is trisubstituted (three oxygen atoms on silicon) with organofunctionality

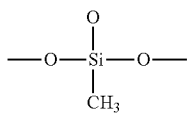

There is no "Q* unit" since there is no possibility of functional groups.

There are three types of construction of silicone polymers. They are:

Comb

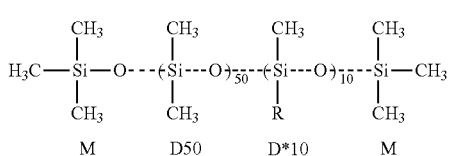

Terminal

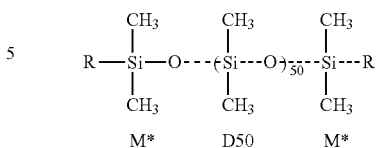

Multifunctional

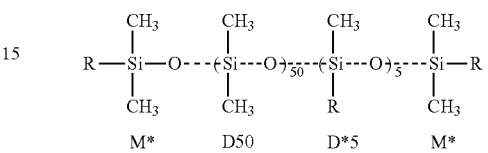

In one embodiment, the silicone fluids used with the present invention are synthesis by the equilibration reaction of MM and cyclomethicone Typical of the synthesis of fluids is the following reaction in which one MM is reacted with one D4 compound to make MD$_4$M, a simple silicone fluid.

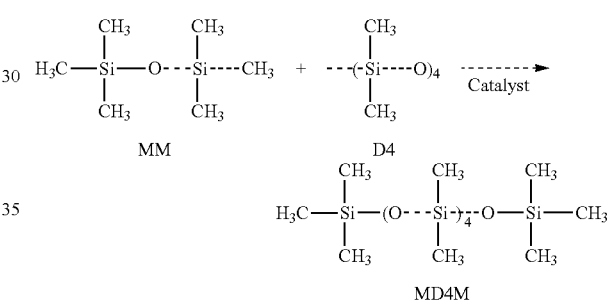

The reaction may be run with either acid or base catalyst. Typically, a catalyst might be sulfuric acid at 2% by weight and the reaction conducted for 12 hours at room temperature. The resulting product is a mixture of about 10% free cyclic and 90% linear fluid. It the catalyst is now neutralized and the cyclic stripped off a stable fluid results. If the catalyst is not neutralized during strip, the fluid will degrade back to MM and D4.

In one embodiment, the equilibration process produces stable silicone fluids, but is also used as a process to introduce functional groups into the polymer.

In one embodiment, a "finished silicone fluid" may be placed in contact with D4 and catalyst and re-equilibrated to make a higher viscosity fluid. Conversely, a "finished silicone fluid" may be re-equilibrated with MM and catalyst to get a lower viscosity fluid. Finally, silicone rubber may be decomposed into MM, and D4 via stripping of the product in the presence of catalyst. This property of silicone polymers makes them decidedly different from organic compounds.

Silicone fluids, also called silicone oils, or simple silicone are sold by their viscosity and range from 0.65 cs to 1,000,000 cs. If the product is not made by blending two different viscosity fluids the viscosity is related to molecular weight. The viscosity allows for an approximate calculation of the value of "n" in the formula below[5].

| Viscosity 25 C (Centistokes) | Approximate Molecular Weight | Approximate "n" Value |
| --- | --- | --- |
| 5 | 800 | 9 |
| 50 | 3,780 | 53 |
| 100 | 6,000 | 85 |
| 200 | 9,430 | 127 |
| 350 | 13,650 | 185 |
| 500 | 17,350 | 230 |
| 1,000 | 28,000 | 375 |
| 10,000 | 67,700 | 910 |
| 60,000 | 116,500 | 1,570 |
| 100,000 | 139,050 | 1,875 |

In one embodiment, the silicone rubber used can be cured by a platinum-catalyzed cure system, a condensation cure system, a peroxide cure system, or an oxide cure system.

In one embodiment, a platinum-based system, also called an addition system is used and two separate components are mixed to catalyze the polymers: the one component contains a platinum complex which must be mixed with the second, a hydride- and a vinyl-functional siloxane polymer, creating an ethyl bridge between the two. Such silicone rubbers cure quickly, though the rate of or even ability to cure is easily inhibited in the presence of elemental tin, sulphur, and many amine compounds.

An example of such a silicone rubber is Silastic Rx, manufactured by Dow Corning.

In one embodiment, a condensation system, also called an RTV (room-temperature vulcanizing) system is used. In this embodiment, an alcoxy crosslinker is exposed to ambient humidity (i.e., water) experiences a hydrolysis step and is left with a hydroxyl group. This group then participates in a condensation reaction with another hydroxyl group attached to the actual polymer. A tin catalyst is not necessary for the reaction to occur, though it increases the rate of the reaction and therefore decreases the cure time. No mixing is required for the reaction to take place. Such a system will cure on its own at room temperature and (unlike the platinum-based system) is not easily inhibited by contact with other chemicals, though it may take as long as a week for the system to fully cure.

In one embodiment, acetoxy tin condensation is used for curing the silicone rubber. In one embodiment, a peroxide-based silicone is used.

In one embodiment, the silicone rubber offers good resistance to extreme temperatures, being able to operate normally from −100° C. to +300° C. Some properties such as elongation, creep, cyclic flexing, tear strength, compression set, dielectric strength (at high voltage), thermal conductivity, fire resistance and in some cases tensile strength can be—at extreme temperatures—far superior to organic rubbers in general, although a few of these properties are still lower than for some specialty materials. Silicone rubber is a material of choice in industry when retention of initial shape and mechanical strength are desired under heavy thermal stress or sub-zero temperatures.

The siloxane bonds (—Si—O—Si—) that form the backbone of silicone (dimethyl polysiloxane) are highly stable. At 433 kJ/mol, their binding energy is higher than that of carbon bonds (C—C), at 355 kJ/mol. Thus, compared to common organic polymers, silicone rubbers have higher heat resistance and chemical stability, and provide better electrical insulation.

The siloxane bonds (—Si—O—Si—) that form the backbone of silicone (dimethyl polysiloxane) are highly stable. At 433 kJ/mol, their binding energy is higher than that of carbon bonds (C—C), at 355 kJ/mol. Thus, compared to common organic polymers, silicone rubbers have higher heat resistance and chemical stability, and provide better electrical insulation.

Silicone rubber withstands high and low temperatures far better than organic rubbers. Silicone rubber can be used indefinitely at 150° C. with almost no change in its properties. It withstands use even at 200° C. for 10,000 hours or more, and some products can withstand heat of 350° C. for short periods. Silicone rubbers are thus suitable as a material for rubber components used in high temperature environments.

Silicone rubber also has excellent resistance to cold temperatures. The embrittlement point of typical organic rubbers is between −20° and −30° C., compared to −60° to −70° C. for silicone rubbers. Even at temperatures at which organic rubbers turn brittle, silicone rubber remains elastic. Some products withstand extremely low temperatures of −100° C. and below.

Generally speaking, silicone rubber hardens when heated in air, with decreasing elongation as it deteriorates; but in sealed conditions it softens as it deteriorates, and its operating life at high temperatures is shorter in sealed conditions than in air. This softening results from the degradation of the siloxane polymer. Adjusting the silicone rubber formula, using a different curing agent, and/or post-curing can help prevent softening in hot, sealed conditions. Such products are also available.

Silicone rubbers have exceptional weatherability. Ozone created by corona discharge rapidly deteriorates most organic rubbers, but has almost no effect on silicone rubber. In addition, silicone rubber can be exposed to wind, rain and UV rays for long periods with virtually no change in its physical properties.

Results of Long-Term Outdoor Exposure Testing of Various Rubbers

| | Deterioration conditions | | | |
| --- | --- | --- | --- | --- |
| | Time until surface cracks are first apparent (years) | | Time of sunlight exposure until elongation is ½ that of the initial | |
| | Location | | | |
| Rubber type | Panama | Rock Island | Panama | Rock Island |
| Styrene butadiene | 2-3.5 | Over 10 years | 4 | 10 |
| Nitrile | 0.5-1 | — | 7 | 10 |
| Chloroprene | — | — | 8.5 | Over 10 years |
| Silicone (methyl vinyl) | Over 10 years | Over 10 years | Over 10 years | Over 10 years to decline to 75% |
| Silicone (methylphenyl) | — | — | Over 10 years | Over 10 years |
| Fluorosilicone | — | — | 0.5 | 4 |
| Ethylene propylene | — | — | 10 | Over 8.5 years to decline to 75% |
| Fluorine | 10 | 10 | Over 10 years to decline to 90% | |

Silicone rubber can be immersed in water (cold water, warm water, boiling water) for long periods with water absorption of about 1%, and with virtually no effect on mechanical strength or electrical properties. Typically, under ordinary pressure, contact with steam causes almost no deterioration of silicone rubbers. With pressurized steam, however, the effects increase as steam pressure increases. High pressure steam at temperatures over 150° C. causes breakdown of the siloxane polymer and a decline in the properties of the rubber. This effect can be ameliorated by adjusting the silicone rubber formula, selecting a proper curing agent, and/or post-curing. There are numerous products available with improved resistance to steam and hot water.

Silicone rubber has outstanding resistance to oil at high temperatures. Among common organic rubbers, nitrile rubber and chloroprene rubber have somewhat higher oil resistance at temperatures below 100° C., but at higher temperatures silicone rubber is superior.

Silicone rubber also has excellent resistance to solvents and other chemicals. It is essentially unaffected by polar organic compounds (aniline, alcohol, etc.) or dilute acids or bases, with the increase in volume due to swelling in the range of only 10%-15%. Silicone rubber does swell in non-polar organic compounds like benzene, toluene and gasoline; but unlike most organic rubbers, it does not decompose or dissolve, and will return to its former state when the solvent is removed. Silicone rubber is, however, adversely affected by strong acids and bases, so it should not be used where it will come in contact with such chemicals.

Typically, the effects of solvents on silicone are evidenced by the swelling, softening and reduced strength of the rubber; the extent of these effects depends on the type of solvent involved.

Oil and Chemical Resistance of Common Methyl Vinyl Silicone Rubber

| Type of oil/chemical | Immersion conditions ° C./h | Hardness points | Weight % | Volume % | Tensile strength % | Elongation % |
| --- | --- | --- | --- | --- | --- | --- |
| ASTM No. 1 | 150/168 | −10 |  | +10 | −10 | −10 |
| ASTM No. 3 | 150/168 | −25 |  | +40 | −20 | −20 |
| GM Hydramatic Fluid | 94/70 | −35 |  | +35 | −40 | −5 |
| Ford Brake Fluid | 150/72 | −20 |  | +15 | −60 | −40 |
| Diesel Fuel | 50/168 | −30 |  | +105 | — | — |
| Gasoline | 23/168 | −20 |  | +165 | — | — |
| Skydrol 500A Fluid | 70/168 | −5 |  | +10 | −10 | +5 |
| Motor oil (SAE #30) | 175/168 | −8 |  | −8 | −70 | −65 |
| Conc. Nitric acid | 25/168 |  | +10 | +10 | −80 | 30 |
| 7% Nitric acid | 25/168 |  | <1 | <1 | −50 | −30 |
| Conc. Sulfuric acid | 25/168 |  | Dissolves | Dissolves | Dissolves | Dissolves |
| 10% Sulfuric acid | 25/168 |  | <1 | <1 | 0 | 0 |
| Acetic acid | 25/168 |  | +3 | +4 | −20 | +10 |
| 5% Acetic acid | 25/168 |  | +2 | +2 | −20 | +10 |
| Conc. Hydrochloric acid | 25/168 |  | +3 | +4 | −40 | −20 |
| 10% Hydrochloric acid | 25/168 |  | +2 | +2 | −50 | −50 |
| 10% Sodium hydroxide solution | 25/168 |  | −2 | −1 | −10 | 0 |
| 2% Sodium hydroxide solution | 25/168 |  | <1 | <1 | 0 | 0 |
| Conc. Ammonia water | 25/168 |  | +2 | +1 | −30 | +10 |
| 10% Ammonia water | 25/168 |  | +2 | +2 | −20 | 0 |
| Water | 25/168 |  | <1 | <1 | 0 | 0 |
|  | 100/70 |  | <1 | <1 | −10 | −10 |
|  | 70/168 |  | +1 | <1 | −10 | +10 |
| 3% Hydrogen peroxide solution | 25/168 |  | <1 | <1 | 0 | +20 |

Change in Volume of Rubbers Caused by Various Fluids (after 168 Hour Immersion

| Fluid type | Temperature ° C. | Nitrite 28% | Nitrite 33% | Nitrite 38% | Chloroprene | Natural rubber | Styrene butadiene | Butyl | Silicone | Hypalon ® |
| --- | --- | --- | --- | --- | --- | --- | --- | --- | --- | --- |
| Gasoline | 50 | 15 | 10 | 6 | 55 | 250 | 140 | 240 | 260 | 85 |
| ASTM #1 oil | 50 | −1 | −1.5 | −2 | 5 | 60 | 12 | 20 | 4 | 4 |
| ASTM #3 oil | 50 | 10 | 3 | 0.5 | 65 | 200 | 130 | 120 | 40 | 65 |
| Diesel oil | 50 | 20 | 12 | 5 | 70 | 250 | 150 | 250 | 150 | 120 |
| Olive oil | 50 | −2 | −2 | −2 | 27 | 100 | 50 | 10 | 4 | 40 |
| Lard | 50 | 0.5 | 1 | 1.5 | 30 | 110 | 50 | 10 | 4 | 45 |
| Formaldehyde | 50 | 10 | 10 | 10 | 25 | 6 | 7 | 0.5 | 1 | 1.2 |
| Ethanol | 50 | 20 | 20 | 18 | 7 | 3 | −5 | 2 | 15 | 5 |
| Glycol | 50 | 0.5 | 0.5 | 0.5 | 2 | 0.5 | 0.5 | −0.2 | 1 | 0.5 |
| Ethyl ether | 50 | 50 | 30 | 20 | 95 | 170 | 135 | 90 | 270 | 85 |
| Methyl ethyl ketone | 50 | 250 | 250 | 250 | 150 | 85 | 80 | 15 | 150 | 150 |
| Trichloroethylene | 50 | 290 | 230 | 230 | 380 | 420 | 400 | 300 | 300 | 600 |
| Carbon tetrachloride | 50 | 110 | 75 | 55 | 330 | 420 | 400 | 275 | 300 | 350 |
| Benzene | 50 | 250 | 200 | 160 | 300 | 350 | 350 | 150 | 240 | 430 |
| Aniline | 50 | 360 | 380 | 420 | 125 | 15 | 30 | 10 | 7 | 70 |
| Phenol | 50 | 450 | 470 | 510 | 85 | 35 | 60 | 3 | 10 | 80 |

| Fluid type | Temperature °C. | Nitrite 28% | Nitrite 33% | Nitrite 38% | Chloroprene | Natural rubber | Styrene butadiene | Butyl | Silicone | Hypalon ® |
|---|---|---|---|---|---|---|---|---|---|---|
| Cyclohexanol | 50 | 50 | 40 | 25 | 40 | 55 | 35 | 7 | 25 | 20 |
| Distilled water | 100 | 10 | 11 | 12 | 12 | 10 | 2.5 | 5 | 2 | 4 |
| Sea water | 50 | 2 | 3 | 3 | 5 | 2 | 7 | 0.5 | 0.5 | 0.5 |

In one embodiment, the silicone rubber used has high insulation resistance of Iff2.m-100 Tam, and its insulating properties are stable over a wide range of temperatures and across a wide frequency spectrum. There is almost no decline in performance even when immersed in water, making silicone rubber an ideal insulating material. It has particularly good resistance to corona discharge and arcing at high voltages. Silicone rubber is thus used extensively as an insulator in high voltage applications.

In one embodiment, the thermal conductivity of the silicone rubber is about 0.2 W/mf2·K. In some embodiments, the silicone rubbers contain a high proportion of special inorganic fillers to improve thermal conductivity (about 1.3 W/mC2·K).

In one embodiment, flame retardancy and/or self-extinguishing properties is

Examples of suitable silicone rubbers are found in U.S. Pat. No. 3,813,364 GB1278798 and GB1381933, EP 0477681, U.S. Pat. No. 8,389,627, EP 1792944, EP 1217042, EP 0567253, WO 1987004449, EP 0369255 and EP 1094091, all fully incorporated herein by reference.

In one embodiment, a curable silicone rubber composition and an opacifier present in 0.1% to 35% by weight of the organopolysiloxane is contained in the silicone rubber composition, the silicone rubber being coated onto a translucent sheet material and cured.

The silicone rubber composition may be a room temperature vulcanizable silicone rubber composition or may be a heat-curable silicone rubber composition.

In one embodiment, the silicone rubber may be a room temperature vulcanizable silicone rubber composition comprising (a) a linear, organopolysiloxane containing terminal silicon-bonded hydroxy groups and having a viscosity of 500 to 10,000,000 centipoises when measured at 25° C., the organic groups of the aforesaid organopolysiloxane being substituted or unsubstituted monovalent hydrocarbon radicals, (b) from 0.1 to 15% by weight, based on organopolysiloxane, of (1) an organoxysilane or silicate corresponding to the general formula.

(RO)₃Si—R¹  (1)

where R is a monovalent hydrocarbon or halogenated hydrocarbon radical and R**** is an alkyl, haloalkyl, aryl, haloaryl, alkenyl, cycloalkyl, cycloalkenyl, cyanoalkyl, alkoxy or acyloxy radical, or (2) a liquid partial hydrolysis product of the aforementioned organoxy silane or silicate compounds, (c) from 0.1 to 5% by weight, based on the organopolysiloxane, of a catalyst which is metal salt of an organic monocarboxylic or dicarboxylic acid in which the metal ion is lead, tin, zirconium, antimony, iron, cadmium, barium, calcium, titanium, bismuth or manganese, and (d) from 0.1 to 10% by weight, based on the organopolysiloxane, of a nitrogen-containing silane of the formula:

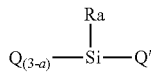

where R is a monovalent hydrocarbon or halogenated hydrocarbon radical, Q is an alkoxy, phenoxy, halo, a ino or dialkylamino group, and Q* is a saturated, unsaturated or aromatic hydrocarbon residue substituted by at least one amino hydrazone, azirane or, cyano group, and optionally one or more thio, sulphone, oxa, oxo, diorganosilicone and/or ester groups, and a is 0, 1 or 2.

These compositions are self-bonding, i.e. they do not require the use of a primer. The presence of the nitrogen-containing silane in an amount of 0.1 to 10% by weight, based on the linear organopolysiloxane (a) imparts the desired self-bonding properties to the room temperature vulcanizable silicone composition. The nitrogen-containing silane (d) acts both as a self-bonding agent and as a catalytic agent in the composition. The composition, however, also contains an additional catalyst (c) constituted by from 0.1 to 5% by weight, based on organopolysiloxane, of a catalyst which is a metallic salt of an organic monocarboxylic or dicarboxylic acid in which the metal ion is lead, tin, zirconium, antimony, iron, cadmium, barium, calcium, titanium, bismuth or manganese. Preferred nitrogen containing silanes (d) have the formula.

  (3)

where R**** is a monovalent hydrocarbon or halogenated hydrocarbon radical of up to 10 carbon atoms, most preferably an alkyl radical of 1 to 5 carbon atoms; a has the meaning given above and preferably has a value of 0. The present composition may additionally include a branched or straight polymer compound of (R^^SiO units, (R3)SiO-j/2 units and R3SiO3/2 units having a 0.05 to 8% by weight, preferably 0.1 to 8% by weight of hydroxy radicals (the viscosity of the polymer being preferably between 500 to 1.0×10^ centipoise at 25° C.). The ratio of the organosiloxy units to the diorganosiloxy units is from 0.11 to 1.4 and the ratio of the trioganosiloxy units to the diorganosiloxy units is from 0.02 to 1, inclusive. The preferred linear fluid organopolysiloxane containing terminal silicon-bonded hydroxy groups and having a viscosity of 500 to 10,000,000 centipoises when measured at 25° C., has preferably the formula.

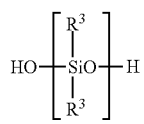
(4)

where $R^3$ is a monovalent hydrocarbon or halogenated hydrocarbon radical and r is a whole number from 250 to 7,275. The radicals R, R2, and R3 are preferably alkyl radicals, such as methyl, ethyl, propyl, butyl or hexyl; aryl radicals such as phenyl, or diphenyl; alkaryl radicals such as tolyl, xylyl, or ethylphenyl; aralkyl radicals such as benzyl, or phenylethyl; haloaryl and haloalkyl such as chlorophenyl, tetrachlorophenyl, or difluorophenyl; and alkenyl radicals such as vinyl or allyl. Further, R3 may also represent cyanoalkyl, cycloalkyl or cycloalkenyl radicals. The R3 groups attached to a single silicone radical may be the same groups or different groups. It has been found that at least 50% and preferably 70 to 100% of the R3 groups in the diorganopolysiloxane molecule should be methyl. Further, the diorganopolysiloxane can be a homopolymer, or a copolymer having different types of units in the chain such as dimethyl, diphenyl, or methyl-phenyl.

The organopolysiloxanes of formula (4) may also be represented by the average unit formula,

(5)

where $R^3$ is defined above and the value of m may vary from 1.99 to 2. The above average unit formula only represents organopolysiloxanes having monofunctional terminal groups and optional trifunctional units. However, in one embodiment, the terminal groups are hydroxy and the monofunctional and trifunctional groups be kept to a minimum.

In order for the diorganopolysiloxane fluids to cure there can be present in the composition the cross-linking agent of formula (1). In that formula, R groups may be alkyl radicals such as methyl, ethyl, propyl, isopropyl, butyl, amyl, isoamyl, octyl, isooctyl, decyl, or dodecyl; haloalkyl such as the chlorinated, brominated, or fluorinated alkyl radicals. In addition, R may represent aryl, aralkyl and alkenyl radicals such as vinyl, allyl, phenyl, tolyl, xylyl, benzyl, phenylethyl, naphthyl, anthracyl, or biphenyl, as well as the halogen-substituted derivatives of the above radicals. In addition, R may represent cycloalkenyl, cycloalkyl and cyanoalkyl radicals. The radical R1 represents the same radicals as R and, in addition, preferably represents alkoxy or aryloxy radicals such as methoxy, ethoxy, butoxy and phenoxy. Alternatively to the monomeric compounds of formula (1), liquid partially hydrolyzed products thereof can also be used as cross-linking agents. Such hydrolysis products are obtained by effecting partial hydrolysis in water of the particular monomeric compound in the presence of small amounts of acid to a point where it is still water-insoluble and still possible to isolate a liquid partially hydrolyzed organosilicone compound. Thus, the ethyl silicate having the formula $(C_2H_5O)_4Si$ may be partially hydrolyzed by adding acids or acid-forming metal salts, such as FeCl, CUCl2, AlCl3, or SnCl^ to the liquid monomeric organosilicate, and thereafter effecting suitable hydrolysis of this mixture of ingredients in water to obtain the two-phase composition, from which the water-insoluble, partially hydrolyzed organosilicate can readily be separated from the aqueous phase and catalyst. A partially hydrolyzed ethyl silicate is sold under the tradename Ethyl Silicate-40, by Union Carbide Corporation.

There is added from 0.1 to 15.0% by weight of the cross-linking agent of formula (1) (or its hydrolysis product) and preferably 0.1 to 10% by weight, based on the weight of the diorganopolysiloxane of formula (4) and (5). If more than 15.0% by weight of cross-linking agent were to be used, the excess would not function as a cross-linking agent since the initial hydroxy positions on the organopolysiloxane would already have reacted with the cross-linking agent and the excess would act as a filler, reducing the elasticity of the cured silicone rubber composition. If less than 0.1% by weight of cross-linking agent were to be used, there would not be sufficient cross-linking agent to react with the organopolysiloxane to form the cured silicone rubber.

Although the above mentioned cross-linking agents must be used, there may additionally be used as cross-linking agents, organopolysiloxane resins having a functionality greater than 2 and preferably greater than 2.5. The organopolysiloxane resins are methylsiloxanes, or resins which contain both onomethyl and dimethyl or monophenyl units. There may also be used ethylsiloxane resins, in which the ratio R"Si is 1.4 to 1 and which contains 15 mol % of butoxy groups, or there may be used resins in which the ratio R"Si is 1.1 to 1 and which contain 10 mol % of methoxy groups or there may be used methylphenylsiloxane resins containing 50 mol % of monomethyl units, 25 mol % of dimethyl units and 25 mol % of monophenyl units.

Other suitable additional cross-linking agents are organohydrogenpolysiloxanes of the formula,

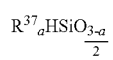
(6)

in which $R^{3'}$ is an alkyl or aryl radical and a is a number less than 2, but is not zero. The organohydrogenpolysiloxane cross-linking agents have the disadvantage that during curing there is evolved hydrogen gas which can result in bubbles being trapped in the silicone rubber composition. Although the above cross-linking agents can be used in the compositions, the organosilicates of formula (1) for their partial hydrolysis products must be present since the processability of the composition is facilitated and the cured silicone rubber composition has better physical properties. A more detailed description of these other cross-linking agents is to be found in U.S. Pat. No. 3,127,363.

The other essential component in this silicone rubber composition is a catalyst. It has been found that only certain metallic salts of organic carboxylic acids and dicarboxylic acids, in addition to the nitrogen-containing silanes of formula (2), may be employed with the organopolysiloxanes of formula (4) and (5) as a curing catalyst. Suitable acid radicals are the resinate, linoleate, stearate, and oleate, as well as the lower radicals such as acetate, butyrate, and octoate. Metallic salts of lauric acid have been found to be especially effective. The metal ion of the metal salt is lead, tin, zirconium, antimony, iron, cadmium, barium, calcium, titanium, bismuth or manganese. Thus, examples of suitable metallic salt catalysts are tin naphthenate, lead octoate, tin octoate, iron stearate, tin oleate, antimony octoate, tinbutyrate, basic dibutyl tin laurate and dibutyl tin dilurate. The tin and lead salts are preferred since they are usually soluble in the diorganopolysiloxanes of formulae (4) and (5) and since they have enhanced catalytic activity in combination with the alkyl silicate. It is important to note that other compounds which would be expected to exercise good catalytic activity in the mixture of diorganopolysiloxane, filler and alkyl silicate. It is important to note that other compounds which would be expected" to exercise good catalytic activity in the mixture of diorganopolysiloxane, filler and alkyl silicate exercise no catalytic activity whatsoever. This class of compounds are zinc salts of organic acids, cobalt oleate, cobalt naphthenate, manganese naphthenate, nickel naphthenate and calcium stearate. From 0.1 to 5% by weight of the metallic salt is used, based on the weight of the diorganopolysiloxane.

Various heat curable silicone rubber compositions may also be used. These compositions may comprise, by weight (1) 100 parts of a liquid vinyl chain-stopped polysiloxane having the formula

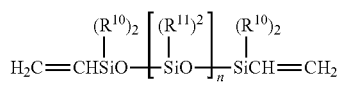

where R10 and R12 are each an alkyl radical containing from 1 to 8 carbon atoms, a mononuclear aryl radical, a cycloalkyl radical having from 5 to 7 ring carbon atoms or a mononuclear aralkyl radical of which the alkyl radical(s) contain(s) from 1 to 8 carbon atoms with at least 50 mole percent of the R' radicals being methyl and where n has a value sufficient to provide a viscosity of 1,000 to 750,000 centistokes at 25° C., preferably from 50,000 to 150,000 inclusive,
(2) from 0 to 50, preferably from 20 to 50 parts of an organopolysiloxane copolymer comprising (R")3SiO0>5 units, (R")2SiO units and SiO$_2$ units, where each R" is a vinyl radical, an alkyl radical containing from 1 to 8 carbon atoms, a mononuclear aryl radical, a cycloalkyl radical having from 5 to 7 ring carbon atoms or a mononuclear aralkyl radical of which the alkyl radical (s) contain(s) from 1 to 8 carbon atoms, where the ratio of (R-'^SIOQ^ units to Si02 units is from 0.5:1 to 1:1, and where from 2.5 to 10 mole percent of the silicone atoms contain silicon-bonded vinyl groups,
(3) a catalyst comprising platinum and/or a platinum compound in an amount sufficient to provide from 10-3 to 10"° gram atoms of platinum per mole of silicon-bonded vinyl radicals in the composition,
(4) an amount of a liquid organohydrogenpolysiloxane having the formula:

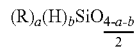

2 sufficient to provide from 0.5 to 1.2 and preferably 1.0 silicon-bonded hydrogen atom per silicon-bonded vinyl group in the composition described in (1), where R is as previously defined, a has a value of from 1.00 to 2.00, b has a value of from 0.1 to 1.2, preferably 0.1 to 1.0, and the sum of a plus b is from 2.00 to 2.67, there being at least two silicon-bonded hydrogen atoms per molecule, (5) from 0.1 to 1 part of a liquid vinyl siloxane hydrolyzate of the formula:

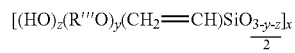

preferably prepared by the hydrolysis of a mixture of vinyl trichlorosilane and a vinyl trialkoxysilane, such as vinyl triethoxysilane, where R"$^1$ is an alkyl radical having one to 8 carbon atoms, x is a number greater than 3, y has a value of from 0.01 to 0.4, and preferably has a value of from 0.05 to 0.1 and z has a value of 0.1 to 0.4, preferably from 0.2 to 0.4, (6) from 0 percent to 85 percent, based upon the total weight of the above described mixture, of a halocarbon catalyst inhibitor which is a halocarbon having 2 carbon atoms and at least 3 halogen substituents, said halogen substituents having an atomic weight of less than 126 and being positioned anywhere on the molecule. When a completely transparent laminate is desired, the fluid vinyl siloxane hydrolyzate of (5) is not mixed into the compositions but can be used to prime the transparent surfaces to be joined. The hydrolyzate is usually applied to the surfaces in an ethyl alcohol solution containing from 3 to 6 percent by weight of the hydrolyzate.

The compositions can be prepared in one embodiment by mixing in a suitable fashion all of the components described above plus any additional components such as will be described subsequently and maintaining the mixture at a temperature at which it is to be cured. The compositions cure at temperatures which can vary from about 50° C. or lower to temperatures of the order of 110° C. or higher depending upon the particular amount of platinum compound catalyst present in composition and depending upon the time which is allowed for cure. Likewise, the compositions can be prevented from curing by maintaining them at a reduced temperature such as a temperature of 0° C., in which case all of the components can be kept together for extended periods of time without curing. The compositions can also be prevented from curing by the utilization of the above described halocarbon catalyst inhibitor. The compositions can vary from readily flowable liquids to slowly flowing liquids depending upon the viscosity of the various components employed in the reaction mixture and depending upon the amount of filler included in the reaction mixture. Regardless of the flow characteristics of the compositions and the proportions of the various ingredients, the compositions cure to a hard, tough silicone elastomer upon maintaining the compositions at the curing temperature for the required amount of time. The compositions are translucent or opaque and the color of the cured product is a function of any added filler and the opacifying agents added to the compositions. When a halocarbon inhibitor, as above described, is used in the compositions of the present invention, the viscosity of the vinyl containing fluid can be increased up to 3,000,000 centistokes and still have a readily workable material.

All of the components of the composition are well known in the art. The vinyl chain-stopped organopolysiloxane component (1) is typified by various compositions within the scope of formula (1) where the monovalent hydrocarbon radicals represented by R and R' include alkyl radicals containing from one to 8 carbon atoms, e.g., methyl, ethyl, propyl, butyl and octyl radicals; mononuclear aryl radicals, e.g., phenyl, tolyl and xylyl radicals; cycloalkyl radicals containing 5 to 7 ring carbon atoms, e.g., cyclohexyl and cycloheptyl radicals, mononuclear aryl ^-Cg alkyl radicals, e.g., benzyl and phenylethyl radicals.

Further examples of heat curable compositions include a self-bonding heat-vulcanizable silicone rubber composition comprising an organopolysiloxane polymer having a viscosity of at least 100,000 centipoise at 25° C. of the formula.

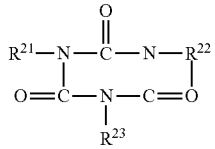
(7)

a curing catalyst and an additive selected from the class consisting of an alkenylisocyanurate of the formula.

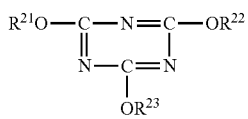
(8)

and a cyanurate of the formula.

$$R^{21}O-C-N=C-OR^{22} \atop \| \atop N-C=N \atop | \atop OR^{23}$$
(9)

and mixtures thereof, where R ̂ is selected from monovalent hydrocarbon radicals and halogenated monovalent hydrocarbon radicals, R21 is selected from unsaturated monovalent hydrocarbon radicals and unsaturated halogenated monovalent hydrocarbon radicals, R22 and R23 are selected from R1. radicals, saturated monovalent hydrocarbon radicals and saturated halogenated monovalent hydrocarbon radicals and a varies from 1.95 to 2.01, inclusive. In the above composition, there is preferably 82% to 99.65% by weight of the organopolysiloxane, 0.1% to 8% by weight of the curing catalyst and 0.25% to 10.0% by weight of the isocyanurate, based on the weight of the composition. There may further preferably be included in the composition a filler such as silica filler, which comprises 20% to 60% by weight of the organopolysiloxane and there may also be present a process aid which comprises 1% to 25% by weight of the organopolysiloxane. The curing catalyst is preferably t-butyl perbenzoate or dicuyl peroxide. The self-bonding, curable silicone rubber components are mixed and heated to a temperature in the range of 80° C. to 650° C., so as to cure the resulting mixture to a silicone rubber mass. In the above composition, a critical ingredient is the isocyanurate and cyanurate. The non-silicone isocyanurate or cyanurate is preferred since it has very good shelf-aging properties. If shelf-aging is not an important factor, then there may be used in place of the isocyanurate of Formula (8) or the cyanurate of Formula (9) above, an additive selected from the class consisting of a silylisocyanurate of the formula.

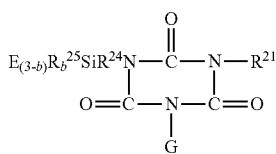
(10)

and a silylcyanurate of the formula,

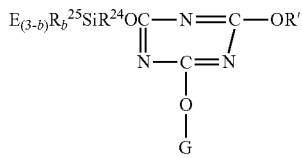
(11)

in the above formulas, R$^{21}$ is defined previously, G is selected from R$^{21}$— radicals and radicals of the formula, $$E_{(3-b)}R_b{}^{25}SiR^{24}—$$

where E is selected from R2o0- radicals and R oCOO— radicals, where R25 and R26 are selected from monovalent hydrocarbon radicals and halogenated monovalent hydrocarbon radicals, R24 is selected from divalent hydrocarbon radicals and halogenated divalent hydrocarbon radicals and b is a whole number equal to 0 to 3, inclusive. The silylisocyanurate and silylcyanurate of Formulas (10) and (11) may have one silyl or two silyl substituent groups thereon on the isocyanurate moiety or cyanurate moiety, but preferably has only one silyl group thereon. Further, in the silylisocyanurates and silylcyanurates, preferably, G is represented by an R' radical, that is, an unsaturated monovalent hydrocarbon radical. The curing of the silicone rubber composition can be effected by chemical vulcanizing agents or by high energy electron radiation. More often, chemical vulcanizing agents are employed for the curing operation and any of the conventional curing agents can be employed. The preferred curing agents are organic peroxides conventionally used to cure silicone elastomers.

Especially suitable are the peroxides which may have the structural formulae,

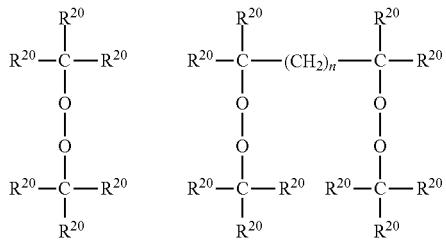

wherein R2̂ represents the same alkyl group throughout or alkyl groups of two or more different types and n is zero or a positive integer. Among the specific peroxidic curing catalysts that are preferred are di-tertiary-butyl peroxide, tertiary-butyltriethylmethyl peroxide, tertiary-butyl triphenyl methyl peroxide, t-butyl perbenzoate and a ditertiary alkyl peroxide such as dicumyl peroxide. Other suitable peroxidic catalysts which effect curing through saturated as well as unsaturated hydrocarbon groups on the silicone chain are aryl peroxides which include benzoyl peroxides, mixed alkyl-aryl peroxidic compounds which include tertiary-butyl perbenzoate, chloroaryl peroxides such as 1,4-dichlorobenzoyl peroxide; 2,4-dichlorobenzoyl peroxide and monochlorobenzoyl peroxide. From 0.1-8 percent of said peroxidic compound by weight of the composition is used to cure the silicone rubber composition and preferably 0.5-3.0 percent by weight of the above curing catalyst, t-butyl perbenzoate, is preferred.

Other examples of heat curable compositions include a self-bonding, heat curable silicone rubber composition which comprises: (a) from 82 to 99.65% by weight of a linear organopolysiloxane polymer having a viscosity of at. least 100,000 centipoise at 25° C., and having the average unit formula:

$$(R^{30})_a SiO_{\frac{4-a}{2}} \qquad (12)$$

(b) from 0.1 to 8% by weight of a curing catalyst, and
(c) from 0.25 to 10% by weight of a self-bonding additive of the formula:

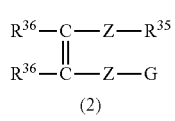 or 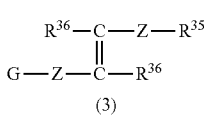 (13)
(2) (3)

in which the formulae a has a value of from 1.95 to 2.01 inclusive, $R^{30}$ is a monovalent hydrocarbon or halohydrocarbon radical. $R^{36}$ is alkyl or hydrogen, Z is phenylene or a group of the formula —CO-0-, —CO—, —CO—NH— or —CO—NR$^{32}$— in which $R^{32}$ is a monovalent hydrocarbon o halohydrocarbon radical, G is hydrogen, a saturated monovalent hydrocarbon or halohydrocarbon radical, or has the same meaning as $R^{35}$, $R^{35}$ is an unsaturated monovalent hydrocarbon or halohydrocarbon radical, or a group of the formula:

$$—R^{34}—SiR_n^{32}(M)_{3-n} \qquad (14)$$

in which
$R^{34}$ is a divalent hydrocarbon or halohydrocarbon radical, $R^{32}$ has the meaning given above, M is a group of the formula $R^{33}$0- or $R^{33}$—CO-0- in which $R^{33}$ is a monovalent hydrocarbon or halohydrocarbon radical, and n is 0 or a whole number from 1 to 3.

The above composition preferably comprises 1% to 25% by weight, based on the organopolysiloxane of a process aid. There may also be present from 10 to 100% by weight, preferably 20 to 60% by weight, based on the organopolysiloxane, of a filler, preferably silica. In addition, there of course can be any of the other ingredients and additives normally to be found in heat-curable silicone rubber compositions. In the above formulae, that is, formulae (12) to (14), the radicals R3, R32 and R33 may be aryl radicals and halogenated aryl radicals such as phenyl, chlorophenyl, xylyl or tolyl, aralkyl radicals, such as phenethyl, or benzyl; aliphatic, haloaliphatic and cycloaliphatic radicals such as alkyl, alkenyl, cycloalkyl, haloalkyl, including methyl, ethyl, propyl, chlorobutyl, or cyclohexyl. Preferably, the R3" radical is represented by methyl and phenyl radicals, where at least 50% of the R30 radicals are methyl. Further, in the organopolysiloxane polymer represented by formula (12), there is preferably 0.1 to 0.6 weight percent of the polymer of vinyl radicals. Further, preferably the R32 and R33 radicals are alkyl radicals of not more than 8 carbon atoms and are preferably methyl or ethyl. The R3° radical is selected from hydrogen and alkyl radicals of preferably up to 10 carbon atoms. Preferably, the R3° radical is hydrogen. Radicals represented by R35 are alkenyl radicals, cycloalkenyl radicals and arylalkenyl radicals, such as vinyl, allyl, cyclohexyl, and phenyl-2-propenyl. In addition, the R35 radicals may be represented by alkynyl radicals, such as propargyl. It is preferred that R5 be either vinyl or allyl or an alkenyl radical of less than 8 carbon atoms. The R32 radical (when R*'" is a group of the formula R34-SiRn 32(M)3_n) may be saturated monovalent hydrocarbon radical or an unsaturated monovalent hydrocarbon radical and is preferably represented by the radicals recited in the exemplification of the R3, R32 and -3"i"3 R—****' radicals.

However, more preferably, the R$^J$ radical is selected from unsaturated monovalent hydrocarbon radicals and halogenated unsaturated monovalent hydrocarbon radicals such as alkenyl radicals of up to 8 carbon atoms. It is preferred that G be an unsaturated monovalent hydrocarbon radical. When R3**** represents a group of the formula —R34-SiRa 32(M)3_n, it is preferable that G be an unsaturated monovalent hydrocarbon radical e.g. an alkenyl radical of up to 8 carbon atoms or arylene radical. It is preferable that Z be a carboxyl radical, since when Z has the other meanings enumerated above, these compounds are more difficult to synthesize. In formulae (13), both the cis and trans isomers have been shown and are intended to be covered. Any of the isomers of the maleates, and fumarates and the silylmaleates and silylfumarates disclosed or mixtures of the isomers may be used. In addition, single compounds may be used or a mixture of any of the self-bonding additives. Radicals included by R34 are divalent saturated and unsaturated hydrocarbon radicals such as alkenyl, alkenylene, alkynylene and arylene radicals, which are exemplified by ethylene, trimethylene, tetramethylene, phenylene, and ethylene-phenylene. The radical R34 may have 2 to 20 carbon atoms, and is preferably ethylene.

Maleates coming within the scope of formula (13) are diallylmaleate, dipropenylmaleate, and dibutenyl aleate. The preferred silylmaleates coming within the scope of these formulae are bis-trimethoxysilylpropylmaleate and bis-trimethoxysilylbutylmaleate. The preferred compounds within the scope of formulae (13) are as follows: bis-trimethoxysilylpropylmaleate diallyl fumarate allyl hydrogen maleate bis-(3-chloropropenyl) maleate ethyl allyl fumarate diisopropenyl fumarate bis-trimethoxysilylpropyl fumarate bis-dimethoxymethylsilylpropyl maleate trimethoxysilylpropyl allyl fumarate bis-ethoxydimethylsilylpropenyl maleate. There are also within the scope of formula (12) polydiorganosiloxanes which can be copolymers containing two or more different diorganosiloxane units therein and copolymers of dimethylsiloxane units and methylphenylsiloxane units; or copolymers of methylphenylsiloxane units, diphenylsiloxane units, dimethylsiloxane units and methylvinylsiloxane units as well as copolymers of dimethylsiloxane units, methylvinylsiloxane units and diphenylsiloxane units.

The curing of the silicone rubber composition invention can be effected by any of the conventional curing agents. The preferred curing agents are organic peroxidic compounds conventionally used to cure silicone elastomers as described above. There may be incorporated into the organopolysiloxane a filler which may be of the reinforcing filler type or of the semi-reinforcing type. Generally, the reinforcing fillers having 100-300 square meter surface areas per gram while the semi-reinforcing fillers having a surface area of 1-20 square meters per gram.

The reinforcing fillers may be added when it is desired to have a high strength silicone rubber composition, that is, a composition with high values for tensile strength and percent elongation. Illustrative of the many fillers which can be employed are lithopone, zinc oxide, zirconium silicate, silica aerogel, iron oxide, diatomaceous earth, fumed silica, precipitated silica, glass fibers, magnesium oxide, chromium oxide, zirconium oxide, aluminum oxide, crushed quartz, calcined clay, asbestos, cork, cotton and synthetic fibers. There can also be used silica filler treated with an organosiloxane cyclic trimer or tetramer such that the filler is hydrophobic. Generally, there may be added to the organopolysiloxane, 5 to 300% by weight of filler and preferably 10-200% by weight.

An essential feature of the composition is the opacifier. Any opacifying agents can be used although the preferred opacifying agents are one or more of titanium dioxide, carbon black and calcium carbonate. The opacifier is present in an amount of 0.1% to 35% by weight of the organopolysiloxane, preferably the amount of opacifier will vary according to the shade of glass required. For example, if a black opaque glass is required, it is preferred that from 0.1 to 3% by weight based on the weight of the polysiloxane of carbon black is used. If a grey opacifier is required a mixture of carbon black and titanium dioxide may be used in a ratio of between 1:10 and 1:100 by weight of carbon black: titanium dioxide and preferably in an amount of 1 to 25% by weight. Titanium dioxide can be used in an amount of 1 to 25% by weight all based on the weight of the organopolysiloxane.

The present invention provides a method of coating surface of a translucent material to stop light transmission by the translucent material which method comprises applying a composition comprising an organopolysiloxane and an opacifier and curing the composition.

Any of the organopolysiloxanes described may be used for the opacifying coating of the present invention.

The method of the present invention relates to the coating of translucent materials. Many types of translucent material can be coated such as polymethylmethacrylate, polystyrene, polycarbonate, and glass, particularly solar reflecting glass. Glass is a particular material which causes difficulty because of problems of bonding any form of coatings with the glass. As glass is an inorganic material, the opacifying coating is thought to bond physically with the material, i.e. adhere to its surface. This type of adherence is subjected to the ravages of UV light when the glass is to be the exposed material and the opacifying coating is then on the inside of the glass. The opacifying coating has good bonding properties to glass. In one embodiment, a translucent material is provided, in particular glass, when coated by a method as described above. In one embodiment, a cladding material is provided comprising a translucent material as the portion exposed to the elements and the opacifying coating as the inner portion of the cladding.

In one embodiment, the translucent material, particularly glass, is cleaned in a washing machine using demineralised water. Because of the problems relating to bonding of the opacifying coating, i.e. the bond being exposed to UV light and large temperature variations, the glass should be thoroughly cleaned without the use of alkali. Following cleaning, the glass is preferably wiped with a solvent such as methyl ethyl ketone or isopropanol. If a plastics translucent material is to be cleaned prior to application of the opacifying coating then care must be taken in the selection of cleaning solvents to prevent damage to the translucent material. The application of the opacifying coating can be performed in a number of different ways. The essential feature is that the composition is thoroughly mixed so that the curing agent, the opacifying agent and the catalyst are uniformly dispersed with the other components of the silicone composition. Preferably the curing agent and the catalyst are separate from the remaining components of the silicone composition. In a two part form, the components are mixed in a spray gun and are sprayed onto the glass, the glass being generally in sheet or panel form. The opacifying coating can be applied to a number of different types of glass including clear colorless glass, solar reflecting glass, mirror glass and glass for fire walls. The opacifying coating can provide a consistent, even, homogenous coating on glass and can therefore provide suitable coatings for external mirror glass.

Polyorganosiloxanes made of units of the general formula

$$R_r SiO_{\frac{4-r}{2}} \quad (I)$$

where R is identical or different and is an unsubstituted or substituted hydrocarbon radical and r is 0, 1, 2 or 3 and has an average numerical value of from 1.9 to 2.1.

Examples of hydrocarbon radicals R are alkyl radicals such as the methyl, ethyl, n-propyl, isopropyl, n-butyl, isobutyl, tert-butyl, n-pentyl, isopentyl, neopentyl and tert-pentyl radicals; hexyl radicals such as the n-hexyl radical, heptyl radicals such as the n-heptyl radical; octyl radicals such as the n-octyl radical, and isooctyl radicals, such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as cyclopentyl, cyclohexyl and cycloheptyl radicals and methylcyclohexyl radicals; aryl radicals such as the phenyl, biphenyl, naphthyl, anthryl and phenanthryl radicals; and alkaryl radicals such as o-, m-, and p-tolyl radicals, xylyl radicals and ethylphenyl radicals; aralkyl radicals, such as the benzyl radical and the α- and β-phenylethyl radicals.

Examples of substituted hydrocarbon radicals R are halogenated alkyl radicals such as the 3-chloropropyl radical, the 3,3,3-trifluoropropyl radical, and the perfluorohexylethyl radical, and halogenated aryl radicals such as the p-chlorophenyl radical and the p-chlorobenzyl radical.

The radicals R are preferably hydrocarbon radicals having from 1 to 8 carbon atoms, most preferably the methyl radical. Other examples of radicals R are the vinyl, allyl, methallyl, 1-propenyl, 1-butenyl and 1-pentenyl radicals, the 5-hexenyl, butadienyl, hexadienyl, cyclopentenyl, cyclopentadienyl, cyclohexenyl, ethynyl, propargyl and 1-propynyl radicals. The radicals R are preferably alkenyl radicals having from 2 to 8 carbon atoms, most preferably the vinyl radical. Among unsubstituted or substituted hydrocarbon radicals having from 1 to 8 carbon atoms, particular preference is given to the methyl, vinyl, phenyl and 3,3,3-trifluoropropyl radicals.

There are preferably alkyl radicals, most preferably methyl radicals, bonded to at least 70 mol % of the Si atoms present in the polyorganosiloxane (A) made of units of the formula (I). If the polyorganosiloxanes contain, besides Si-bonded methyl and/or 3,3,3-trifluoropropyl radicals, Si-bonded vinyl and/or phenyl radicals, the amounts of the latter are preferably from 0.001 to 30 mol %.

The polyorganosiloxanes (A) are preferably composed predominantly of diorganosiloxane units. The end groups of the polyorganosiloxanes may be trialkylsiloxy groups, in particular the trimethylsiloxy radical or the dimethylvinylsiloxy radical. However, it is also possible for one or more of these alkyl groups to have been replaced by hydroxyl groups or by alkoxy groups, such as methoxy or ethoxy radicals. The polyorganosiloxanes (A) may be liquids or highly viscous substances. The viscosity of the polyorganosiloxanes (A) is preferably from 103 to 108 MPa·s at 25° C. It is possible to use either just one type of polyorganosiloxane (A) or a mixture of at least two different types of polyorganosiloxanes (A).

The crosslinking agents preferably used in the novel silicone rubber materials are peroxides, such as dibenzoyl peroxide, bis(2,4-dichlorobenzoyl) peroxide, dicumyl peroxide or 2,5-bis(tert-butylperoxy)-2,5-dimethylhexane, or mixtures of these, preferably a mixture of bis(2,4-dichlorobenzoyl) peroxide and 2,5-bis(tert-butylperoxy)-2,5-dimetylhexane. Another preferred crosslinking agent is a mixture of bis-4-methylbenzoyl peroxide (PMBP) and 2,5-dimethyl-2,5-di-tert-butylperoxyhexane (DHBP) in a ratio of from 1:0.4 to 0.5:1, preferably in a ratio of 1:0.4.

The polyorganosiloxanes (A) according to the invention also preferably comprise reinforcing and/or nonreinforcing fillers. Examples of reinforcing fillers are pyrogenic or precipitated silicas with BET surface areas of at least 50 m2/g.

The silica fillers mentioned may have hydrophilic character or may have been hydrophobicized by known processes. Reference may be made here, for example, to DE 38 39 900 A (Wacker-Chemie GmbH; application date Nov. 25, 1988) or to the corresponding U.S. Pat. No. 5,057,151. The hydrophobicization generally takes place using from 1 to 20% by weight of hexamethyldisilazane and/or divinyltetramethyldisilazane and from 0.5 to 5% by weight of water, based in each case on the total weight of the polyorganosiloxane material. These reagents are preferably added to an initial charge of the polyorganosiloxane (A) in a suitable mixing apparatus, e.g. a kneader or internal mixer, prior to incorporating the hydrophilic silica gradually into the material.

Examples of nonreinforcing fillers are powdered quartz, diatomaceous earth, calcium silicate, zirconium silicate, zeolite, metal oxide powders, such as aluminum oxide, titanium oxide, iron oxide, or zinc oxide, barium silicate, barium sulfate, calcium carbonate, calcium sulfate and polytetrafluoroethylene powder. Other fillers which may be used are fibrous components, such as glass fibers and synthetic polymer fibers. The BET surface area of these fillers is preferably less than 50 m2/g.

The novel polyorganosiloxane materials which can be crosslinked to give elastomers preferably comprise from 1 to 200 parts by weight, more preferably from 30 to 100 parts by weight of filler (B), based in each case on 100 parts by weight of polyorganosiloxane (A).

Depending on the particular application, additives (C), for example processing aids such as plasticizers, pigments, or stabilizers such as thermal stabilizers, may be added to the novel polyorganosiloxane materials which can be vulcanized to give elastomers.

Examples of plasticizers which can be used as additives (C) are polydimethylsiloxanes with a viscosity of not more than 1000 mm2/s at 25° C. and having trimethylsilyl and/or hydroxyl terminal groups, or biphenylsilanediol.

Examples of thermal stabilizers which can be used as additives (C) are transition metal salts of fatty acids, such as iron octoate, cerium octoate and titanium bythylate, transition metal silanolates, such as iron silanolate, and also cerium(IV) compounds, and oxides, e.g. iron oxide and titanium oxide and mixtures of these.

In the case of each of the components used to prepare the novel materials, a single type of a given component may be used, or else a mixture of at least two different types of that component. The novel pelletizing aids preferably comprise no other substances other than those previously described.

The amount of the novel additive added to this peroxidically crosslinked silicone rubber is preferably from 0.1 to 4% by weight, more preferably from 0.4 to 2% by weight, and most preferably from 0.8 to 1.2% by weight. Pelletization follows, using conventional means of pelletizing, e.g. a pelletizing die and rotating knife, giving a fully free-flowing pelletized material.

An addition-crosslinking polyorganosiloxane material is preferred for the silicone rubber. All of the abovementioned substances except the peroxidic crosslinking agent may also be used with the addition-crosslinking polyorganosiloxane materials. In the case of the polyorganosiloxane rubber materials which cure via hydrosilylation at an elevated temperature to give elastomers, polyorganosiloxanes (D) having Si-bonded hydrogen atoms and hydrosilylation catalysts (E) are also present.

The polyorganosiloxane crosslinking agents (D) may be linear, cyclic or branched, and preferably contain at least 3 Si-bonded hydrogen atoms. The polyorganosiloxanes (D) used are preferably polyorganosiloxanes of the general formula (II)

$$H_g R^2_{3-g} SiO(SiR^2_2 O)_k (SiR^2 HO)_l SiR^2_{3-g} H_g \qquad (II)$$

where R2 is as defined for R, g is 0 or 1, and each of k and l is 0 or an integer from 1 to 100.

Examples and preferred examples for the radicals R2 have been listed above in the examples for the radicals R. The radicals R2 are preferably saturated alkyl radicals or phenyl radicals.

Each of k and l is preferably 0 or an integer from 1 to 50. The sum of k and l is preferably from 1 to 50, in particular from 1 to 20.

Particular examples of polyorganosiloxanes (D) are copolymers made of dimethylhydrogensiloxane units, methylhydrogensiloxane units, dimethylsiloxane units and trimethylsiloxane units, copolymers made of trimethylsiloxane units, dimethylhydrogensiloxane units and methylhydrogensiloxane units, copolymers made of trimethylsiloxane units, dimethylsiloxane units and methylhydrogensiloxane units, copolymers made of methylhydrogensiloxane units and trimethylsiloxane units, copolymers made of methylhydrogensiloxane units, diphenylsiloxane units and trimethylsiloxane units, copolymers made of methylhydrogensiloxane units, dimethylhydrogensiloxane units and diphenylsiloxane units, copolymers made of methylhydrogensiloxane units, phenylmethylsiloxane units, trimethylsiloxane units and/or dimethylhydrogensiloxane units, copolymers made of methylhydrogensiloxane units, dimethylsiloxane units, diphenylsiloxane units, trimethylsiloxane units and/or dimethylhydrogensiloxane units, and also copolymers made of dimethylhydrogensiloxane units, trimethylsiloxane units, phenylhydrosiloxane units, dimethylsiloxane units and/or phenylmethylsiloxane units.

The amount of polyorganosiloxane (D) used is preferably sufficient to supply from 0.5 to 6 gram atoms, more preferably from 1 to 3 gram atoms, and most preferably from 1.5 to 2.5 gram atoms of Si-bonded hydrogen atom per mole of ethylenically unsaturated bonds in the radicals R1 of the polyorganosiloxane (A).

The hydrosilylation catalyst (E) used may in principle be any catalyst conventionally used in addition-crosslinking silicone rubber materials. These include the elements and compounds of platinum, rhodium, palladium, ruthenium and iridium, preferably platinum. The transition metals may, if desired, have been fixed on finely divided support materials such as active carbon, metal oxides such as aluminum oxide, or on pyrogenically prepared silicone dioxide.

Preference is given to the use of platinum and platinum compounds. Particular preference is given to platinum compounds soluble in polyorganosiloxanes. Examples of soluble platinum compounds which may be used are the platinum-olefin complexes of the formulae (PtCl2.olefin)2 and H(PtCl3.olefin), preferably using alkenes having from 2 to 8 carbon atoms, such as ethylene, propylene or isomers of butene or of octene, or cycloalkenes having from 5 to 7 carbon atoms, such as cyclopentene, cyclohexene or cycloheptene. Other soluble platinum catalysts are the platinum-cyclopropane complex of the formula (PtCl2.C3H6)2, the reaction product of hexachloroplatinic acid with alcohols, with ethers or with aldehydes or with mixtures of these, or the reaction products of hexachloroplatinic acid with methylvinylcyclotetrasiloxane in the presence of sodium bicarbonate in ethanolic solution. Preference is given to finely divided platinum on support materials such as silicone dioxide, aluminum oxide, or activated wood charcoal or animal charcoal; to platinum halides such as PtCl4, hexachloroplatinic acid and Na2PtCl4.nH2O; platinum-olefin complexes, e.g. those with ethylene, propylene or butadiene; platinum-alcohol complexes; platinum-styrene complexes as described in U.S. Pat. No. 4,394,317; platinum-alcoholate complexes; platinum-acetylacetonates; reaction products prepared from chloroplatinic acid and monoketones, e.g. cyclohexanone, methyl ethyl ketone, acetone, methyl n-propyl ketone, diisobutyl ketone, acetophenone or mesityl oxide; and platinum-vinylsiloxane complexes as described, for example, in U.S. Pat. Nos. 3,715,334, 3,775,452 and 3,814,730, such as platinum-divinyltetramethyldisiloxane complexes with or without detectable amounts of inorganic halogen; all in amounts sufficient to promote the curing of the composition at a temperature of up to about 250° C., where the organohydrogensiloxane and the hydrosilylation catalyst are initially in different parts of the two or more component curable composition. Particular preference is given to complexes of platinum with vinylsiloxanes, such as sym-divinyltetramethyldisiloxane.

The hydrosilylation catalyst (IV) may also be used in microencapsulated form, in which case the catalyst is present in a finely divided solid insoluble in polyorganosiloxane, for example a thermoplastic (polyester resins, silicone resins). The hydrosilylation catalyst used may also be in the form of an inclusion compound, for example in a cyclodextrin.

The amount of hydrosilylation catalyst used depends on the desired rate of crosslinking and also on economic factors. When the common platinum catalysts are used, the content of platinum metal in the curable silicone rubber material is in the range from 0.1 to 500 ppm by weight (ppm=parts per million parts), preferably from 10 to 100 ppm by weight, of platinum metal. If desired, the catalyst may also be used together with an inhibitor, preferably in amounts of from 0.01 to 5% by weight.

A preferred preparation for an addition-crosslinking HTV silicone rubber is carried out as follows:

75 parts of a dipolyorganosiloxane end-capped by trimethylsiloxy groups, and consisting of 99.7 mol % of dimethylsiloxane units and 0.3 mol % of vinylmethylsiloxane units, having a viscosity of 8×106 mPa·s at 25° C., and 25 parts of a polydiorganosiloxane end-capped by trimethylsiloxy groups, consisting of 99.4 mol % of dimethylsiloxane units and 0.6 mol % of vinylmethylsiloxane units, having a viscosity of 8×106 mPa·s at 25° C., are mixed in a kneader at 150° C. with 45 parts of silicone dioxide produced pyrogenically in the gas phase having a BET surface area of 300 m2/g, and 7 parts of a dimethylpolysiloxane having one Si-bonded hydroxyl group in each terminal unit, having a viscosity of 40 mPa·s at 25° C., and kneaded for 2 hours. After cooling the mixture to room temperature, 5 ppm by weight of platinum, in the form of a 1% strength solution of hexachloroplatinic acid in isopropanol, and 0.2 ppm by weight of benzotriazole are admixed, the ppm by weight figures in each case being based on the entire weight of the mixture described above. A portion of a methylhydrogenpolysiloxane end-capped with trimethylsiloxy groups and having a viscosity of 20 mPa·s at 25° C. is then added to the mixture.

The novel additive, preferably in an amount from 0.1 to 4% by weight, more preferably from 0.4 to 2% by weight, and most preferably from 0.8 to 1.2% by weight, is added to the addition-crosslinking silicone rubber. Pelletization follows using conventional means of pelletizing, such as a pelletizing die and a rotating knife, giving a fully free-flowing pelletized material.

The advantage of the novel additive is that a fully free-flowing pelletized material is obtained without adding pyrogenic silicone dioxide. The purpose of the addition of pyrogenic silicone dioxide has been to reduce the tack of the silicone rubbers, which per se are tacky. The storage stability of mixtures of this type is no more than 24 hours, since the rubber stiffens completely within a few hours. The pelletized silicone rubber material, however, has a storage stability of at least 6 months, and therefore can be satisfactorily processed throughout this period.

EXAMPLE 1

Preparation of the Additive 100 parts of a dimethylpolysiloxane with a viscosity of 8×106 mPa·s are mixed in a kneader with 13 parts of boric acid, 46 parts of silicone dioxide produced pyrogenically in the gas phase and having a surface area of 150 m2/g, 5 parts of calcium stearate, and 30 parts of deionized water and kneaded for 3 hours at 150° C. under nitrogen. During this time, the water serving as solvent for the boric acid is drawn away.

EXAMPLE 2

Preparation of the Peroxidically Crosslinking Silicone Rubber 100 parts of a diorganopolysiloxane end-capped with trimethylsiloxy groups, consisting of 99.93 mol % of dimethylsiloxane units and 0.07 mol % of vinylmethylsiloxane units and having a viscosity of 8×106 mPa·s at 25° C., are mixed in a kneader operated at 150° C., first with 50 parts of silicone dioxide produced pyrogenically in the gas phase, having a surface area of 200 m2/g, then with 1 part of dimethylpolysiloxane end-capped with trimethylsiloxy groups and having a viscosity of 96 mPa·s at 25° C., then with 7 parts of a dimethylpolysiloxane having an Si-bonded hydroxyl group in each terminal unit and having a viscosity of 40 mPa·s at 25° C., then again with 1 part of dimethylpolysiloxane end-capped with trimethylsiloxy groups and having a viscosity of 96 mPa·s at 25° C., and finally with 2.8 parts of a paste made of equal parts of bis(2,4-dichlorobenzoyl) peroxide and of a dimethylpolysiloxane end-capped with trimethylsiloxy groups, having a viscosity of 250 mPa·s at 25° C. Added to the kneader is then 0.8% of the additive of Example 1, and the mixture is processed without difficulty to give a fully free-flowing pelletized material. The production equipment for pelletization is an extruder with a rotating knife on the die.

COMPARATIVE EXAMPLE 1

Example 2 is repeated without the novel additive. The resultant silicone rubber cannot be pelletized, but simply clogs the pelletizing die and knife.

EXAMPLE 3

Preparation of the Addition-Crosslinking Silicone Rubber

Preparation of Component A 75 parts of a diorganopolysiloxane end-capped with trimethylsiloxy groups and consisting of 99.7 mol % of dimethylsiloxane units and 0.3 mol % of vinylmethylsiloxane units having a viscosity of 8×106 mPa·s at 25° C., and 25 parts of a diorganopolysiloxane end-capped with trimethylsiloxy groups, consisting of 99.4 mol % of dimethylsiloxane units and 0.6 mol % vinylmethylsiloxane units having a viscosity of 8×106 mPa·s at 25° C., are mixed in a kneader operated at 150° C. with 45 parts of silicone dioxide produced pyrogenically in the gas phase having a BET surface area of 300 m2/g, and 7 parts of a dimethylpolysiloxane having a Si-bonded hydroxyl group in each terminal unit, having a viscosity of 40 mPa·s at 25° C., and kneaded for 2 hours.

0.19 g of a platinum catalyst, composed of 97 parts by weight of a polydimethylsiloxane and 3 parts by weight of a platinum-divinyltetramethyldisiloxane complex, and 0.07 parts by weight of ethynylcyclohexanol as an inhibitor, are added to 100 parts by weight of the initial silicone mixture after cooling the material to room temperature, and homogenized in a kneader.

Preparation of Component B

A mixture is prepared as described under component A, except that, after cooling the material to room temperature, 4 parts by weight of a polydimethylsiloxane-co-hydromethylpolysiloxane and 0.03 parts by weight of ethynylcyclohexanol, as inhibitor, are added to 100 parts by weight of this initial silicone mixture, instead of the platinum catalyst and inhibitor.

Each of component A and component B is mixed with 0.8% of the additive of Example 1, homogenized in a kneader, and processed without difficulty to give fully free-flowing pelletized materials. The production equipment for this is an extruder with a rotating knife on the die.

COMPARATIVE EXAMPLE 2

Example 3 is repeated without adding the novel additive. The resultant silicone rubber components cannot be pelletized, but simply clog the pelletizing die and knife.

In one embodiment, an injection molding apparatus such as that disclosed in EP 0699512, fully incorporated herein by reference, is used. In one embodiment of injection molding, an injection unit is mounted on a base structure. The injection unit feeds moulding liquid to a distribution plate. A closing unit can be slidably mounted on the base structure and has a mould die. The mould die can include moulding cavities for receiving heat-hardenable moulding silicone rubber to form the wearable device 12.

In one embodiment, a moulding die is pressed against a distribution member where injection nozzles of the distribution member are aligned with the cavities of the mould die. The moulding liquid is then injected into the cavity, and the die is then heated to vulcanize the liquid. Once solidified, the moulding die can then be slid back from the distribution member and the moulded objects in the die cavity, which can be a braclet 12, ejected therefrom. The cycle can then recommence.

In one embodiment, a liquid silicone rubber composition includes a liquid silicone rubber base compound produced by mixing (A) a liquid diorganopolysiloxane containing an optional inorganic filler with (B) a thermoplastic resin hollow-particle powder that expands when heated and performing a heat treatment at a temperature sufficient to cause expansion of component (B) and (C) a curing agent in an amount sufficient to cure the liquid diorganopolysiloxane; a method for manufacturing this composition; and a method for manufacturing a foamed silicone rubber characterized in that the above-mentioned liquid silicone rubber composition is heated and cured.

Component (A) is the main agent and can be diorganopolysiloxane described by average unit formula Ra(OH)bSiO(4−a−b)/2, where R is a monovalent hydrocarbon group or a halogenated alkyl group. Examples of monovalent hydrocarbon groups include alkyl groups such as the methyl, ethyl, and propyl; alkenyl groups such as the vinyl and allyl; cycloalkyl groups such as cyclohexyl; aralkyl groups such as the β-phenylethyl; and aryl groups such as phenyl. Examples of halogenated alkyl groups include chloromethyl, 3-chloropropyl, and 3,3,3-trichloropropyl. In the formula a is a number from 1.9 to 2.1 and b is a number from 0 to 0.1. A diorganopolysiloxane such as this usually has a viscosity (at 25° C.) between 100 and 1,000,000 mPa·s.

The molecular structure of this component (A) is substantially linear, but part of the molecular chain may be slightly branched. Specific examples of this diorganopolysiloxane include dimethylpolysiloxane capped with dimethylvinylsiloxy groups, a copolymer of methylvinylsiloxane and dimethylsiloxane capped with dimethylvinylsiloxy groups, a copolymer of methylvinylsiloxane and dimethylsiloxane capped with silanol groups, a copolymer of methylphenylsiloxane and dimethylsiloxane capped with dimethylvinylsiloxy groups, a copolymer of methylphenylsiloxane, methylvinylsiloxane, and dimethylsiloxane capped with dimethylvinylsiloxy groups, a copolymer of diphenylsiloxane and dimethylsiloxane capped with dimethylvinylsiloxy groups, a copolymer of diphenylsiloxane, methylvinylsiloxane, and dimethylsiloxane capped with dimethylvinylsiloxy groups, a copolymer of methyl(3,3,3-trifluoropropyl)-siloxane and dimethylsiloxane capped with dimethylvinylsiloxy groups, and a copolymer of methyl(3,3,3-trifluoropropyl) siloxane, methylvinylsiloxane, and dimethylsiloxane capped with dimethylvinylsiloxy groups.

Component (A) may contain an optional inorganic filler that serves to impart mechanical strength to the silicone rubber. The inorganic filler can be any that is known as a reinforcing filler or semi-reinforcing filler of silicone rubber. Examples of reinforcing fillers include dry process silica, wet process silica, hydrophobic silica where the surface of one of these types of silica has been treated with an organochlorosilicon, organoalkoxysilane, organopolysiloxane, organosilazane, or the like; carbon black; and colloidal calcium carbonate. Of these, particulate silica with a specific surface area of at least 100 m2/g are preferable. Examples of non-reinforcing fillers include diatomaceous earth, quartz powder, mica, aluminum oxide, and titanium oxide.

Component (B) is a thermoplastic resin hollow-particle powder that expands when heated and comprises a volatile substance enclosed in spherical shells composed of a thermoplastic resin. Examples of the thermoplastic resin that forms the shell of this component include polyethylene, polystyrene, polyvinyl acetate, polyvinyl chloride, polyvinylidene chloride, polyacrylonitrile, polymethyl methacrylate, polybutadiene, polychloroprene, and other vinyl polymers and copolymers; nylon 6, nylon 66, and other polyamides; and polyethylene terephthalate, polyacetal, and blends of these. Examples of the volatile substance enclosed in the thermoplastic resin hollow-particle powder include butane, isobutane, propane, and other hydrocarbons; methanol, ethanol, and other alcohols; dichloroethane, trichloroethane, trichloroethylene, and other halogenated hydrocarbons; and diethyl ether, isopropyl ether, and other ethers. It is preferable for the particle diameter of component (B) to be 1 to 50 μm prior to expansion and 5 to 200 μm after expansion. This is because thermal conductivity will not be low if this particle diameter is less than 1 μm, but if 50 μm is exceeded, the strength of the thermoplastic resin hollow-particle powder will decrease to the point that the particles will break up during compounding into the liquid silicone rubber base composition. The amount in which component (B) is compounded is usually 0.1 to 15 wt % in the composition. This is because thermal conductivity will not be low if the amount is less than this, but if the amount is larger than this the viscosity of the liquid silicone rubber base composition will be too high for processing or the thermal conductivity will be too low and heat treatment will take a long time.

The liquid silicone rubber compound is obtained by mixing the above-mentioned component (B) into component (A) then expanding component (B) by performing a heat treatment at a temperature over the thermal expansion commencement temperature of this component (B). The temperature at which the mixture of components (A) and (B) is heat treated is usually between 80 and 180° C. How much component (B) is expanded will vary with the type of component (B) being used and other factors, but component (B) can be expanded up to, but not including, the size at which the shell breaks.

The curing agent of component (C) can be an organic peroxide, or a platinum-based catalyst can be used together with an organopolysiloxane containing hydrogen atoms bonded to silicone atoms. Examples of the organic peroxide include benzoyl peroxide, t-butyl benzoate, o-methylbenzoyl peroxide, p-methylbenzoyl peroxide, m-methylbenzoyl peroxide, dicumyl peroxide, and 2,5-dimethyl-2,5-di-(t-butylperoxy)hexane. The amount at which this component is compounded is between 0.1 and 10 weight parts per 100 weight parts component (A).

As to the latter use of a platinum-based catalyst together with an organopolysiloxane containing hydrogen atoms bonded to silicone atoms, examples of the platinum-based catalyst include platinum fines, platinum black, chloroplatinic acid, alcohol-modified chloroplatinic acid, an olefin complex of chloroplatinic acid, and a complex compound of chloroplatinic acid and an alkenylsiloxane. The organopolysiloxane containing hydrogen atoms bonded to silicone atoms serves as a crosslinking agent to cure the composition through reaction with the above-mentioned component (A) in the presence of a platinum-based catalyst. Examples of such an organopolysiloxane containing hydrogen atoms bonded to silicon atoms include methylhydrogenpolysiloxane capped at both ends with trimethylsiloxy groups, a copolymer of methylhydrogensiloxane and dimethylsiloxane capped at both ends with trimethylsiloxy groups, a copolymer of methylhydrogensiloxane and dimethylhydrogensiloxane capped at both ends with dimethylhydrogensiloxy groups, and tetramethyltetrahydrogencyclotetrasiloxane. In this case, a known compound such as 1-ethynyl-cyclohexanol, 3-methyl-1-penten-3-ol, 3,5-dimethyl-1-hexyn-3-ol, or benzotriazole can be added as an inhibitor of catalytic activity of the platinum-based catalyst.

In one embodiment, the composition is a liquid silicone rubber base compound composed of the above-mentioned component (A), component (B), and component (C), but as long as the object of composition is not compromised, various additives known to be added to silicone rubber compositions may also be used in addition to the above components. Such additional components include carbon black, iron oxide red, and other pigments; rare earth oxides; rare earth hydroxides; cerium silanolate, cerium fatty acid salts, and other heat resistance agents; fumed titanium dioxide, carbon black, zinc carbonate, and various other flame retardants; and internal release agents.

The composition that can be used for the monitoring device structure can be manufactured by compounding the above-mentioned component (C) with the liquid silicone rubber base compound composed of component (A) and component (B). Any of various mixers used in the manufacture of silicone rubber compositions can be used for the manufacturing apparatus here, examples of which include a kneader mixer, pressurized kneader mixer, Ross mixer, continuous kneader extruder, and other such mixers.

When heated and cured, the composition becomes a foamed silicone rubber. The heating temperature here is usually at least 100° C., and a range of 100 to 180° C. is preferable. The foamed silicone rubber thus obtained usually has a thermal conductivity between 0.05 and 0.17 W/(m·K).

The composition as described above is easy to work with in mixing and upon curing becomes a foamed silicone rubber with a low thermal conductivity. Therefore, this composition can be used to advantage in applications that demand these characteristics, such as thermal insulating gaskets, thermal insulating sealants, thermal insulating adhesives, coatings for copier rolls, and so forth.

Various embodiments of useful compositions for the monitoring device structure will now be described through examples. In these examples, "parts" indicates "weight parts," and viscosity is the value measured at 25° C. The hardness of the foamed silicone rubber was measured according to JIS K 6249. Thermal conductivity was measured according to JIS R 2618.

EXAMPLE 1

100 Parts of a dimethylpolysiloxane that was capped at both ends of the molecular chain with dimethylvinylsiloxy groups and that had a viscosity of 2000 mPa·s and 10 parts of fumed silica that had been treated with hexamethyldisilazane and had a BET specific surface area of 130 m2/g were put into a Ross mixer and mixed until uniform to prepare a compound that had fluidity. Next, 5 weight parts of a thermoplastic resin hollow-particle powder enclosing isobutane on the inside (this hollow-particle powder had a particle diameter between 10 and 16 μm, and its expansion commencement temperature was between 120 and 128° C.; this powder is commercially available under the brand name "Expancell 091DU" from Expancell) was added and mixed until uniform. This mixture was heated treated at a temperature of 170° C. to prepare a liquid silicone rubber base compound that had fluidity. To this liquid silicone rubber base compound were then added 2 parts of a copolymer of dimethylsiloxane and methylhydrogensiloxane capped at both ends with trimethylsiloxy groups and composed of 4 mol dimethylsiloxane units and 6 mol of methylhydrogensiloxane units, 0.15 part (0.4 wt % platinum content) of a complex of chloroplatinic acid and divinyltetramethyldisiloxane, and 0.05 part 3,5-dimethyl-1-hexyn-3-ol (used as a curing inhibitor), and these components were mixed until uniform to prepare a liquid silicone rubber composition. The viscosity of this composition was 600 Pa·s. This composition was then press cured at 120° C. to obtain a foamed silicone rubber with a thickness of 6 mm. This foamed silicone rubber was sliced and the cut surface thereof was observed under a microscope, which revealed that the size of the cells included in this foam was between 30 and 50 µm, and the cells were uniform in size. The specific gravity of this foamed silicone rubber was 0.60, the hardness was 30, and the thermal conductivity was 0.13 W/(m·K). These results are given in Table 1 below.

COMPARATIVE EXAMPLE 2

100 Parts of a dimethylpolysiloxane that was capped at both ends of the molecular chain with dimethylvinylsiloxy groups and that had a viscosity of 2000 mPa·s and 10 parts of fumed silica that had been treated with hexamethyldisilazane and had a BET specific surface area of 130 m2/g were put into a Ross mixer and mixed until uniform to prepare a compound that had fluidity. Next, 5 weight parts of a thermoplastic resin hollow-particle powder enclosing isobutane on the inside (this hollow-particle powder had a particle diameter between 10 and 16 µm, and its expansion commencement temperature was between 120 and 128° C.; this powder is commercially available under the brand name "Expancell 091DU" from Expancell) was added and mixed until uniform to prepare a liquid silicone rubber base compound that had fluidity. To this liquid silicone rubber base compound were then added 2 parts of a copolymer of dimethylsiloxane and methylhydrogensiloxane capped at both ends with trimethylsiloxy groups and composed of 4 mol of dimethylsiloxane units and 6 mol of methylhydrogensiloxane units, 0.15 part (0.4 wt % platinum content) of a complex of chloroplatinic acid and divinyltetramethyldisiloxane, and 0.05 part 3,5-dimethyl-1-hexyn-3-ol (used as a curing inhibitor), and these components were mixed until uniform to prepare a liquid silicone rubber composition. The viscosity of this composition was 90 Pa·s. This composition was then press cured at 120° C. to obtain a foamed silicone rubber with a thickness of 6 mm. This foamed silicone rubber was sliced and the cut surface thereof was observed under a microscope, which revealed that the size of the cells included in this foam was between 10 and 20 µm, and the cells had hardly expanded at all. The specific gravity of this foamed silicone rubber was 1.02, the hardness was 30, and the thermal conductivity was 0.19 W/(m·K). These results are given in Table 1 below.

COMPARATIVE EXAMPLE 3

100 Parts of a dimethylpolysiloxane that was capped at both ends of the molecular chain with dimethylvinylsiloxy groups and that had a viscosity of 2000 mPa·s and 10 parts of fumed silica that had been treated with hexamethyldisilazane and had a BET specific surface area of 130 m2/g were put into a Ross mixer and mixed until uniform to prepare a compound that had fluidity. Next, 5 weight parts of a hollow-particle powder that had already been expanded by heating a thermoplastic resin hollow-particle powder enclosing isobutane on the inside (this hollow-particle powder had a particle diameter between 35 and 55 µm, and is commercially available under the brand name "Expancell 091DE" from Expancell) was added and mixed until uniform to prepare a liquid silicone rubber base composition that had fluidity. This previously heated and expanded hollow-particle powder was extremely prone to scattering, and furthermore was high in bulk, which made it tremendously difficult to work with in mixing. To this liquid silicone rubber base composition were then added 2 parts of a copolymer of dimethylsiloxane and methylhydrogensiloxane capped at both ends with trimethylsiloxy groups and composed of 4 mol dimethylsiloxane units and 6 mol of methylhydrogensiloxane units, 0.15 part (0.4 wt % platinum content) of a complex of chloroplatinic acid and divinyltetramethyldisiloxane, and 0.05 part 3,5-dimethyl-1-hexyn-3-ol (used as a curing inhibitor), and these components were mixed until uniform to prepare a liquid silicone rubber composition. The viscosity of this composition was 900 Pa·s. This composition was then press cured at 120° C. to obtain a foamed silicone rubber with a thickness of 6 mm. This foamed silicone rubber was sliced and the cut surface thereof was observed under a microscope, which revealed that the size of the cells included in this foam was between 30 and 50 µm, and the cells were uniform in size. The specific gravity of this foamed silicone rubber was 0.62, the hardness was 32 (JIS type A), and the thermal conductivity was 0.14 W/(m·K). These results are given in Table 1 below.

COMPARATIVE EXAMPLE 4

100 Parts of a dimethylpolysiloxane that was capped at both ends of the molecular chain with dimethylvinylsiloxy groups and that had a viscosity of 2000 mPa·s and 10 parts of fumed silica that had been treated with hexamethyldisilazane and had a BET specific surface area of 130 m2/g were put into a Ross mixer and mixed until uniform to prepare a compound that had fluidity. Next, 5 weight parts of a hollow-particle powder that had undergone an anti-scattering treatment, in which a hollow-particle powder that had already been expanded by heating a thermoplastic resin hollow-particle powder enclosing isobutane on the inside (this hollow-particle powder had a particle diameter between 35 and 55 µm, and is commercially available under the brand name "Expancell 091DE" from Expancell) was treated by air spraying with 5 parts of a dimethylpolysiloxane having a viscosity of 10 mPa·s, was added and mixed until uniform to prepare a liquid silicone rubber base compound that had fluidity. This hollow-particle powder that had undergone the anti-scattering treatment posed no problem in mixing. To this liquid silicone rubber base composition were then added 2 parts of a copolymer of dimethylsiloxane and methylhydrogensiloxane capped at both ends with trimethylsiloxy groups and composed of 4 mol of dimethylsiloxane units and 6 mol of methylhydrogensiloxane units, 0.15 part (0.4 wt % platinum content) of a complex of chloroplatinic acid and divinyltetramethyldisiloxane, and 0.05 part 3,5-dimethyl-1-hexyn-3-ol (used as a curing inhibitor), and these components were mixed until uniform to prepare a liquid silicone rubber composition. The viscosity of this composition was 500 Pa·s. This composition was then press cured at 120° C. to obtain a foamed silicone rubber with a thickness of 6 mm. This foamed silicone rubber was sliced and the cut surface thereof was observed under a microscope, which revealed that the size of the cells included in this foam was between 30 and 50 μm, and the cells were uniform in size. The specific gravity of this foamed silicone rubber was 0.60, the hardness was 28 (JIS type A), and the thermal conductivity was 0.14 W/(m·K). These results are given in Table 1 below.

COMPARATIVE EXAMPLES 4 and 5

A silicone rubber composition (Comparative Example 4) was prepared by the same procedure as Example 1 except that di-n-hexylsulphide was omitted.

A silicone rubber composition (Comparative Example 5) was prepared by the same procedure as Example 1 except that di-n-hexylsulphide was omitted and ethynylcyclohexanol was added instead.

TABLE 1

|  | Example | Comparative Example | | |
|---|---|---|---|---|
|  | Example 1 | Comp. Ex. 1 | Comp. Ex. 2 | Comp. Ex. 3 |
| Type of thermoplastic resin hollow-particle powder | unexpanded hollow-particle powder | unexpanded hollow-particle powder | pre-expanded hollow-particle powder | pre-expanded hollow-particle powder treated with oil |
| Ease of work during mixing | good | good | good | good |
| Viscosity (Pa · s) | 600 | 90 | 900 | 500 |
| Curing temp. (° C.) | 120 | 120 | 120 | 120 |
| Hardness (type A) | 30 | 30 | 32 | 28 |
| Specific gravity | 0.60 | 1.02 | 0.62 | 0.60 |
| Thermal conductivity (W/(m · K)) | 0.13 | 0.19 | 0.14 | 0.14 |
| Oil seepage | no | no | no | yes |

Other suitable silicon rubbers are disclosed in EP 0654497.

In one embodiment, a platinum paste B was prepared by mixing 10 grams of a low-degree-of-polymerization dimethylvinylpolysiloxane substituted solution of a chloroplatinic acid-alcohol solution (having a vinyl content 0.7 mol % and a platinum content of 1.0%) and 90 grams of an organopolysiloxane having a vinyl content of 0.15 mol % and an average degree of polymerization of 5,000.

To 100 parts of an organopolysiloxane consisting of 99.85 mol % of a dimethylsiloxane $(CH_3)_2SiO$ unit and 0.15 mol % of a methylvinylsiloxane $(CH_3)(CH=CH_2)SiO$ unit and terminated with a dimethylvinylsiloxane $(CH_3)_2(CH=CH_2)SiO_{1/2}$ unit at either end were added 45 parts of fumed silica (Aerosil 200 commercially available from Nippon Aerosil K.K.) and 7 parts of hydroxyl-end-blocked dimethylsilicone fluid having a degree of polymerization (n) of 10. The ingredients were mixed in a kneader and then heat treated at 160 to 170° C. for 2 hours, obtaining a rubber compound.

To 100 parts of the rubber compound were added 0.5 part of platinum paste B as a curing agent, 0.05 or 0.1 part of di-n-hexylsulphide, and 1.2 parts of organohydrogenpolysiloxane having a Si—H content of 0.005 mol/g. The ingredients were milled to form silicone rubber compositions (Examples 1 and 2).

A silicone rubber composition (Example 3) was prepared by the same procedure as Example 1 expect that 0.1 part of a conventional known control agent, ethynylcyclohexanol, was further added to the composition of Example 1.

EXAMPLES 5 and 6

A platinum paste C was prepared by mixing 10 grams of a low-degree-of-polymerization dimethylvinylpolysiloxane substituted solution of a chloroplatinic acid-alcohol solution (having a vinyl content 0.7 mol % and a platinum content of 1.0%), 1.0 grams of 2,4,6-tris(t-butylperoxy)-1,3,5-triazine (commercially available from Kayaku Akuzo K.K.), and 89 grams of an organopolysiloxane having a vinyl content of 0.15 mol % and an average degree of polymerization of 5,000.

To 100 parts of the same rubber compound as in Example 1 were added 0.5 part of platinum paste C as a curing agent, 0.02 part of ditridecyl-3,3'-thiodipropionate, and 1.2 parts of organohydrogenpolysiloxane having a Si—H content of 0.005 mol/g. The ingredients were milled to form a silicone rubber compositions (Example 4).

Silicone rubber compositions (Examples 5 and 6) were prepared by the same procedure as Example 4 except that 0.01 part of di-n-hexylsulphide or n-octylsulphide was added instead of ditridecyl-3,3'-thiodipropionate.

Each of the resultant silicone rubber compositions was allowed to stand in a dryer at 40° C. such that no air was directly blown to the composition. A gel time was measured. The gelling point was judged by milling a sheet 1 mm thick between two rolls ten rounds, wrapping the sheet around roll, and observing whether the sheet surface texture was smooth. When the surface texture was smooth, the sheet was judged not gelled. The results are shown in Tables 1 and 2.

TABLE 1

| Composition (pbw) | Example 1 | Example 2 | Example 3 | Comparative Example 1 | Comparative Example 2 |
|---|---|---|---|---|---|
| Rubber compound | 100 | 100 | 100 | 100 | 100 |
| Platinum paste B | 0.5 | 0.5 | 0.5 | 0.5 | 0.5 |
| Di-n-hexylsulphide | 0.05 | 0.1 | 0.05 | — | — |
| Ethynylcyclohexanol | — | — | 0.1 | — | 0.1 |

TABLE 1-continued

|  | | | | | |
|---|---|---|---|---|---|
| Organohydrogenpolysiloxane | 1.2 | 1.2 | 1.2 | 1.2 | 1.2 |
| Gel time at 40° C. | 6 days | 15 days | 10 days | 15 minutes | 1 day |

| Composition (pbw) | Example 4 | Example 5 | Example 6 |
|---|---|---|---|
| Rubber Composition | 100 | 100 | 100 |
| Platinum paste C | 0.5 | 0.5 | 0.5 |
| Ditridecyl-3,3'-thiodipropionate | 0.02 | — | — |
| Di-n-decyldisulphide | — | 0.01 | — |
| n-Octylsulphide | — | — | 0.01 |
| Organohydrogenpolysiloxane | 1.2 | 1.2 | 1.2 |
| Gel time at 40° C. | 30 days | 28 days | 30 days |

As is evident from Tables 1 and 2, silicone rubber compositions exploiting our new proposals have a very long gel time at 40° C. and are potentially curable compositions which are stabilized against premature gelation.

The foregoing description of various embodiments of the claimed subject matter has been provided for the purposes of illustration and description. it is not intended to be exhaustive or to limit the claimed subject matter to the precise forms disclosed. Many modifications and variations will be apparent to the practitioner skilled in the art. Particularly, while the concept "component" is used in the embodiments of the systems and methods described above, it will be evident that such concept can be interchangeably used with equivalent concepts such as, class, method, type, interface, module, object model, and other suitable concepts. Embodiments were chosen and described in order to best describe the principles of the invention and its practical application, thereby enabling others skilled in the relevant art to understand the claimed subject matter, the various embodiments and with various modifications that are suited to the particular use contemplated.

What is claimed is:

1. A wearable device, comprising: a frame;
a wearable device structure with a first and a second end;
a fastening element that couples the first end to the second end; and
an electronic device coupled to the wearable device structure, the electronic device coupled to the wearable device structure, including one or more haptic device sensors that accepts input from the user based on haptic motion, the electronic device including a payment activity manager configured to receive from a user payment configuration parameters for each of a designated third party to receive payments, the payment activity manager including a designated third party payment data base that includes designated third party settings with third party IP addresses, payment sources for each of a designated third party, and method of payment, the payment activity manager performing a comparison for each of a designated third party to receive a payment and perform a security check on that designated third party, the payment activity manager performing an authentication of a designated third party for a payment and a tracking of payments for each of a payment transaction to the one or more designated third parties including an initiation of a payment and a conclusion of a payment from the user, the payment activity manager associating one or more transaction contexts of a designated third party payment prior to payment, the electronic component including a stock activity manager associating one or more stocks of a public company, the stock activity manager configured to monitor activity of a selected stock, accept stock settings made by the user or requested by a designated party, the stock activity manager configured to manage a user instruction to buy or sell one or more stocks, and also calendar one or more notifications to the user to review one or more stocks performance, and to execute the purchase or sale of one or more stocks designated by the user.

2. The device of claim 1, wherein the frame is at least partially made of a thermoplastic.

3. The wearable device of claim 1, wherein the frame holds at least a portion of electronic circuitry.

4. The device of claim 1, wherein the frame provides protection for at least one of, a sensor, electronic circuitry and magnet, from torsional and mechanical forces imparted to the wearable device.

5. The device of claim 4, wherein the protection from mechanical forces by the frame is in an amount that does not exceed: pull force: 0.5 to 100 kgf, (stretching of the wearable device 10); bend force: 0.5 to 100 kgf (bending of the wearable device 10); and shear force: 0.5 to 100 kgf (shearing of the wearable device 10).

6. The device of claim 4, wherein the protection from torsional forces by the frame is an amount of a torsional strength in the range of 0.25 to 50 Ncm (twisting of the wearable device).

7. The device of claim 1, wherein the frame includes a living hinge.

8. The device of claim 7, wherein the living hinge provides for flexure and hinging by the living hinge itself without additional elements.

9. The device of claim 1, further comprising:
one or more batteries coupled to the electronic circuitry.

10. The device of claim 1, wherein the wearable device structure is at least partially made of silicone rubber.

11. The device of claim 10, wherein the silicone rubber has a specific gravity of 1 to 1.5.

12. The device of claim 10, further comprising:
at one least one coating applied to at least a portion of the silicone rubber.

13. The device of claim 12, wherein the coating is an anti-microbial coating.

14. The device of claim 1, wherein the silicone rubber has a hardness, type A of 20-80.

15. The device of claim 1, wherein the at least a portion of the sensors are configured to be in communication with a telemetry system.

16. The device of claim 1, wherein at least one of the sensors acquires user information selected from of at least one of, a user's activities, behaviors and habit information, and user monitoring.

17. The device of claim 1, wherein the wearable device includes an application for monitoring exercise activity of a user.

18. The device of claim 1, further comprising:
a pathway system to route signals through circuitry of the wearable device.

19. The device of claim 1, wherein the wearable device is a wristband.

20. The device of claim 1, wherein the wearable device structure includes one or more undercuts that enable magnets to be retained by the wearable device structure.

* * * * *